US012491128B2

(12) United States Patent
Black

(10) Patent No.: US 12,491,128 B2
(45) Date of Patent: Dec. 9, 2025

(54) SYSTEM AND METHOD FOR PERFORMING TISSUE TREATMENT USING POWERED TREATMENT DEVICES

(71) Applicant: ASHLEY DIANA BLACK INTERNATIONAL HOLDINGS, LLC, Pearland, TX (US)

(72) Inventor: Ashley D. Black, Pearland, TX (US)

(73) Assignee: ASHLEY DIANA BLACK INTERNATIONAL HOLDINGS, LLC, Pearland, TX (US)

( * ) Notice: Subject to any disclaimer, the term of this patent is extended or adjusted under 35 U.S.C. 154(b) by 811 days.

(21) Appl. No.: 17/545,920

(22) Filed: Dec. 8, 2021

(65) Prior Publication Data

US 2023/0172799 A1 Jun. 8, 2023

Related U.S. Application Data

(60) Provisional application No. 63/286,536, filed on Dec. 6, 2021.

(51) Int. Cl.

*A61H 23/02* (2006.01)
*A61N 5/06* (2006.01)

(52) U.S. Cl.

CPC ....... *A61H 23/0254* (2013.01); *A61N 5/0616* (2013.01); *A61H 2201/0157* (2013.01);

(Continued)

(58) Field of Classification Search

CPC .............. A61H 23/00; A61H 23/02–04; A61H 7/00–005; A61H 7/007;

(Continued)

(56) References Cited

U.S. PATENT DOCUMENTS

| | | | |
|---|---|---|---|
| D21,551 | S | 5/1892 | Young |
| 687,363 | A | 11/1901 | Wirt |

(Continued)

FOREIGN PATENT DOCUMENTS

| | | | |
|---|---|---|---|
| AU | 655910 | B3 | 1/1995 |
| CN | 2438449 | Y | 7/2001 |

(Continued)

OTHER PUBLICATIONS

’057 Patent Holder Disclosure “Product Development LumpBuster Case Study” (LB Case) date May 26, 2013, pdf archive link: https://web.archive.org/web/20111228161639/http://www.chinatraderonline.com/Beauty-Equipment/Octopus-Massager-13342511.htm, 2 pgs.

(Continued)

*Primary Examiner* — Rachel T Sippel
(74) *Attorney, Agent, or Firm* — Foley & Lardner LLP

(57) ABSTRACT

A treatment system for restructuring and revitalizing fascia tissue. The treatment system may include a base station that powers tissue treatment devices that are used to treat fascia or other tissue of patients. The tissue treatment devices may be powered devices, and include actuators that are used to move tissue treatment elements. The actuators may be motors that cause an effector inclusive of a support structure, such as a disc or other shaped structural member, on which the tissue treatment elements are connected or formed. In an embodiment, the effector may be a unitary piece, where a support structure and protrusions or fingers extend. Alternatively, the fingers may be detachably coupled to the support structure. The fingers may have a base that connects to or is integrated with the support structure, curved shafts, and rounded tips.

8 Claims, 58 Drawing Sheets

(52) U.S. Cl.
CPC .................. *A61H 2201/169* (2013.01); *A61H 2201/5061* (2013.01); *A61H 2201/5071* (2013.01); *A61N 2005/0644* (2013.01); *A61N 2005/0652* (2013.01)

(58) Field of Classification Search
CPC .. A61H 15/0078–02; A61H 2201/0157; A61H 2201/169; A61H 2201/5061; A61H 2201/5071; A61N 5/0616; A61N 2005/0644; A61N 2005/065–0652
See application file for complete search history.

(56) References Cited

U.S. PATENT DOCUMENTS

| | | | | |
|---|---|---|---|---|
| 912,016 | A | 2/1909 | Willis | |
| 965,564 | A | 7/1910 | Coates | |
| 1,002,509 | A | 9/1911 | Fitz | |
| D55,452 | S | 6/1920 | Chase | |
| 1,523,979 | A | 1/1925 | Ryan | |
| 1,713,756 | A | 5/1929 | Hassler | |
| 2,168,975 | A | 8/1939 | Dumont | |
| D140,384 | S | 2/1945 | Latshaw | |
| 2,468,327 | A | 4/1949 | Hartung | |
| 2,480,023 | A | 8/1949 | Holden | |
| 2,972,347 | A | 2/1961 | Mcnair | |
| D197,889 | S | 4/1964 | Hass | |
| D208,894 | S | 10/1967 | Wedermeyer | |
| D213,690 | S | 4/1969 | Eckstrom | |
| D233,632 | S | 11/1974 | Kirk | |
| 3,856,002 | A | 12/1974 | Matsumoto | |
| 3,862,662 | A | 1/1975 | Kern | |
| D234,724 | S | 4/1975 | Tavel | |
| 3,906,940 | A | 9/1975 | Kawada | |
| 4,023,567 | A | 5/1977 | Wessel | |
| 4,091,805 | A | 5/1978 | Clark | |
| 4,173,217 | A | 11/1979 | Johnston | |
| D260,928 | S | 9/1981 | Gueret | |
| 4,345,757 | A | 8/1982 | Lo Voi | |
| D269,375 | S | 6/1983 | Masuda | |
| D270,279 | S | 8/1983 | Hamilton | |
| D272,090 | S | 1/1984 | Hosid | |
| 4,454,867 | A | 6/1984 | Swanson | |
| 4,493,315 | A | 1/1985 | Iwahashi | |
| D279,126 | S | 6/1985 | Kaeser | |
| D280,434 | S | 9/1985 | Mcmanaway | |
| D280,664 | S | 9/1985 | Ishida | |
| D281,815 | S | 12/1985 | Conn et al. | |
| D282,007 | S | 12/1985 | Mckinney | |
| D300,853 | S | 4/1989 | Smal | |
| D315,408 | S | 3/1991 | Duk | |
| D319,645 | S | 9/1991 | Geib | |
| 5,044,356 | A | 9/1991 | Fishman et al. | |
| 5,103,809 | A | 4/1992 | Deluca et al. | |
| D331,466 | S | 12/1992 | Doria | |
| D333,351 | S | 2/1993 | Tsou | |
| D342,319 | S | 12/1993 | Cheng | |
| 5,285,774 | A | 2/1994 | Stachurski | |
| D345,054 | S | 3/1994 | Spence | |
| D346,866 | S | 5/1994 | Lotuaco | |
| D349,576 | S | 8/1994 | Heiligenstein et al. | |
| D349,771 | S | 8/1994 | Heiligenstein et al. | |
| D350,608 | S | 9/1994 | Yu | |
| D350,851 | S | 9/1994 | Spence | |
| D351,658 | S | 10/1994 | Beckman | |
| 5,352,188 | A | 10/1994 | Vitko | |
| D359,358 | S | 6/1995 | Pecora et al. | |
| 5,445,596 | A | 8/1995 | Grace | |
| 5,483,719 | A | 1/1996 | Ikemoto et al. | |
| D369,447 | S | 4/1996 | Mann et al. | |
| D373,197 | S | 8/1996 | Schepper | |
| D374,084 | S | 9/1996 | Chen | |
| D376,853 | S | 12/1996 | Hsia | |
| 5,588,953 | A | 12/1996 | Chang | |
| 5,647,841 | A | 7/1997 | Groenewold et al. | |
| D384,157 | S | 9/1997 | Kusnets et al. | |
| 5,674,261 | A | 10/1997 | Smith | |
| D387,873 | S | 12/1997 | Lee | |
| D390,966 | S | 2/1998 | Huang | |
| D391,645 | S | 3/1998 | Chien | |
| D392,424 | S | 3/1998 | Burys | |
| 5,728,050 | A | 3/1998 | Lin | |
| 5,730,708 | A | 3/1998 | Spratt | |
| D396,296 | S | 7/1998 | Breznik | |
| D398,401 | S | 9/1998 | Antoskow | |
| 5,823,145 | A | 10/1998 | Hingiss | |
| D403,429 | S | 12/1998 | Blanchard | |
| D403,430 | S | 12/1998 | Chien | |
| D404,495 | S | 1/1999 | Chien | |
| D408,925 | S | 4/1999 | Berry et al. | |
| D419,681 | S | 1/2000 | Chen | |
| D422,084 | S | 3/2000 | Mickelson | |
| D422,086 | S | 3/2000 | Chen | |
| D422,365 | S | 4/2000 | Chen | |
| D427,318 | S | 6/2000 | Chen | |
| D428,997 | S | 8/2000 | Berry et al. | |
| D430,936 | S | 9/2000 | Noble | |
| 6,139,553 | A | 10/2000 | Dotan | |
| D435,110 | S | 12/2000 | Chen | |
| D435,295 | S | 12/2000 | Yoo | |
| 6,179,229 | B1 | 1/2001 | Desmond | |
| 6,190,339 | B1 | 2/2001 | Imazaike et al. | |
| D443,067 | S | 5/2001 | Chen | |
| 6,241,693 | B1 | 6/2001 | Lambden | |
| 6,241,696 | B1 | 6/2001 | York | |
| D444,883 | S | 7/2001 | Chen | |
| 6,267,738 | B1 | 7/2001 | Louis | |
| D447,809 | S | 9/2001 | Gladieux et al. | |
| D449,695 | S | 10/2001 | Ponton et al. | |
| D454,959 | S | 3/2002 | Harris et al. | |
| 6,357,075 | B1 | 3/2002 | Kaizuka | |
| D455,837 | S | 4/2002 | Kim | |
| 6,412,997 | B2 | 7/2002 | Berke et al. | |
| D466,612 | S | 12/2002 | Harris et al. | |
| D468,084 | S | 1/2003 | Lin | |
| D468,829 | S | 1/2003 | Chen | |
| D469,879 | S | 2/2003 | Chen | |
| 6,536,970 | B2 | 3/2003 | Hauser et al. | |
| D473,657 | S | 4/2003 | Lewis-Jonsson | |
| 6,543,954 | B2 | 4/2003 | Owings | |
| D477,414 | S | 7/2003 | Chen | |
| 6,588,964 | B1 | 7/2003 | Au et al. | |
| D479,607 | S | 9/2003 | Chen | |
| D480,148 | S | 9/2003 | Chen | |
| D484,608 | S | 12/2003 | Tinsley | |
| D486,236 | S | 2/2004 | Nan | |
| 6,758,826 | B2 | 7/2004 | Luettgen et al. | |
| D495,803 | S | 9/2004 | Gough et al. | |
| D499,810 | S | 12/2004 | Chien | |
| D504,954 | S | 5/2005 | Park | |
| D510,440 | S | 10/2005 | Huang | |
| 6,974,427 | B1 | 12/2005 | Lapham | |
| D515,219 | S | 2/2006 | Nan | |
| D515,702 | S | 2/2006 | Nan | |
| 7,003,849 | B2 | 2/2006 | Cohen et al. | |
| 7,037,016 | B1 | 5/2006 | Nelson | |
| D523,962 | S | 6/2006 | Huang | |
| D530,428 | S | 10/2006 | Huang | |
| D530,822 | S | 10/2006 | Inubushi | |
| D532,113 | S | 11/2006 | Huang | |
| 7,153,282 | B1 * | 12/2006 | Dudley | A61H 7/004 601/93 |
| D537,892 | S | 3/2007 | Moses | |
| D538,435 | S | 3/2007 | Wang et al. | |
| 7,238,163 | B1 | 7/2007 | Fried et al. | |
| D548,849 | S | 8/2007 | Huang | |
| 7,291,101 | B2 | 11/2007 | Deal | |
| D556,913 | S | 12/2007 | Laituri | |
| D558,355 | S | 12/2007 | Huang | |
| D565,304 | S | 4/2008 | Stewart | |
| D582,049 | S | 12/2008 | Ferber et al. | |
| D590,510 | S | 4/2009 | Johansen et al. | |
| D599,061 | S | 8/2009 | Smith | |
| D600,357 | S | 9/2009 | Chaput | |

(56) References Cited

U.S. PATENT DOCUMENTS

| | | | |
|---|---|---|---|
| D613,416 | S | 4/2010 | Schupman |
| D626,240 | S | 10/2010 | Copeland et al. |
| D627,897 | S | 11/2010 | Yde et al. |
| D627,898 | S | 11/2010 | Aulwes et al. |
| D630,761 | S | 1/2011 | Marshall |
| D633,217 | S | 2/2011 | Robertson et al. |
| D643,933 | S | 8/2011 | Watabe |
| D648,860 | S | 11/2011 | Donahue et al. |
| D650,488 | S | 12/2011 | Donahue et al. |
| D652,525 | S | 1/2012 | Caggiano et al. |
| D656,277 | S | 3/2012 | Mckee |
| D664,298 | S | 7/2012 | Grabes et al. |
| D672,925 | S | 12/2012 | Hungerford |
| D673,285 | S | 12/2012 | Rivero |
| 8,337,438 | B2 | 12/2012 | Schupman |
| D673,687 | S | 1/2013 | Zeng et al. |
| D674,107 | S | 1/2013 | Prudent et al. |
| D674,905 | S | 1/2013 | Lowsky |
| D674,911 | S | 1/2013 | Caldwell |
| D676,975 | S | 2/2013 | Bickford |
| D677,391 | S | 3/2013 | Bickford |
| D678,540 | S | 3/2013 | Bickford |
| 8,419,663 | B2 | 4/2013 | Eitzen |
| D692,569 | S | 10/2013 | Samurin |
| D694,415 | S | 11/2013 | Viner et al. |
| D703,825 | S | 4/2014 | Barrett |
| D704,852 | S | 5/2014 | Yang |
| D708,755 | S | 7/2014 | Kim |
| D712,053 | S | 8/2014 | Matsushita |
| D712,058 | S | 8/2014 | Huang |
| 8,808,208 | B2 | 8/2014 | Mouatt |
| D716,467 | S | 10/2014 | Kanbar et al. |
| D719,664 | S | 12/2014 | Riftin et al. |
| D721,420 | S | 1/2015 | Hawkins |
| D721,421 | S | 1/2015 | Hawkins |
| D721,440 | S | 1/2015 | Pursel et al. |
| 8,954,155 | B2 | 2/2015 | Campbell |
| D723,709 | S | 3/2015 | Topolovac et al. |
| D724,752 | S | 3/2015 | Huang |
| D725,788 | S | 3/2015 | Matsushita |
| D732,181 | S | 6/2015 | Viner et al. |
| 9,050,240 | B2 | 6/2015 | Howsam |
| D735,818 | S | 8/2015 | Black |
| D739,546 | S | 9/2015 | Cheung |
| 9,125,481 | B2 | 9/2015 | Watanabe et al. |
| D742,534 | S | 11/2015 | Bains |
| D744,663 | S | 12/2015 | Holland |
| 9,237,981 | B1 | 1/2016 | Clementes |
| D750,796 | S | 3/2016 | Bains |
| D750,841 | S | 3/2016 | Lewis |
| D752,237 | S | 3/2016 | Cole et al. |
| D765,872 | S | 9/2016 | Blaskovich et al. |
| D773,682 | S | 12/2016 | Faussett |
| D776,824 | S | 1/2017 | Black |
| D777,939 | S | 1/2017 | Black |
| D785,193 | S | 4/2017 | Cole et al. |
| D790,724 | S | 6/2017 | Black |
| D805,211 | S | 12/2017 | Wu |
| 9,931,003 | B2 | 4/2018 | Sueyoshi et al. |
| D818,588 | S | 5/2018 | Black |
| D818,600 | S | 5/2018 | Black |
| D819,825 | S | 6/2018 | Black |
| D819,826 | S | 6/2018 | Black |
| D825,929 | S | 8/2018 | Julemont |
| D829,445 | S | 10/2018 | Kern et al. |
| D830,568 | S | 10/2018 | Black |
| D834,832 | S | 12/2018 | Kim |
| D841,176 | S | 2/2019 | Gaquiere et al. |
| D842,489 | S | 3/2019 | Spewock et al. |
| D843,002 | S | 3/2019 | Yarborough et al. |
| D844,163 | S | 3/2019 | Du |
| D844,797 | S | 4/2019 | Matsushita |
| D845,002 | S | 4/2019 | Disanti |
| D845,499 | S | 4/2019 | Wersland et al. |
| D845,500 | S | 4/2019 | Wersland et al. |
| D849,260 | S | 5/2019 | Wersland et al. |
| D849,261 | S | 5/2019 | Wersland et al. |
| D849,263 | S | 5/2019 | Soutelo Gomes |
| D850,640 | S | 6/2019 | Wersland et al. |
| D850,641 | S | 6/2019 | Black |
| 10,322,057 | B2 | 6/2019 | Black |
| D853,576 | S | 7/2019 | Ma |
| D855,197 | S | 7/2019 | Park |
| 10,383,486 | B2 | 8/2019 | Nichols |
| D858,786 | S | 9/2019 | Luo et al. |
| D858,789 | S | 9/2019 | Logan |
| D861,182 | S | 9/2019 | Wersland et al. |
| D863,587 | S | 10/2019 | Yee |
| D865,203 | S | 10/2019 | Eschbach et al. |
| 10,426,692 | B2 | 10/2019 | Jurna et al. |
| D868,277 | S | 11/2019 | Yamazaki |
| D869,673 | S | 12/2019 | Chen |
| D873,418 | S | 1/2020 | Scott |
| D874,666 | S | 2/2020 | Matsushita |
| D887,572 | S | 6/2020 | Matsushita |
| D890,353 | S | 7/2020 | Nazarian |
| D890,941 | S | 7/2020 | Gaquiere et al. |
| D890,943 | S | 7/2020 | Wersland et al. |
| D894,414 | S | 8/2020 | Sherrill |
| D895,823 | S | 9/2020 | Khubani et al. |
| D896,393 | S | 9/2020 | Wersland et al. |
| 10,765,199 | B2 | 9/2020 | Kern |
| 10,772,473 | B2 | 9/2020 | Johnstone et al. |
| D901,032 | S | 11/2020 | Gonglach |
| D903,140 | S | 11/2020 | Andrejs |
| D905,262 | S | 12/2020 | Khubani et al. |
| D907,792 | S | 1/2021 | Marton et al. |
| D908,235 | S | 1/2021 | Marton et al. |
| D918,404 | S | 5/2021 | Wersland et al. |
| D918,405 | S | 5/2021 | Wersland et al. |
| D925,128 | S | 7/2021 | Yang et al. |
| 11,110,029 | B2 | 9/2021 | Xie et al. |
| D941,036 | S | 1/2022 | Hinds |
| D945,076 | S | 3/2022 | Zhang |
| D946,166 | S | 3/2022 | Li |
| D949,362 | S | 4/2022 | Zheng |
| D949,365 | S | 4/2022 | Li |
| D949,366 | S | 4/2022 | Li |
| D949,374 | S | 4/2022 | Black |
| D949,380 | S | 4/2022 | Khubani et al. |
| D949,395 | S | 4/2022 | Lee et al. |
| D950,062 | S | 4/2022 | Vuillemin et al. |
| D952,166 | S | 5/2022 | Peluso et al. |
| D952,175 | S | 5/2022 | Zou |
| D953,555 | S | 5/2022 | Lee et al. |
| D954,285 | S | 6/2022 | Lee et al. |
| D956,240 | S | 6/2022 | Mcbrien et al. |
| D956,996 | S | 7/2022 | Costa |
| D961,795 | S | 8/2022 | Zhao et al. |
| D962,556 | S | 8/2022 | Wu |
| D967,978 | S | 10/2022 | Liu |
| D975,045 | S | 1/2023 | Xu |
| D977,667 | S | 2/2023 | Yang |
| D977,842 | S | 2/2023 | Lee |
| D979,087 | S | 2/2023 | Yang |
| D981,578 | S | 3/2023 | Yee |
| D982,356 | S | 4/2023 | Kliegman et al. |
| D984,977 | S | 5/2023 | Sun |
| D985,147 | S | 5/2023 | Zhu |
| D985,786 | S | 5/2023 | Yin |
| D992,131 | S | 7/2023 | Marton |
| D992,132 | S | 7/2023 | Marton |
| D992,135 | S | 7/2023 | Omari et al. |
| D993,437 | S | 7/2023 | Klimov |
| D994,131 | S | 8/2023 | Black |
| D994,132 | S | 8/2023 | Zong |
| D994,140 | S | 8/2023 | Yang |
| D995,808 | S | 8/2023 | Yin |
| D996,065 | S | 8/2023 | Lei et al. |
| D998,149 | S | 9/2023 | Ghoniem |
| D998,160 | S | 9/2023 | Shao |
| D1,003,313 | S | 10/2023 | Lin |
| D1,004,114 | S | 11/2023 | Black |
| D1,005,500 | S | 11/2023 | Yoon et al. |

(56) References Cited

U.S. PATENT DOCUMENTS

D1,005,516 S 11/2023 Leng
D1,005,692 S 11/2023 Russo
D1,006,247 S 11/2023 Qiao
D1,021,989 S 4/2024 Tsushima et al.
D1,038,434 S 8/2024 Krut
2002/0151930 A1 10/2002 Mills
2002/0193715 A1 12/2002 Slack
2003/0158505 A1 8/2003 Calvert
2003/0212353 A1 11/2003 Kahn
2004/0024336 A1 2/2004 Lin
2004/0082449 A1 4/2004 Brown, Jr.
2004/0208683 A1 10/2004 Shawan et al.
2004/0260215 A1 12/2004 Kim
2005/0015030 A1* 1/2005 Bousfield ................. A61N 1/40 601/129
2005/0096572 A1 5/2005 Hua
2005/0101944 A1 5/2005 Williams
2005/0107724 A1 5/2005 Dunmore, Sr.
2005/0137505 A1 6/2005 Munday
2005/0142093 A1 6/2005 Skover et al.
2006/0135323 A1 6/2006 Sjobakk et al.
2006/0253054 A1 11/2006 Wright
2007/0173750 A1 7/2007 Hudock
2007/0179412 A1 8/2007 Imboden et al.
2008/0086066 A1 4/2008 Munday
2008/0119913 A1 5/2008 Powell et al.
2008/0167590 A1 7/2008 Jon et al.
2008/0200849 A1 8/2008 Hollington et al.
2008/0255486 A1 10/2008 Ludlow
2009/0121059 A1 5/2009 Rios Garcia
2009/0204061 A1 8/2009 Pomposelli et al.
2009/0287195 A1 11/2009 Altshuler et al.
2010/0040432 A1 2/2010 Totsu
2010/0160841 A1 6/2010 Wu
2010/0191161 A1 7/2010 Mouatt
2010/0217164 A1 8/2010 Meyer et al.
2010/0274162 A1 10/2010 Evans
2010/0312158 A1 12/2010 Lin
2011/0054369 A1 3/2011 Destefano
2011/0077561 A1 3/2011 Choly
2011/0087140 A1 4/2011 Lee
2011/0144550 A1 6/2011 Suttman
2011/0154690 A1 6/2011 Walsh
2011/0224588 A1 9/2011 Grippo
2012/0016292 A1 1/2012 Goldberg et al.
2012/0109043 A1 5/2012 Zhou et al.
2012/0121313 A1* 5/2012 Thiebaut ................ A61H 7/003 601/136
2012/0167323 A1 7/2012 Williams
2012/0204369 A1 8/2012 Watanabe et al.
2012/0323151 A1 12/2012 Faussett
2013/0023807 A1 1/2013 Hennessey
2013/0046212 A1 2/2013 Nichols
2013/0079689 A1 3/2013 Thierman
2013/0190664 A1 7/2013 Johnson
2013/0197405 A1 8/2013 Williams et al.
2013/0226052 A1 8/2013 Niggemann
2013/0324792 A1 12/2013 Mizrahi et al.
2014/0200495 A1 7/2014 Jones
2014/0243718 A1 8/2014 Black
2014/0272761 A1 9/2014 Lowe et al.
2014/0323993 A1 10/2014 Wilcox et al.
2014/0358045 A1 12/2014 Toto
2015/0135455 A1 5/2015 Reusche et al.
2015/0157414 A1 6/2015 Van Curen
2015/0216292 A1 8/2015 Tweel et al.
2016/0008213 A1 1/2016 Cheng
2016/0099595 A1* 4/2016 Chien ....................... H02J 7/00 362/253
2016/0175185 A1* 6/2016 Buchner Santos .. A61H 23/006 601/113
2016/0206087 A1 7/2016 Skidmore et al.
2017/0073050 A1 3/2017 Smith
2017/0216136 A1 8/2017 Gordon
2017/0333280 A1 11/2017 Black
2017/0348082 A1 12/2017 Ogleby
2018/0161233 A1 6/2018 Nakanishi
2018/0288160 A1* 10/2018 Paul ....................... A61H 7/007
2019/0045912 A1 2/2019 Mikitovic et al.
2019/0045918 A1 2/2019 Przirembel et al.
2019/0216678 A1 7/2019 Yang
2019/0247268 A1 8/2019 Black
2020/0113322 A1* 4/2020 Balestrini ............ A46B 13/008
2021/0100717 A1 4/2021 Beck
2021/0299304 A1* 9/2021 Concannon ............... A61L 2/26
2022/0087893 A1 3/2022 Black
2022/0241136 A1 8/2022 Costa
2023/0010191 A1 1/2023 Black
2023/0200811 A1 6/2023 Black

FOREIGN PATENT DOCUMENTS

CN 2449536 Y 9/2001
CN 102247277 A 11/2011
CN 202802101 U 3/2013
CN 203694035 U 7/2014
CN 203724434 U 7/2014
CN 204484727 U 7/2015
CN 201530461899.2 4/2016
CN 201630416937.7 4/2017
CN 207785468 U 8/2018
CN 208626154 U 3/2019
CN 208770335 U 4/2019
CN 109820708 A 5/2019
CN 209464314 U 10/2019
CN 209864569 U 12/2019
CN 210750164 U 6/2020
CN 211326656 U 8/2020
CN 108430426 B 9/2020
CN 212416317 U 1/2021
CN 112426341 A 3/2021
CN 213373701 U 6/2021
CN 213431541 U 6/2021
CN 214049658 U 8/2021
DE 29710313 U1 8/1997
DE 20 2009 014 825 U1 2/2010
EM 003539014-0001 3/2017
EP 0 811 365 A2 12/1997
EP 2 311 426 A1 4/2011
EP 2 922 518 B1 9/2015
GB 2 331 706 A 6/1999
JP 2002-153531 A 5/2002
JP 6793200 B2 12/2020
KR 100941568 B1 2/2010
KR 300888480 1/2017
RU 2070018 C1 12/1996
RU 2662879 C2 7/2018
RU 2719940 C1 4/2020
TW 201412300 A 4/2014
WO WO-87/00425 1/1987
WO WO-02/083054 A1 10/2002
WO WO-2007/051233 A1 5/2007
WO WO-2008/049165 A2 5/2008
WO WO-2012/009862 A1 1/2012
WO WO-2014/118596 A1 8/2014
WO WO-2017/193054 A1 11/2017

OTHER PUBLICATIONS

Amazon, “FasciaBlaster ProBlaster”, Earliest Review Date: Oct. 14, 2022. https:/www.amazon.com/FasciaBlaster-ProBlaster-Ashley-Black-Discomfort/dp/BOB916ZPYP/ref=cm_cr_arp_d_pl_foot_top?ie=UTF8 (Year: 2022).

Amazon, “Mini Paddle Blaster”, Date First Available: Oct. 27, 2020. https://www.amazon.com/Mini-Paddle Blaster-Cellulite-FasciaBlaster/dp/B08LZR7GWW/ref=cm_cr_arp_d_project_top?ie=UTF8 (Year: 2020).

Amazon, “Savage Blaster” by Ashley Black, Earliest Review Date: Feb. 24, 2022. https://www.amazoon.com/FasciaBlaster-SavageBlaster-Ashley-Black-Discomfort/dp/B09KM8MWX3/ref=cm_cr_arp_d_pl_foot_top?ie=UTF8 (Year: 2022).

(56) References Cited

OTHER PUBLICATIONS

Amazon, "FasciaBlaster Trigger Point Tools", Nov. 6, 2017, https://www.amazon.com/Mini-Blaster-Ashley-Black-Guru/dp/B075M26CJT/ref=cm_cr_arp_d_pl_foot_top?ie=UTF8. Shown on p. 1. (Year: 2017).
Amazon, "Mini Paddle Blaster", Apr. 8, 2021. https://www.amazon.com/Mini-Paddle-Blaster-Cellulite-FasciaBlaster/dp/B08LZR7GWW/ref=sr_1_2?dchild=1&keywords-Ashley+Black+Guru&qid=1617887539&sr=8-2. Shown on p. 1. (Year: 2021).
Amazon, "Trigger Point Massager Massage Tool", Jan. 18, 2019. https://www.amazon.com/Trigger-Point-Massage-Tool/dp/B075FXVB39/ref=cm_cr_arp_d_product_top?ie=UTF8. Shown on p. 1. (Year: 2019).
Ashley Blacks, "Mini Paddleblaster1", Aug. 21, 2020. https://www.ashleyblackguru.com/products/mini-paddleblaster-1#shopify-product-reviews. Shown on p. 1. (Year: 2020).
Ashleyblackguru, "Ashley Black Mini Paddleblaster", Earliest review Date: Aug. 21, 2020. https://www.ashleyblackguru.com/product/mini-paddleblaster (Year: 2020).
Ashleyblackguru, "Problaster", Earliest Review Date: Aug. 9, 2022. https:/Avww.ashleyblackguru.com/collections/all/products/problaster (Year: 2022).
Ashleyblackguru, "Savage Blaster", Earliest Review Date: Nov. 12, 2021. https://www.ashleyblackguru.com/collections/body-tools/products/savage-blaster#shopify-product-reviews (Year: 2021).
Ashleyblackguru, "Mini 2", Nov. 12, 2017, https://www.ashleyblackguru.com/products/mini-2#shopify-product-reviews. Shown on p. 1. (Year: 2017).
Communication pursuant to Rules 161 (1) and 162 EPC for corresponding EP Application No. 14709121.9, mailed Oct. 6, 2015, 2 pages.
D'arsonval High Frequency Device Skin Tightening Spot Wrinkles Remover Acne Treatment, www.topbeautybuy.com, 2017, 6 pages.
Definition of the term "Circular", Miriamwebster.com, captured on Feb. 1, 2024.
European Pat. Appl. No. 14709121.9, Communication dated Feb. 9, 2021, 6 pages.
Examination Report for corresponding EP Application No. 14709121.9, mailed Dec. 7, 2017, 5 pages.
International Preliminary Report on Patentability for corresponding PCT/US2014/018043, mailed Aug. 25, 2015, 6 pages.
International Preliminary Report on Patentability for corresponding PCT/US2017/031384, mailed Nov. 6, 2018, 6 pages.
International Search Report and Written Opinion for corresponding PCT/US2014/018043, mailed May 6, 2014, 10 pages.
International Search Report and Written Opinion for corresponding PCT/US2017/031384, mailed Sep. 14, 2017, 9 pages.
International Search Report and Written Opinion on PCT/US2022/052052 dated Mar. 10, 2023, 12 pps.
IPRP, Foreign Action other than Search Report on PCT DTD Jun. 20, 2024.
Notice of Allowance on U.S. Appl. No. 29/799,043 DTD Mar. 22, 2023.
Octopus-Shaped Massager (Octopus), Sales Pgs Dated 2006-2011, Retrieved from: https://web.archive.org/web/20060514183134/http://www.chinatraderonline.com/Files/Health-2Beauty/Beauty-Equipment/Octopus-Massager-13342022084.jpg, 1 pg.
Vola Massager, Wayback Machine Jan. 17, 2008 capture of http://www.chinatraderonline.com/Massager/VOLA-MASSAGER-193802857.htm, retrieved from https://web.archive.org/web/20080117105426/http:/www.chinatraderonline.com/Massager/VOLA-MASSAGER-193802857.htm, Jul. 19, 2021, 1 pg.
Youtube, "Discover the SavageBlaster", Published Date: Jul. 22, 2022I https://www.youtube.com/watch?v=uBxEX3waWSk (Year 2022).
Youtube, "How to Select the Right Fascia Blaster for You", Published Date: Nov. 27, 2020. https://www.youtube.com/watch?v=bQojqSYrhwQ (Year: 2020).
Youtube, "Mini1 Paddleblaster", Oct. 9, 2020. https://www.youtube.com/watch?v=LIK17dCevBQ. Shown at the 0:02 second mark. (Year: 2020).

* cited by examiner

CELLULITE LEG

ACNE FACE

SHOULDER SCAR

POSTURE BACK

BUTT

HAIR
Remodeling the scalp fascia creates new and better follicles

NECK
Remodeling fascia allows the ECM to restructure tightening neck skin

POST STROKE PARALYSIS
Remodeling fascia stimulates Neuro-logical connectivity

SYSTEM AND METHOD FOR PERFORMING TISSUE TREATMENT USING POWERED TREATMENT DEVICES

CROSS-REFERENCE TO RELATED APPLICATIONS

This application claims priority to, and the benefit of, U.S. Provisional Patent Application Ser. No. 63/286,536 entitled "SYSTEM AND METHOD FOR PERFORMING TISSUE TREATMENT USING POWERED TREATMENT DEVICES" filed on Dec. 6, 2021, the contents of which are hereby incorporated herein by reference in their entirety for any purpose.

BACKGROUND

Fascia tissue is a layer of fibrous tissue that operates as a connective tissue that surrounds muscles, groups of muscles, nerves, blood vessels, etc. The tissue allows for proper functioning of muscles with respect to one another (e.g., sliding past one another). When fascia tissue becomes damaged through injury, tissue knots, adhesions in the fascia tissue, medical reasons, or otherwise, the fascia tissue can take time to correct itself or require manipulation to release the fascia tissue and allow for proper functioning of the tissue to allow the underlying muscle to properly operate. In some cases, the fascia tissue can be released or corrected without much difficulty, while in other cases, restoring the fascia tissue to its proper form can take considerably more effort. Other reasons for releasing fascia tissue may include cosmetic reasons, especially for people who have dimpled skin, which is often caused by fascia tissue extending through fat cells, thus causing dimples to appear on the skin. Often, when the fascia tissue is properly released, the dimples can be considerably reduced or eliminated.

SUMMARY

A fascia tissue treatment system may include a base station that powers tissue treatment devices that are used to treat fascia or other tissue of patients. The tissue treatment devices may be powered devices, and include actuators that are used to move tissue treatment elements. The actuators may be motors that cause an effector inclusive of a support structure, such as a disc or other shaped structural member, on which the tissue treatment elements are connected or formed. In an embodiment, the effector may be a unitary piece, where a support structure and protrusions or fingers extend. Alternatively, the fingers may be detachably coupled to the support structure. The fingers may have a base that connects to or is integrated with the support structure, curved shafts, and rounded tips.

In operation, base station may be utilized to provide electrical power (or other power source types) to provide tissue treatment functions, such as warm-up, tissue release, and/or tissue treatment. The base station may support (i) a heater, such as an infrared heater element, to warm up tissue of a patient, (ii) an ultrasound and/or radio frequency (RF) device to provide for tissue release, and tissue treatment devices of different configurations to provide for fascia or other tissue treatment.

Moreover, the tissue treatment device may receive electrical power that drives a rotating motor therein. The motor may cause the effector to spin. An operator, either a medical professional or a patient him or herself, may engage the tissue treatment device to cause the effector to spin while pressing the effector onto a patient's skin. The amount of force being applied may vary depending on a modality being performed along with a particular location on the patient's body being treated. For example, treatment to a face or scalp uses much less force than body parts with larger surface area and more dense tissue (e.g., muscle). Moreover, if fascia tissue being treated is causing acute pain, then less force and, possibly, less speed of the rotating effector may be used. It should be understood that a wide variety of treatment protocols may be utilized. Moreover, although a spinning effector may be utilized, other actuator types and effectors may be utilized. For example, motors that cause an effector, such as a square or rectangular effector, to cause the effector to move linearly (e.g., forward and backward along a single axis). Powered tissue treatment devices may be utilized, as well, and have a variety of different controllers.

The base station may further include an electronic device, such as a tablet, that may be used to manage operators, patients, treatment plans, collect data, and/or control operations of the tissue treatment device(s). In an embodiment, the base station may further be configured with an ultrasound scanning device and optionally camera device that enables an operator to perform ultrasound scanning on tissue of a patient and record the scans to aid the operator know the type of treatment that the patient in that region should have. The computing device may capture the ultrasound images and/or visual images and store those images for later viewing. Additionally, the computing device may compare the images over time to assist an operator in determining how past treatments have resulted in improving tissue of the patient. In an embodiment, artificial intelligence (AI) software may be utilized to identify fascia tissue or other tissue abnormalities or structural issues to aid an operator understand how treatments are to be made. In an embodiment, the computing device may be configured to recognize certain structural issues with fascia tissue and aid or recommend to an operator or other medical professional in creating a treatment plan.

BRIEF DESCRIPTION

A more complete understanding of the method and apparatus of the present invention may be obtained by reference to the following Detailed Description when taken in conjunction with the accompanying Drawings wherein.

DETAILED DESCRIPTION OF THE DRAWINGS

Figure 2:
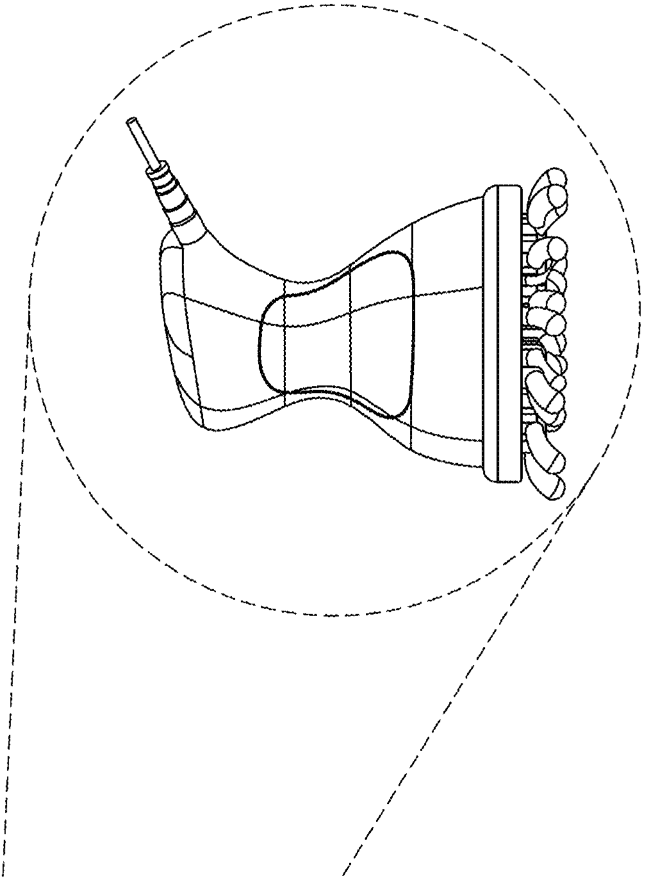
FIG. 2 is an illustration of a fascia tissue fitness device of the illustrative therapy system of FIG. 1.

Existing fascia tissue treatment devices require manual manipulation by a user to move tissue treatment elements across a patient's skin. While effective, users performing self-treatment using hand-held tools may not use sufficient force and/or speed to ensure adequate treatment of the fascia tissue. Conventional motorized scalp or tissue massagers are not designed to release fascia tissue. For example, the messaging and/or brush elements employed by these conventional systems are specifically designed for user comfort and skin surface treatment, but are not suitable for working the underlying tissue in a manner meant to improve fascia tissue fitness to perform restructuring of fascia tissue at different layers starting at the skin and working down towards or even to the bone. Additionally, fascia tissue treatment may utilize considerable application of force between the tissue treatment elements and a person or patient's skin, which may cause stress to an actuator being used to drive the tissue treatment elements, thereby resulting in premature failure of the actuator. Such stress, for example, may be caused by using forces in treating fascia tissue that higher torque has to be produced by the actuator, which may result in heat produced in the actuator due to high current draw therein. As such, various configurations of actuators and tissue treatment elements may be utilized to avoid such high-torque situations. It should be understood that the fascia tissue treatments are meant to be applied to lubricated skin of a patient, where the lubrication may be any fluid, such as oil, applied to the skin that reduces friction between tissue treatment elements, such as protrusions (e.g., fingers), of an effector of the tissue treatment device. Alternatively, a cover, such as a sleeve formed of a slick external material, may be placed on skin of a user to enable the tissue treatment device to be applied to the cover to avoid or use a minimal amount of lubrication.

Referring to the Figures generally, a fascia tissue therapy system is shown that addresses the foregoing issues and provides an all-in-one system for diagnosing and treating damage to fascia tissue. The therapy system includes a base station and a therapy device inclusive of an actuator and tissue treatment element that is actuated (e.g., rotated, vibrated, etc.) by the actuator. The tissue treatment element may form part of an effector that is detachably coupled to the base station. The base station may be configured in a number of ways, including (i) operating as a cabinet with actuated heads that control operation of an effector with tissue treatment elements, (ii) operating a computing device to help monitor and manage treatment sessions of patients by an operator of the therapy system, and (iii) operating a computing device that includes a control system for the therapy system that is configured to (a) determine a tissue condition based on data received from the therapy device (e.g., sensors onboard the therapy device, etc.), (b) determine a treatment regimen based on the condition, and (c) control and monitor operation of the therapy device to treat the condition.

Because the fascia tissue therapy system may support different types of treatment devices, such as radio frequency (RF) treatment device(s), ultrasonic cavitation treatment device(s), and fascia tissue treatment device(s), different power types and levels may be utilized for each of the treatment devices. As such, the system may be configured to supply different power types and/or levels to support each of the different devices, and be configured to manually, semi-automatically, or automatically set a different power type and/or level or include different power sources for such support. The different power types and/or levels may be controlled by mechanical, electrical, and/or software and/or hardware (e.g., mechanical switch or other selector) by an operator, for example. In an embodiment, electronics may be utilized to condition power for the different types and/or levels. For example, if three different power types (e.g., DC 100 v, AC 120 v/1-phase, AC 208 v/3-phase) as to be used to support three different treatment devices, the electronics that supply power each of those type types to one or more outlets at the base station into which an operator may plug the treatment devices.

In an embodiment, the computing system may also be configured to track treatment progress and re-evaluate the tissue condition at periodic (e.g., during periodic treatments) or aperiodic (e.g., during non-periodic treatments) intervals. The therapy device may be designed to monitor and treat damage to fascia tissue or otherwise manipulate and restore fascia tissue. The therapy device may include a direct drive motor and an effector that is detachably coupled to the therapy device and powered into rotation (or otherwise) by the direct drive motor. Unlike existing powered devices, which typically use a transmission (e.g., gear, gear set, etc.) to achieve the high speeds required for operation, the direct drive motor of the present disclosure may be coupled to the effector without an intervening transmission or gear set. Using a direct drive motor may reduce heat generation and wear on the treatment device as compared to a typical motor that utilizes a gear box, thereby allowing use of the device over longer treatment intervals and with less risk of changes in performance during treatment. The high weight to torque ratio of the direct drive motor may also reduce the weight of the therapy device.

The effector for the treatment device may be structured to engage a patient's skin and manipulate the fascia tissue to restore and restructure the fascia tissue to its proper form. As described herein, the system may be used to treat the fascia tissue at different levels (e.g., shallow, medium depth, deep) depending on the modality and location of the patient (e.g., face may be shallow, arm may range from shallow to medium, leg may range from shallow to deep). The effector may include a panel and/or plate that is detachably coupled to the treatment device and that includes multiple tissue treatment elements. In some embodiments, the panel may include a mount at an intermediate radial position along the panel that connects the panel to the treatment device to reduce a torque required to maintain movement of the panel during operation. The panel may also include supports and/or be shaped to ensure uniform contact between the tissue treatment elements and the patient's skin across the face of the panel. The tissue treatment elements may include a plurality of rigid (e.g., inflexible, stiff, not easily bent, etc.) protrusions (e.g., fingers and/or finger members) that extend axially away from the panel. The fingers may extend away from the panel at an angle (e.g., along a direction of rotation of the effector) to improve treatment efficacy and/or allow different treatment modalities depending on the rotational direction of the effector. In contrast to motorized scalp and tissue massagers, the effectors of the present application may be specifically structured to manipulate fascia tissue layers below the skin surface. In an embodiment, the panel may be flat, round, and have the protrusions e.g., tissue treatment elements) on one side of the panel. In another embodiment, the panel may be curved or rounded (e.g., parabolic) from a base portion to a tip with the tissue treatment elements connected to and radially extending therefrom. The tissue treatment elements may have a variety of different shapes, sizes, orientations, alignments, and/or configurations. In one embodiment, the tissue treatment elements (e.g., fingers) may have multiple different sized fingers (e.g., small in the middle and large on the outside of the panel having a flat, circular shape).

Figure 1:
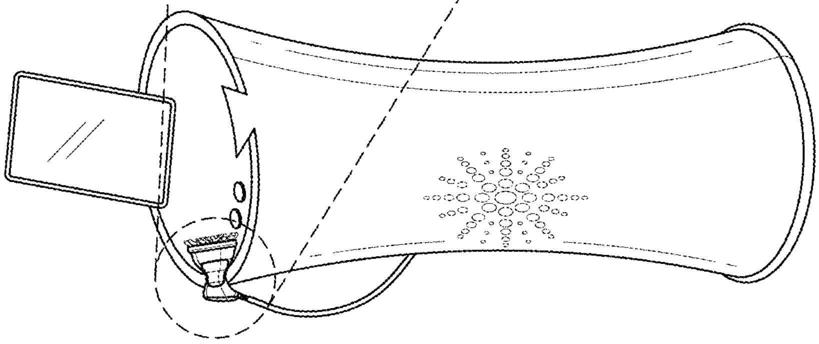
FIG. 1 is an illustration of a front isometric view of an illustrative fascia tissue therapy system.

Referring to FIG. 1, an illustrative fascia tissue therapy system is shown. The system includes a base station (e.g., cabinet, power source(s), computer, communications equipment, etc.) that is configured to house and/or support various equipment, such as fascia tissue treatment device(s), RF treatment device(s), ultrasound device(s), a computing system, one or more powered fascia tissue treatment devices, and/or other system components. In the embodiment of FIG. 1, the base station includes an enclosure defining an interior cavity that is sized to store multiple fascia tissue treatment devices, tissue treatment assemblies, and/or tissue treatment elements therein. The base station may also include a set of wheels (e.g., casters, rollers, etc.) mounted to a bottom or lower wall of the enclosure to facilitate movement of the base station. The wheels may be rotatably coupled to the base station and may include locks to allow a user to prevent rotation of the wheels once the base station has been moved to a desired location. The number and/or arrangement of wheels may be different in other embodiments.

As shown in FIG. 1, the base station includes at least one mount configured to support at least one fascia treatment device in position on the base station. The mount may include a rack that detachably couple or otherwise support the treatment device to the enclosure. In the embodiment of FIG. 1, the mount may include multiple slots (e.g., recessed areas, depressions, etc.) disposed along an outer perimeter of an upper wall or sidewalls of the enclosure. The slots may be sized and configured to receive a handle and/or head portion of the treatment device therein to support the treatment device alone the upper end of the base station. In the embodiment of FIG. 1, the handle hangs on an outer wall of the slot and is secured in position by gravity acting on the treatment device. In other embodiments, the mount may include other types of hangers and/or cradles. In yet other embodiments, the mount may include magnets, hook and loop fasteners, and/or another form of detachable coupling to secure the treatment device to the enclosure when not in use.

FIG. 2 shows an illustrative fascia tissue treatment device (e.g., head, etc.) for the system of FIG. 1. As shown in FIGS. 1-2, the treatment device is electrically coupled to the base station (e.g., a power source that is disposed within the base station) via a tether (e.g., electric cable, etc.) that is coupled to and extends away from the enclosure. The tether also includes electrical connections to power the treatment device and to transmit signals between sensors of the treatment device and the computing system. In at least one embodiment, the treatment device is detachably coupled to the tether so that the same tether can be used to power multiple different treatment devices depending on the desired modality. In an embodiment, all fascia tissue treatment devices may be configured to utilize the same power signals, thereby enabling the system to include a single power cord to which different tissue treatment devices may connect. Alternatively, different tissue treatment devices may be configured to utilized different electrical signals such that different adapters, power cords, sockets, etc. may be used for the different fascia tissue treatment devices.

Figure 5:
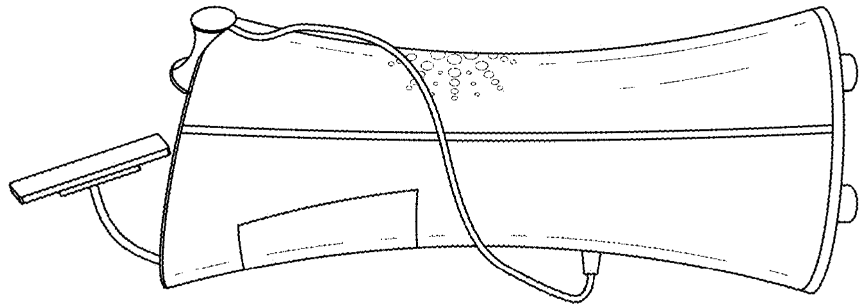
FIG. 5 is a front view of the illustrative fascia tissue therapy system of FIG. 1.
Figure 4:
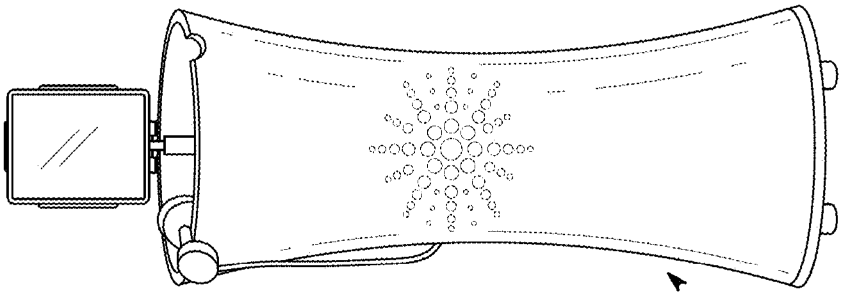
FIG. 4 is a side view of the illustrative fascia tissue therapy system of FIG. 1.
Figure 3:
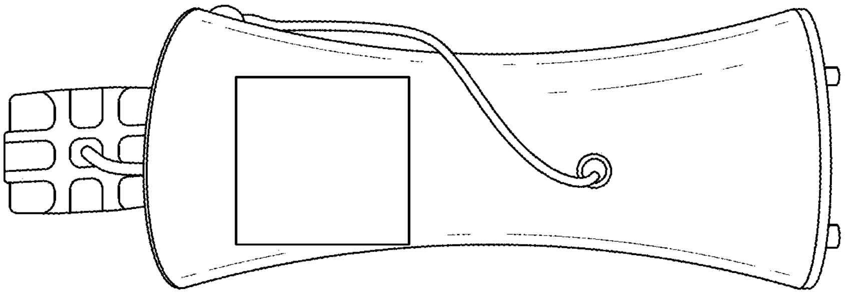
FIG. 3 is a rear view of the illustrative fascia tissue therapy system of FIG. 1.
Figure 7:
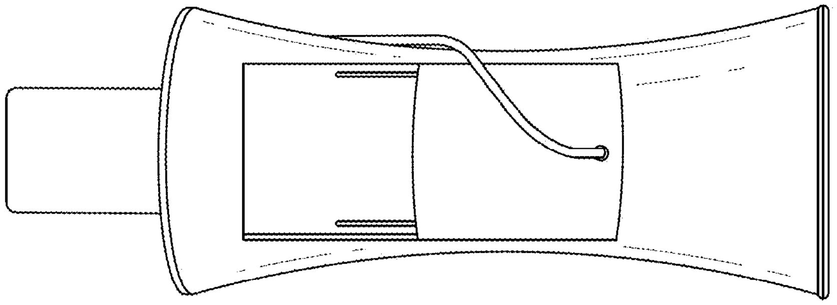
FIG. 7 is a rear view of the illustrative fascia tissue therapy system of FIG. 1 shown with an access panel in an opened position.
Figure 6:
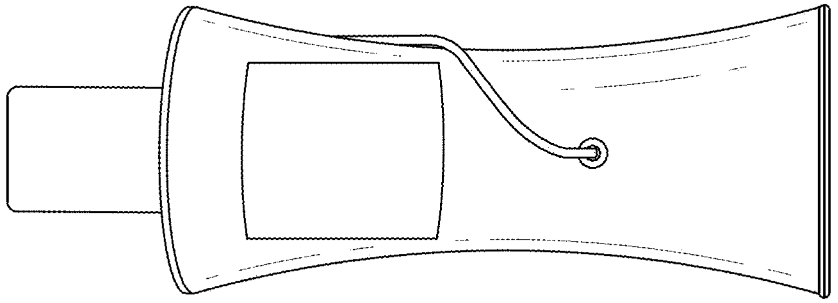
FIG. 6 is a rear view of the illustrative fascia tissue therapy system of FIG. 1 shown with an access panel in a closed position.
Figure 10:
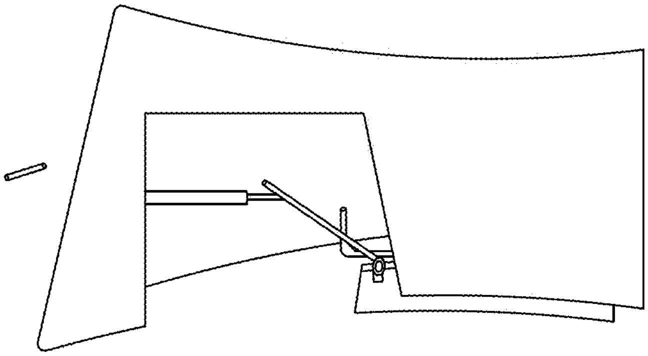
FIG. 10 is a side partial view of the illustrative fascia tissue therapy system of FIG. 1 shown with an access panel in a fully open position.
Figure 9:
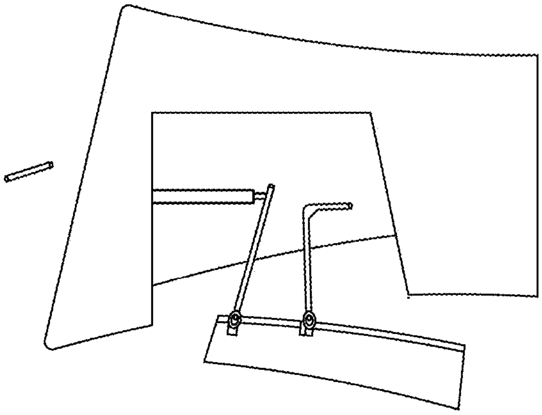
FIG. 9 is a side partial view of the illustrative fascia tissue therapy system of FIG. 1 shown with an access panel in a partially open position.
Figure 8:
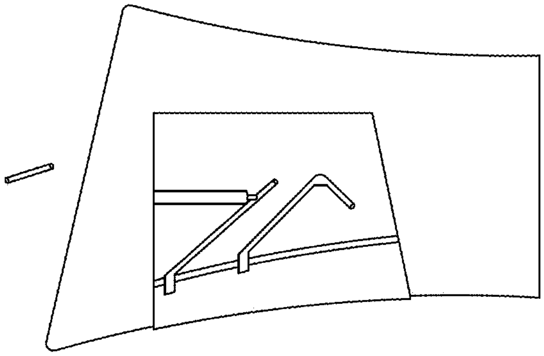
FIG. 8 is a side partial view of the illustrative fascia tissue therapy system of FIG. 1 shown with an access panel in a closed position.

Referring to FIGS. 3-5, rear, side, and front views, respectively, of the illustrative treatment device of FIG. 1 are shown. The enclosure includes an access panel (e.g., door, etc.) coupled to the enclosure along a rear side of the enclosure. The access panel is movable between an open and closed position to selectively provide access to the interior cavity of the enclosure. FIGS. 6-10 show various views of the illustrative treatment device of FIG. 1 with the access panel in different positions. As shown in FIGS. 8-10, the access panel includes a pivot system that allows the panel to translate away from (e.g., radially away from) and pivot with respect to the enclosure. It should be understood that a variety of configurations for opening and closing the access panel may be utilized, including sliding open and close within a concealed wall. The pivot system may include a shock absorber to stabilize the supports for the panel and facilitate movement between an open and closed position. In some embodiments, the pivot system may be configured to automatically reposition the panel in response to user commands from the computing system.

Figure 12:
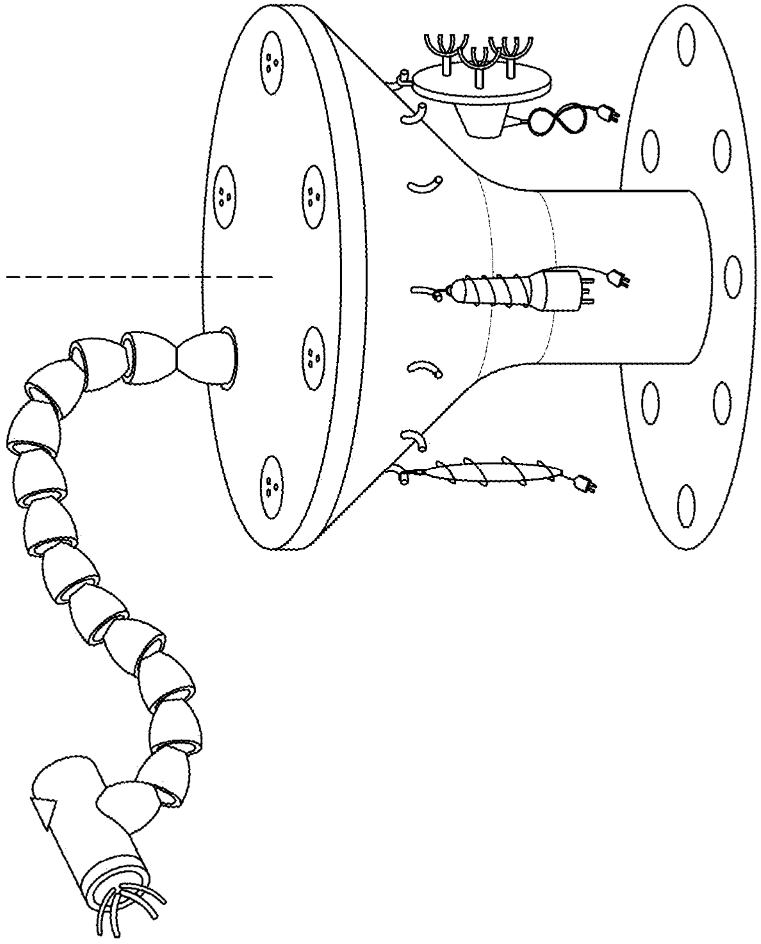
FIG. 12 is an illustration of a front isometric view of another illustrative carousel for a fascia tissue therapy system.
Figure 11:
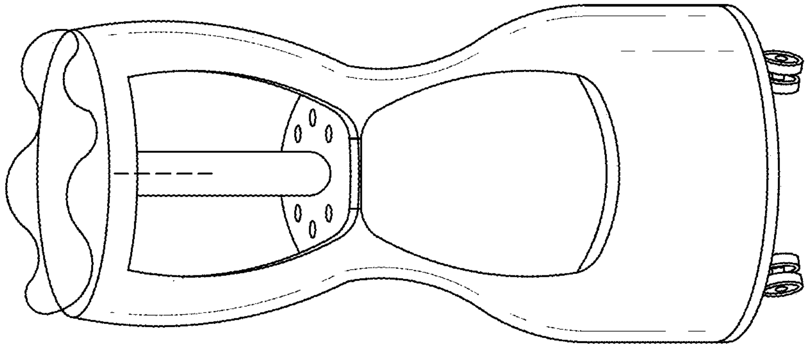
FIG. 11 is an illustration of a front isometric view of another illustrative fascia tissue therapy system.
Figure 14:
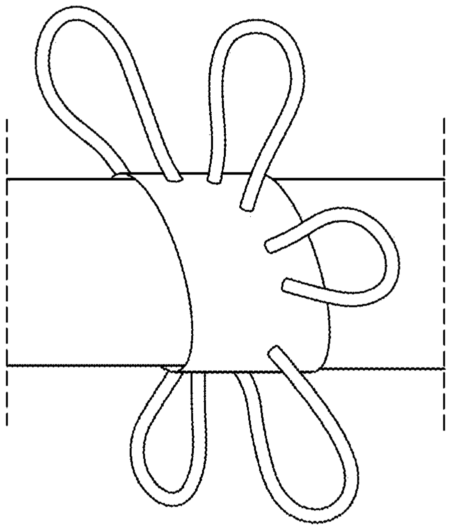
FIG. 14 is an illustration of a front isometric view of another illustrative carousel for a fascia tissue therapy system.
Figure 13:
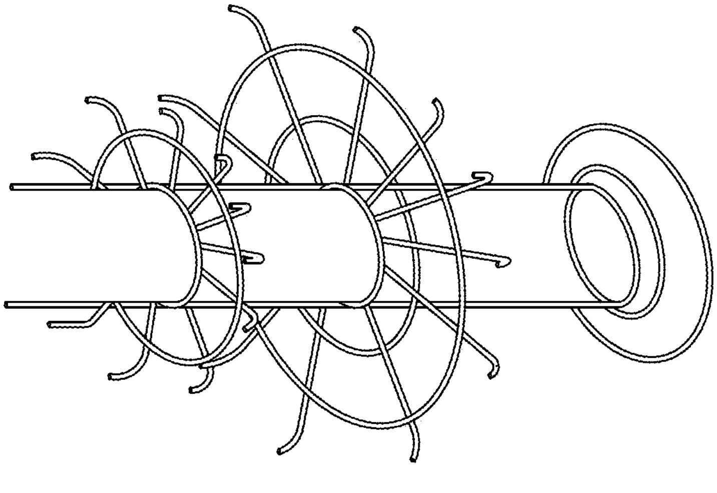
FIG. 13 is an illustration of a front isometric view of an illustrative carousel for a fascia tissue therapy system.
Figure 15:
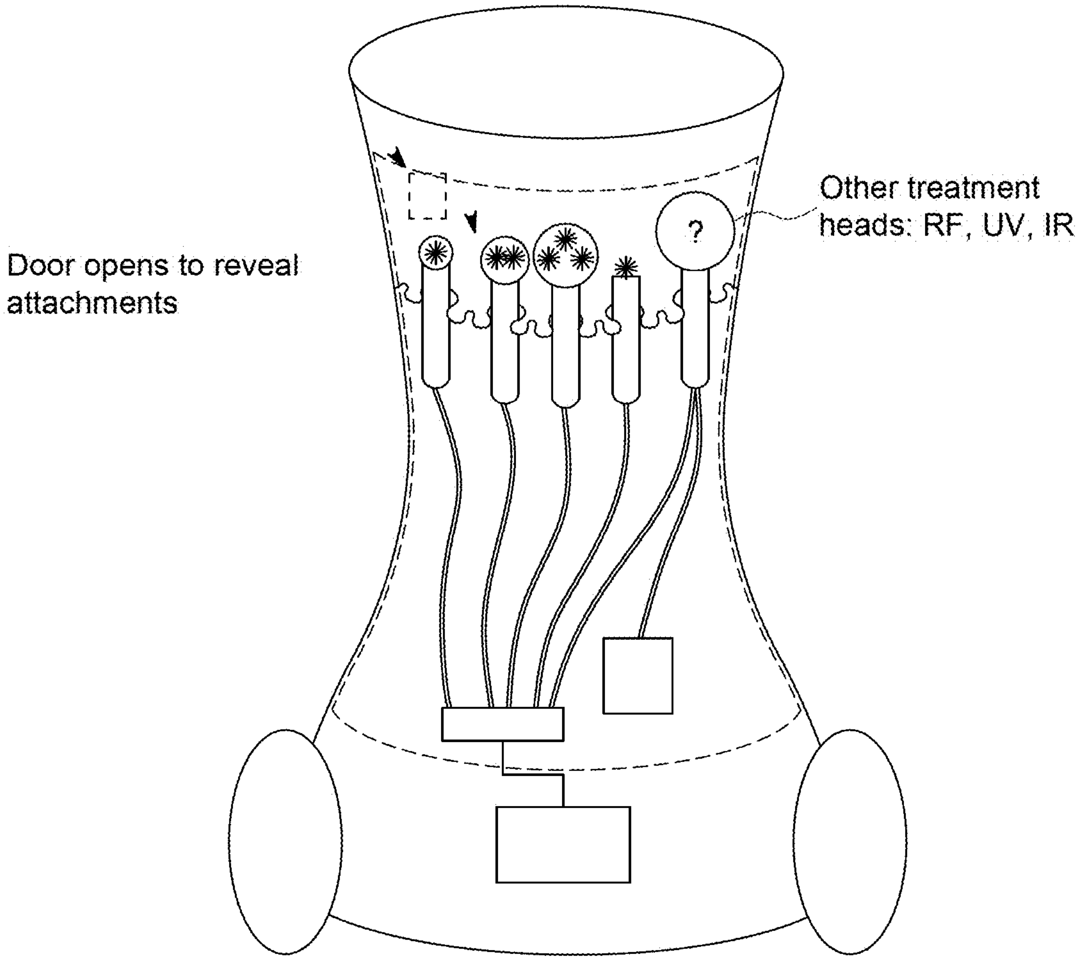
FIG. 15 is an illustration of a rear view of another illustrative fascia tissue therapy system.

In some embodiments, the system is structured to store treatment devices, tissue treatment assemblies, and/or tissue treatment elements therein. For example, FIG. 11 shows an illustration of a rear perspective view of another illustrative fascia tissue therapy system that includes a rotating carousel. As shown in FIG. 12, the rotating carousel is disposed within the interior cavity of the enclosure and is rotatably coupled to the enclosure. The access panel is moveably coupled to the enclosure and can rotate away from the enclosure to provide access to the carousel. The carousel may include a plurality of mounts arranged circumferentially about a rotational axis of the carousel. The mounts are engageable with the treatment device, tissue treatment assemblies, tissue treatment element, and/or other add-ons for the therapy system. The mounts may include hangers, magnets, and/or other detachable couplings to support any add-on equipment for the system. For example, FIG. 13 shows an illustration of a carousel that includes wire hangers and shelving to support various add-ons. FIG. 14 shows a carousel that includes a plurality of loops extending radially away from a central sleeve. It will be appreciated that the design of the carousel may be different in other embodiments. For example, FIG. 15 shows an enclosure that includes a straight rack of hangers that are fixedly coupled to the enclosure. As shown in FIG. 15, the rack of hangers is arranged along a single linear row within the interior cavity of the enclosure. Outlet(s) to power source(s) may be disposed within the enclosure and be easily accessible to plugs of cables for the treatment devices to be plugged into to draw power for operation thereby. In an embodiment, the outlet(s) may be rotatable on the carousel.

It will be appreciated that different mounts may be used to store different types of equipment within or external to the enclosure. The mounts may be arranged at different positions within the interior cavity and/or along the carousel depending on the type of equipment that they support (e.g., at different axial and/or radial positions along the carousel, etc.). A user may rotate the carousel within the interior cavity and select the piece of equipment that they would like to use. Beneficially, using a rotatable carousel to store treatment devices and add-ons improves space utilization of the interior cavity.

In the embodiment of FIGS. 11 and 12, the carousel defines an upper wall of the enclosure that is accessible from an upper end of the enclosure. The carousel includes a plurality of electrical connectors along the upper wall that are engageable with the tether for the treatment device(s). As such, rotation of the carousel will also rotate external features of the base station (e.g., the upper wall). In other embodiments, as shown in at least FIGS. 1-5, the position of the electrical connection between the tether and the base station may be different (e.g., the tether may connect to the base station at a lower, rear end of the enclosure, etc.).

As shown in FIG. 15, a user may store the treatment device in the interior cavity when not in use to improve the overall aesthetic of the system. In some embodiments, the base station may further include a motor coupled to the carousel and structured to rotate the carousel in response to user commands (e.g., signals from a control interface of the base station, push-button, etc.). In an embodiment, rather than using a carousel, the mounts may be positioned on the walls of the interior of the enclosure.

In some embodiments, the base station also includes a sterilization system configured to sterilize treatment devices, tissue treatment elements, and/or other equipment. The sterilization system may include an ultraviolet (UV) light source including one or more UV lights disposed within the interior cavity and configured to expose or "flood" equipment mounted to the carousel with UV light for a threshold period after the access panel has been closed. In an embodiment, the UV light may be controlled by a push-button, via a user interface of a computing device, automatically turned on when the system is not in use (e.g., overnight), or automatically when the access panel is closed (monitored by a switch, for example). Alternatively, or in combination, the sterilization system may include a dispensing system (e.g., nozzle, pump, etc.) disposed within the interior cavity and configured to distribute a sterilization agent over the equipment placed within a container (e.g., mounted to the floor or wall) of the sterilization system, where a portion of a treatment device may be place into the container) within the interior cavity in response to a signal indicating that the access panel has been closed, and/or a signal indicating that treatment has concluded. In some embodiments, the dispensing device can be used to fully wash the equipment placed into the container and stored within the enclosure. In an embodiment, multiple wash cycles (e.g., a sterilization cycle, a rinse cycle, etc.) may be performed on the effectors and possibly other components.

The dispensing system may include an interchangeable fluid reservoir (see FIG. 15) that stores liquids (e.g., sterilizing agents, heat absorbing agents, lubricating agents, etc.) that are used with the therapy system and from which one or more pumps supply fluid to the nozzles. The dispensing system may also be configured to pre-treat surfaces of the effectors and/or therapy devices with lubricants (e.g., oils) or other liquids. The reservoir may be detachably coupled to the enclosure and may be replaced when the liquid supply drops below threshold levels. The sterilization system may further include fans, blowers, and/or heating elements to dry off the tissue treatment devices at the end of a wash cycle. In other embodiments, the enclosure may define a second cavity—separate from the storage area of the internal cavity—that is used to sterilize the tissue treatment devices and other add-on equipment after use. The sterilization system may be affixed to an inner surface or structure within the internal cavity. The sterilization may have a door positioned on top and/or side, and enable an operator to place effector(s) within the sterilization system. As previously described, the sterilization may include fluid that may be sprayed onto the effector(s) and/or other components placed therein, and automatically perform a sterilization cycle (e.g., spray/soak, rinse, rinse, dry, illuminate with UV lights to disinfect the effort(s)).

Returning to FIG. 1, the computing device may be configured to monitor and manage treatment sessions of patients by an operator of the therapy system, and/or may include a control system configured to control operation of the fascia tissue treatment device(s). The computing device may include a controller having a processor and memory storing software for the system for supporting patient treatments (e.g., different treatment regimens, patient data received from sensors, such as pressure sensor(s), speed sensor, torque sensor, temperature sensor(s), etc., onboard the treatment device and/or the user interface, etc.). The computing device may include a user interface coupled to the base station, to receive user commands and display treatment and/or operating information for the therapy system. For example, the computing device may include a tablet (e.g., iPad, etc.) and/or another input/output that is detachably coupled to the base station.

Figure 17:
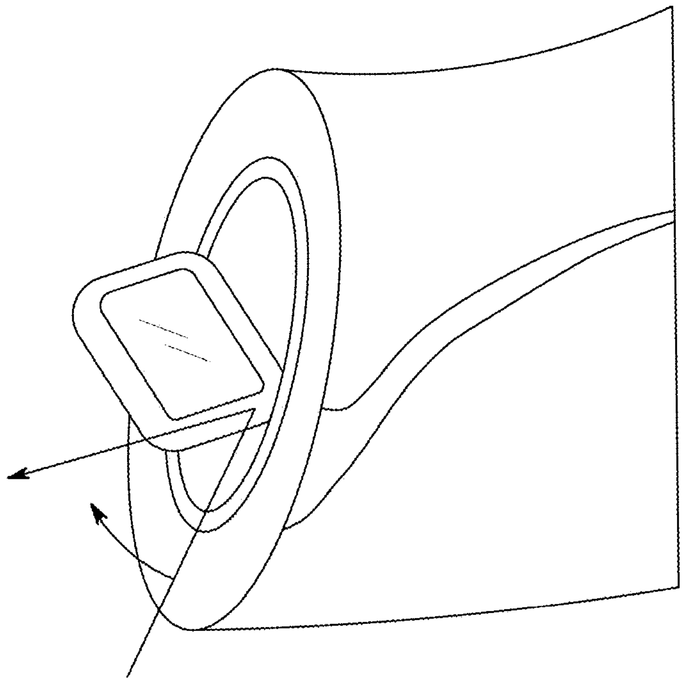
FIG. 17 is another illustration of a side isometric view of the display mount portion of FIG. 16.
Figure 16:
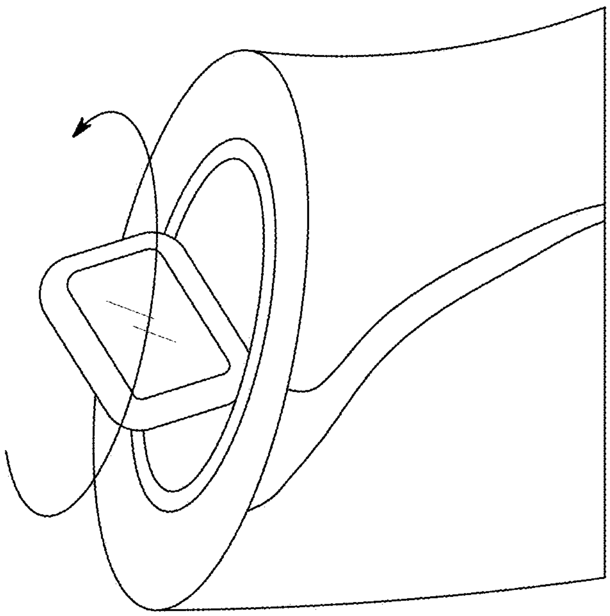
FIG. 16 is an illustration of a side isometric view of a display mount portion of an illustrative fascia tissue therapy system.
Figure 19:
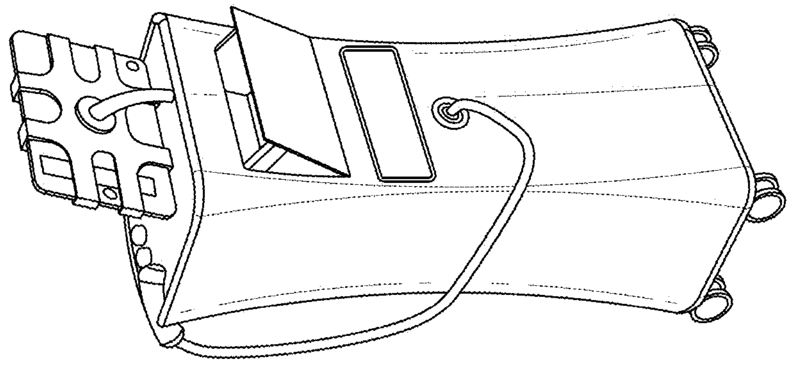
FIG. 19 is a rear view of the illustrative therapy system of FIG. 18.
Figure 18:
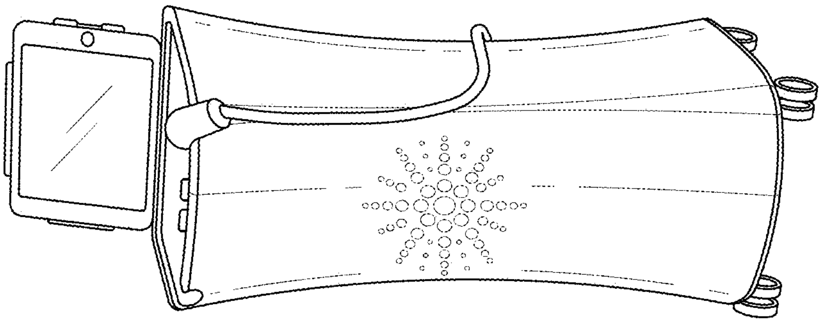
FIG. 18 is an illustration of a front isometric view of another illustrative fascia tissue therapy system.
Figure 21:
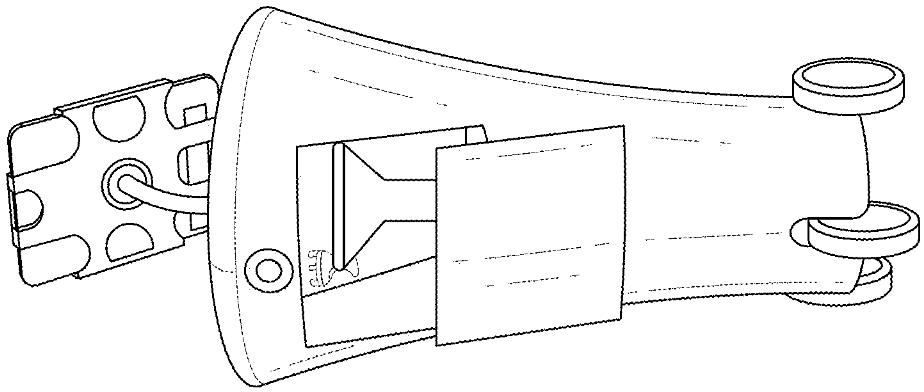
FIG. 21 is a rear view of the illustrative therapy system of FIG. 20.
Figure 20:
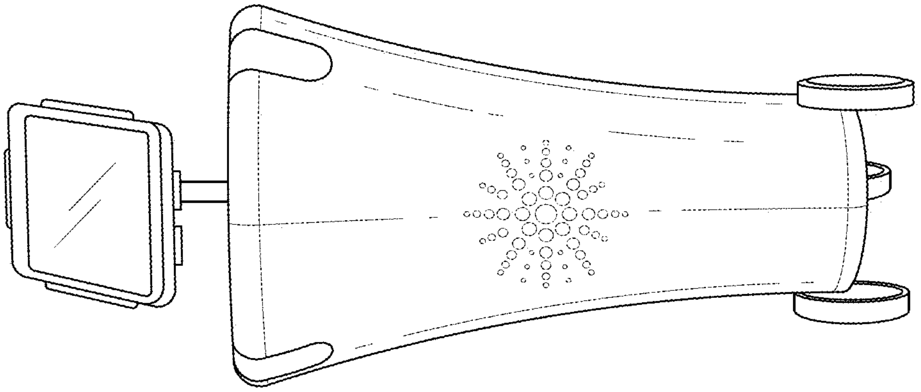
FIG. 20 is an illustration of a front isometric view of yet another illustrative fascia tissue therapy system.
Figure 22:
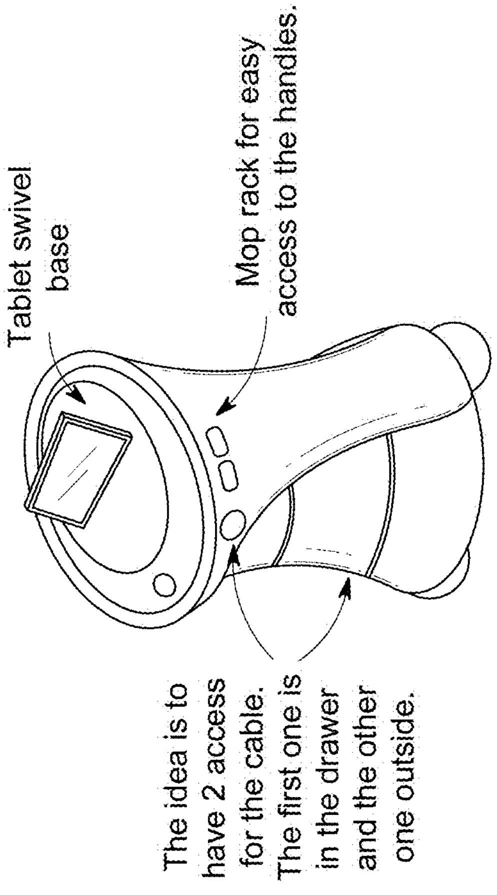
FIG. 22 is an illustration of a front isometric view of yet another illustrative fascia tissue therapy system.
Figure 23:
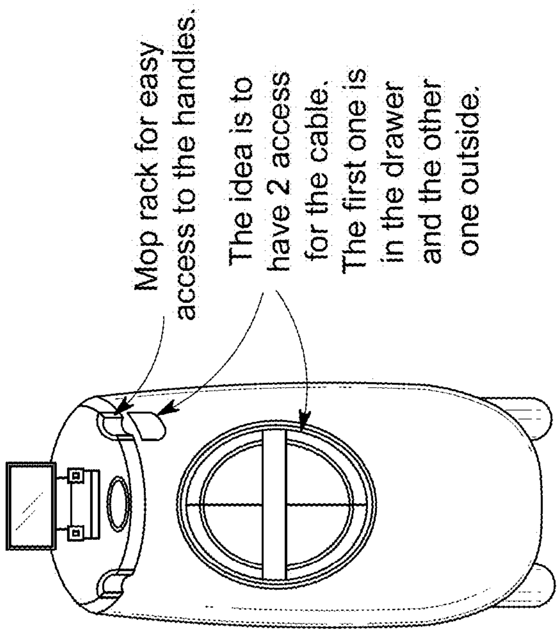
FIG. 23 is an illustration of a front isometric view of yet another illustrative fascia tissue therapy system.
Figure 25:
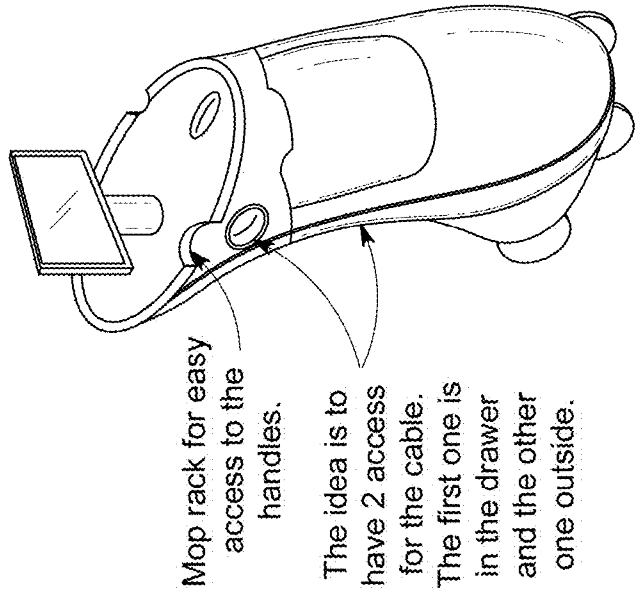
FIG. 25 is an illustration of a front isometric view of yet another illustrative fascia tissue therapy system.
Figure 24:
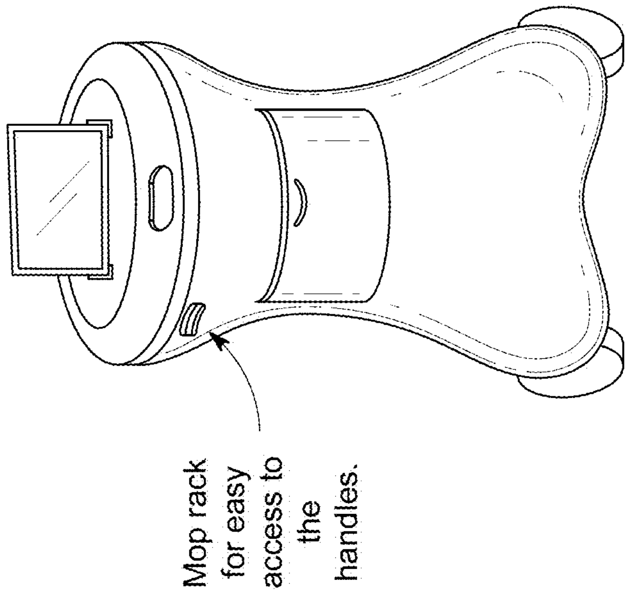
FIG. 24 is an illustration of a front isometric view of yet another illustrative fascia tissue therapy system.
Figure 27:
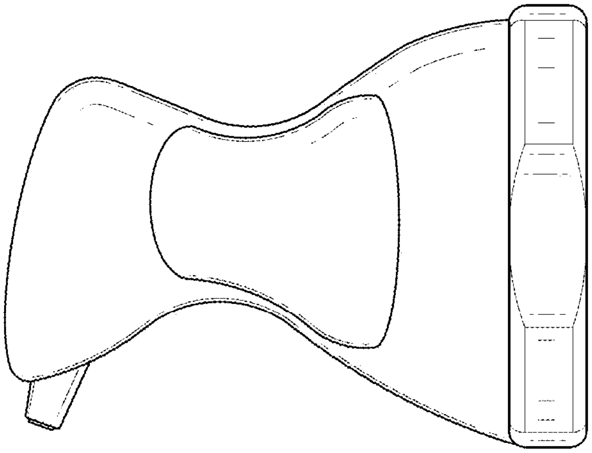
FIG. 27 is an illustration of a side view of another illustrative fascia tissue fitness device.
Figure 26:
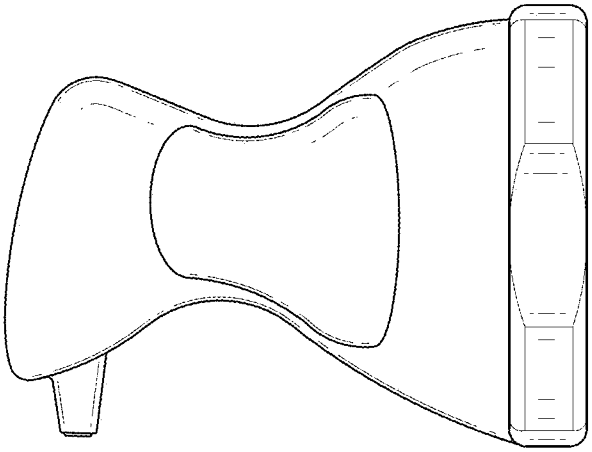
FIG. 26 is an illustration of a side view of illustrative fascia tissue fitness device of FIG. 2.
Figure 28B:
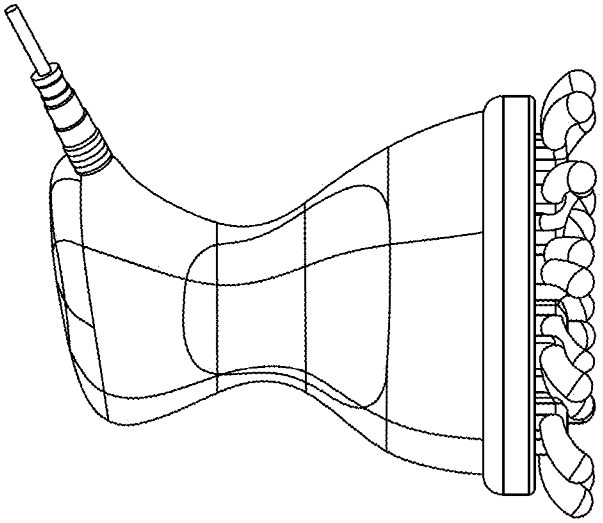
FIGS. 28A-28D are illustrations of different sides of yet another illustrative fascia tissue fitness device.
Figure 28A:
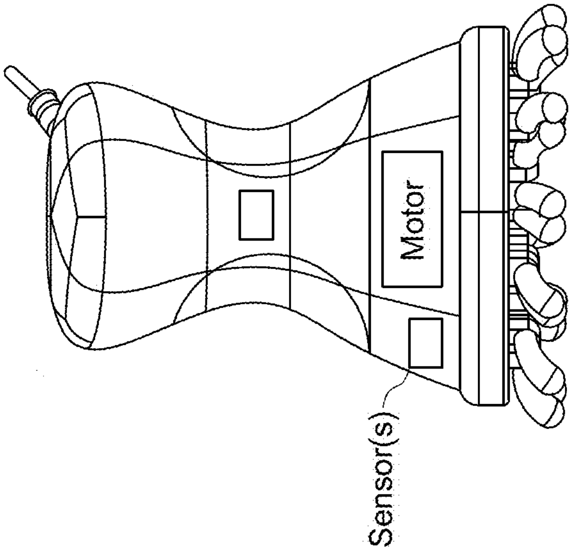
Figure 28D:
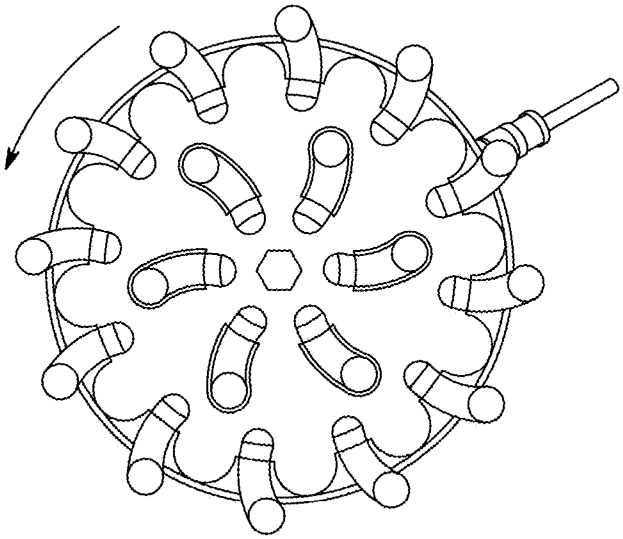
Figure 28C:
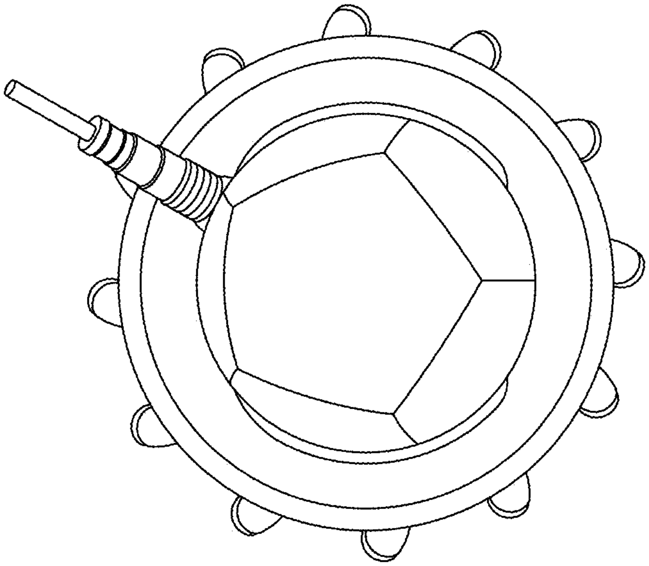

As further shown in FIG. 1, the tablet may be pivotably coupled to the base station via a mounting stand that allows the user to reposition the screen with respect to the base station. In other embodiments, as shown in FIGS. 16 and 17, the user interface (e.g., tablet) may be mounted on a swivel along an upper wall of the enclosure. The swivel may allow 360° rotation of the user interface with respect to the base station. The swivel may also include a receiver that engages the user interface and is structured to tilt relative to the upper wall of the enclosure (FIG. 17). The user interface may be remotely connected (e.g., via Bluetooth, WiFi, etc.) and/or hardwired to the base station (e.g., via the mounting stand, etc.). In some embodiments, as shown in FIG. 1, the user interface may also include buttons, toggles, and/or another form of user input device disposed on the base station (e.g., enclosure) and configured to control certain functionality of the therapy system. For example, the user interface may be configured to enable an operator to set certain conditions (e.g., shut off, alarms, alerts, self-cleaning, etc.) on the base station to perform certain functions (e.g., allow a user to be notified of certain conditions (e.g., temperature of power generator too high, temperature on treatment device too high, torque of treatment device too high, etc.). In one embodiment, the user interface may be configured to provide treatment guidance to an operator, such as modalities to perform using specific effectors for certain durations and at different speeds. The operator may perform the treatment, and the user interface may automatically collect treatment data (e.g., duration of procedure, speeds of effectors, modality, etc.). In one embodiment, the treatment device may have a trigger that causes an actuator (e.g., motor) to turn on. Speed of the actuator(s) may be controlled by a trigger that duals as a speed control. Alternatively, a speed controller (e.g., knob or selector on the treatment device) on the treatment device may enable the operator to change speed of the actuator. If the user interface operates to control the therapy or treatment device, then speed control may be established on the user interface. Still yet, if the treatment is programmed into the user interface, then speed profiles for the treatment may be established thereon so that the operator can use the pre-programmed speed or may override.

In one embodiment, the computing device is configured to (i) curate operator sign-in, scheduling of treatment, and collection of patient data (e.g., treatment notes from a clinician, treatment start and end times, etc.), and (ii) guide an operator in applying therapy device and pre-treatment procedures. The computing device may include interactive software that allows a user to obtain additional information regarding one or more treatment operations (e.g., how to activate a therapy device, how to manipulate the therapy device during treatment, etc.). The computing device may also provide video demonstrations to further clarify operation of different aspects of the therapy system, as will be further described.

In another embodiment, the computing device is configured to automatically or semi-automatically (e.g., in combination with inputs from a clinician) analyze inputs to develop treatment plans for the patient. The computing device may be configured to define a therapy regimen (e.g., the treatments to be performed), and compare pre-treatment and post-treatment results (e.g., historical results over the treatment period), among other automated and non-automated features. In this embodiment, the computing device is also configured to control therapy device operation to administer treatment and/or to provide feedback to the user and/or patient based on sensor data, as previously described and as will be further described herein.

The design of the therapy system described with reference to FIGS. 1-5 should not be considered limiting. Many alternatives and combinations are possible without departing from the inventive principles disclosed herein. For example, FIGS. 18-25 show various other illustrative embodiments of a base station for a therapy system that include different designs for the enclosure, user interface, access panel, and/or mounts for the fascia tissue treatment devices.

Referring to FIGS. 26-29, various illustrative fascia tissue therapy devices are shown for use with the fascia tissue therapy system. The therapy device (e.g., heads, etc.) is configured to apply a treatment to a user by moving an effector along a user's skin. The therapy device includes a housing, a tissue treatment effector coupled to the housing, and an actuator configured to power the effector. The therapy device may also include at least one sensor (e.g., pressure, speed, torque, temperature, etc.), heating element (e.g., IR lighting), user interface, and/or other electronic equipment.

Figure 29B:
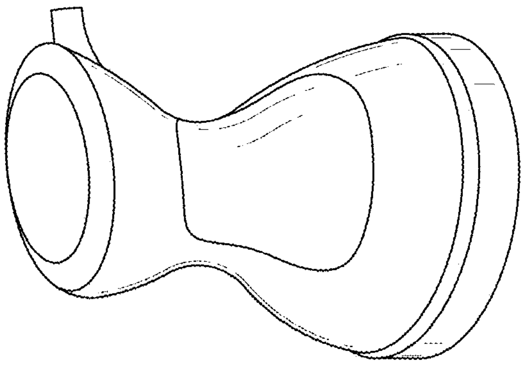
FIGS. 29A-29B are side isometric views of yet another illustrative fascia tissue fitness device.
Figure 29A:
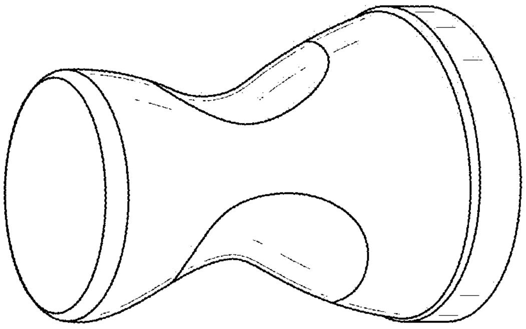
Figure 30A:
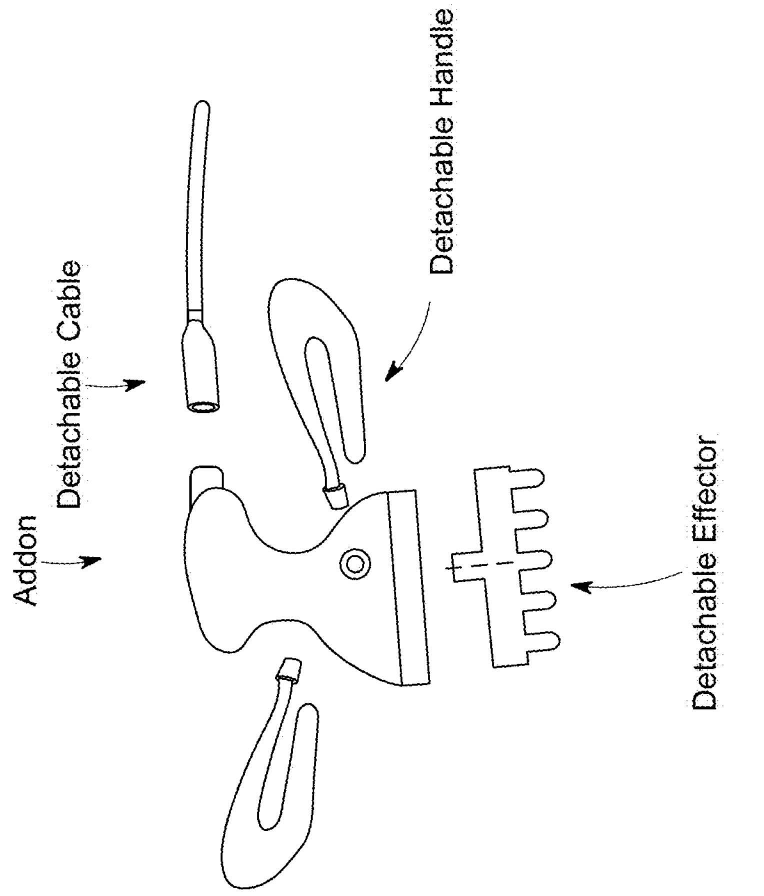
FIG. 30A is an illustration of an exploded view of an illustrative fascia tissue treatment device.
Figure 30B:
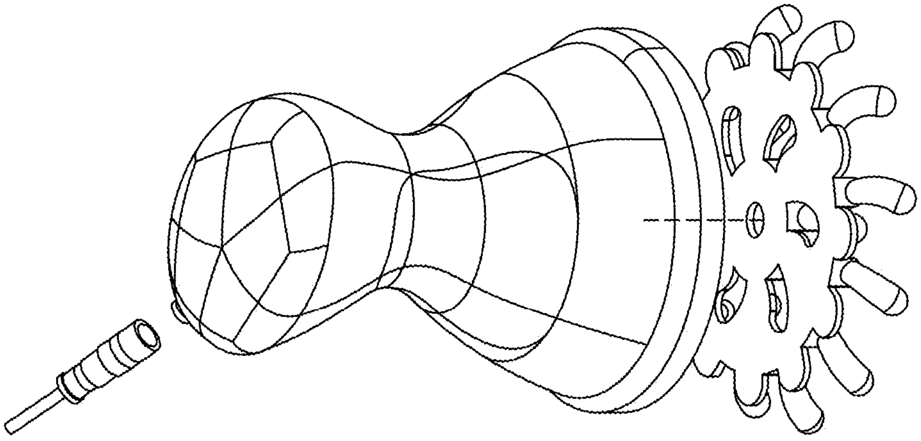
FIG. 30B is an illustration of an exploded view of the illustrative fascia tissue treatment device of FIGS. 28A-28D.

FIGS. 30A-30B show exploded views of various illustrative fascia tissue therapy device that are similar to the devices of FIGS. 26-29. As shown in FIG. 30A, the therapy device is detachably coupled to the tether of the therapy system and electrically couples the actuator and other onboard electronics to the therapy system. The therapy device is also detachably coupled to the effector and at least one handle for the therapy device. In this way, different effector designs may be used with the same therapy device. The therapy device may include a quick-connect interface, such as a chuck, snap-fit connector, and/or another form of detachable coupling to facilitate removal and replacement of the effector. The therapy device may couple to a central mounting member of the effector (e.g., a post disposed at a central position on the effector and extending axially away from the effector). In other embodiments, the mounting member may engage the effector at an intermediate radial position approximately half-way between a central axis of the effector and an outer perimeter of the effector. In yet other embodiments, the therapy device may be configured to engage the effector along an outer perimeter of the effector. Still yet, the effector may be centrally connected to a motor shaft of the treatment device. Beneficially, engaging the effector along an intermediate or outer radial position will reduce torque on the actuator during treatment (due to the smaller moment arm of the effector), reduce deflection of the effector under an applied axial force, and ensure more uniform engagement between the treatment elements of the effector and a user's fascia tissue.

Figure 31B:
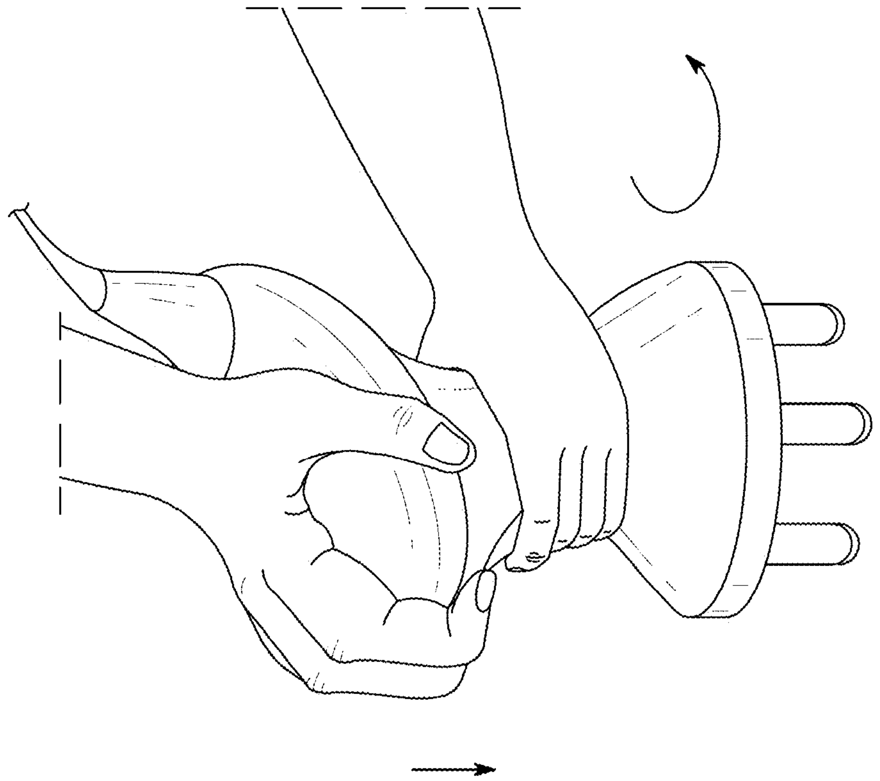
FIG. 31B is another front isometric view of the illustrative fascia tissue treatment device of FIG. 31A.
Figure 31A:
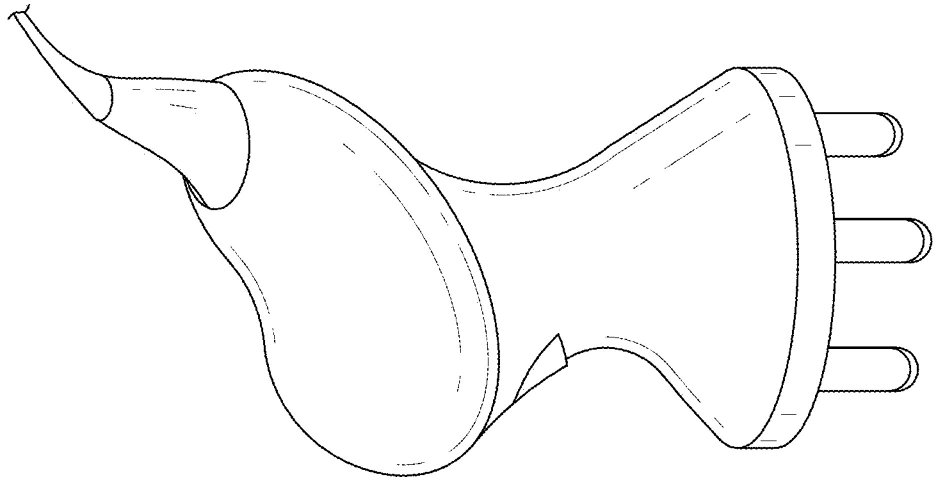
FIG. 31A is an illustration of a front isometric view of another illustrative fascia tissue treatment device.

The therapy device may be structured for use both with and without the handle depending if the therapy device is to be controlled by an operator using one or two hands. The configuration of the therapy device may, in part, depend on modalities to be performed by the particular therapy device (e.g., leg and back treatment devices are larger than face and feet therapy devices), weight of the therapy device, speed of the motor, diameter of the effector, and so on. For example, FIG. 31A and FIG. 31B show an example two-handed operation of the therapy device similar to the therapy device of FIGS. 26-30. As shown, the housing includes a lower portion that is structured to engage with the effector, an upper portion spaced axially apart from the lower portion that is detachably coupled to the tether, and a middle portion that extends between the upper portion and the lower portion. The middle portion may have a smaller cross-section than the upper or lower portion such that the upper, middle, and lower portions together form an hourglass shape. As shown in FIG. 31B, the middle portion of the housing is shaped so that an operator may wrap one of his or her hands around the middle portion, which can be used to guide the therapy device across a patient's skin. As shown in FIG. 28 and FIG. 29, the housing may include pads that enhance a user's grip on the device. The pads and/or housing may be at least partially formed from a soft silicone material to provide a pleasing velvety feel to the user when manipulating the therapy device. The therapy device may include a locking mechanism (e.g., "dead man" switch) that allows the operator to turn the device ON until the locking mechanism is released. Of course, the therapy device may include a number of sensors, such as timer, impact switch, timer, temperature, etc., that, if any of the sensors detects a problem (e.g., treatment device is dropped), then the therapy device may automatically be turned OFF.

As shown in FIG. 31A, the therapy device may also include a user interface configured to control operation of the actuator and effector. For example, the therapy device may include a switch (e.g., trigger, button, etc.) disposed along the middle portion that controls activation of the actuator. In other embodiments, the switch may also be structured to allow a user to control the speed and/or other functionality of the therapy device. For example, the user interface on the therapy device and/or base station may also include a setting selector that allows a user to manually adjust operational limits, effector stiffness, and/or other control parameters for the therapy device. In some embodiments, the therapy device may also include an auto shut-off switch and/or "dead man's" switch that deactivates and/or locks the effector in the event a rapid shut down is required. In some embodiments, the dead man's switch may also be connected to pressure/force, and/or torque measurement sensors within the therapy device and/or effector to automatically shut down the system when certain threshold values are satisfied (e.g., when the pressure and/or torque exceeds threshold values).

Figure 32:
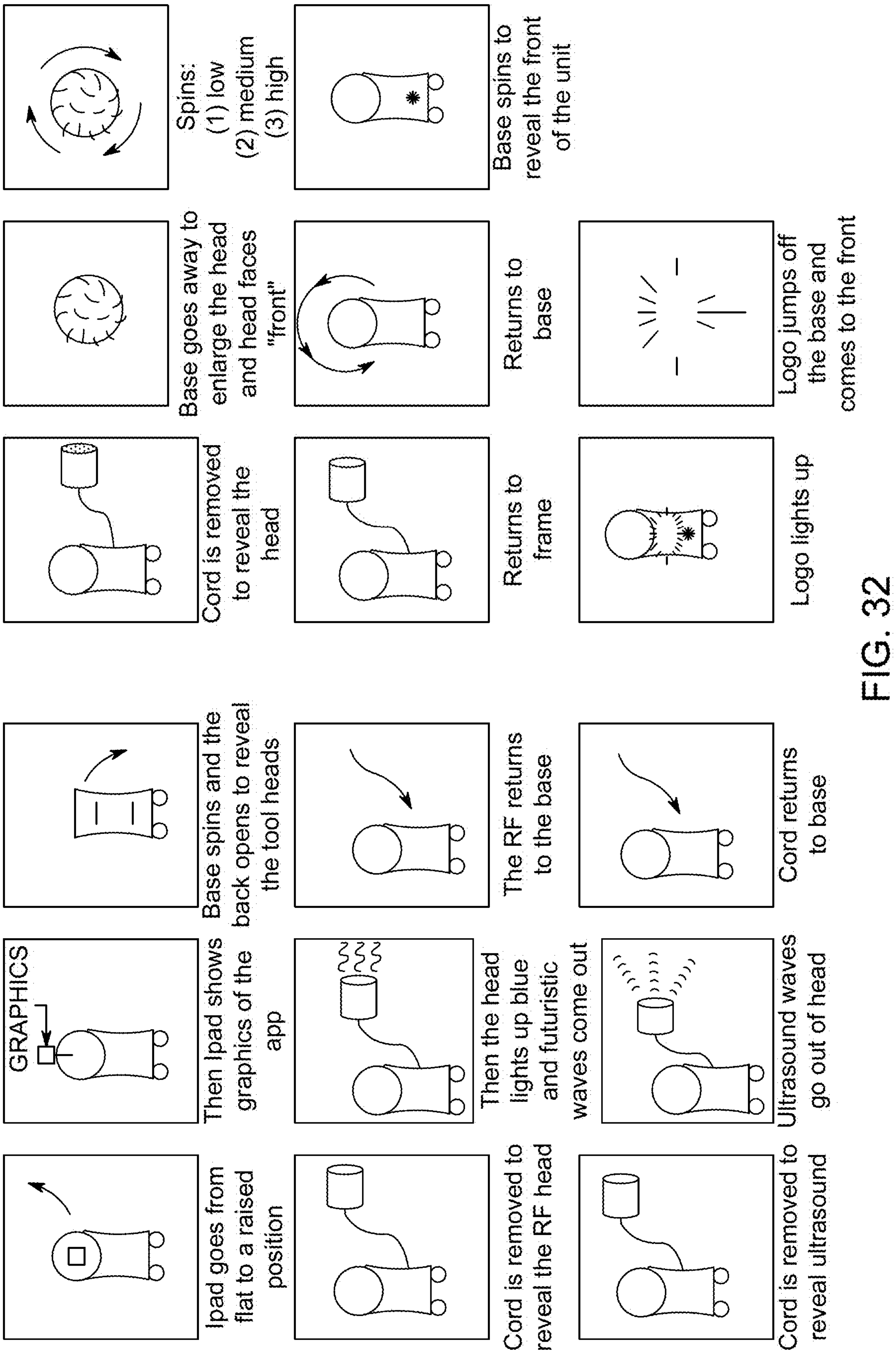
FIG. 32 is an illustration of a storyboard of a video demonstration for using a therapy device.

In some embodiments, the user interface may also be configured to provide a curated treatment procedure (e.g., modality guidance, etc.) to facilitate user interaction with the therapy device and to improve treatment effectiveness. For example, the user interface may provide step-by-step instructions informing the user of where to place the therapy device and how to hold and manipulate the therapy device during treatment. For example, the therapy device may be configured to present a video to a user (e.g., clinician, etc.) to inform the user of each step in the treatment plan, which devices to use, how to use each device. FIG. 32 shows a storyboard for an example video demonstration of a treatment plan. The demonstration includes informing the user of how to manipulate and operate base station equipment, which therapy devices to use and in what order, and the specific treatment steps to be followed for each device. As shown, the storyboard provides for pre-treatment of fascia tissue, treatment of the fascia tissue, and post-treatment. It should be understood that more specific detail showing differences for different modalities may be provided. For example, pre-treatment of a leg or torso with more muscle mass or fat content may be different than pre-treatment of a face or scalp with less muscle mass and fat content. A treatment plan may start with fascia tissue that is closer to the skin and then deeper tissue treatments may occur over time to gradually work towards restructuring fascia tissue that is deeper. Imaging (e.g., ultrasound imaging) may be used as "feedback" to an operator and/or the system, if so configured, to see how treatments are progressively restructuring fascia tissue starting from the surface and working deeper. Such treatment plans may, of course, be tailored to specific fascia tissue As shown in FIG. 31B, the upper portion is shaped so that a user may apply a downward force onto the effector and toward a patient's skin, thereby causing the effector to rotate while the pressure is being applied during treatment. By applying more pressure, the treatment to fascia tissue that is deeper (e.g., towards an underlying leg bone). The upper portion may define a planar upper surface that extends at an oblique angle relative to the central axis of the housing. A user may engage their palm with the upper surface to apply a downward force toward the skin during treatment. The angled upper surface may improve ergonomics of the device and allow a user to maintain pressure on the tissue over a longer period of time before becoming tired. It will be appreciated that the shape of the housing may be different in other embodiments.

In an embodiment, one or more feedback mechanisms may be included in the treatment device that enables feedback to be given to the operator. For example, lights for illumination, speaker for audible, vibration element for tactile feedback may be provided, where the feedback may be feedback for temperature (of the motor), high current draw (representing high torque (e.g., using current sensor)), treatment cycle start/end (using clock or motion sensor), force being applied is too low or too high (using one or more pressure sensor(s), etc.

Figure 33:
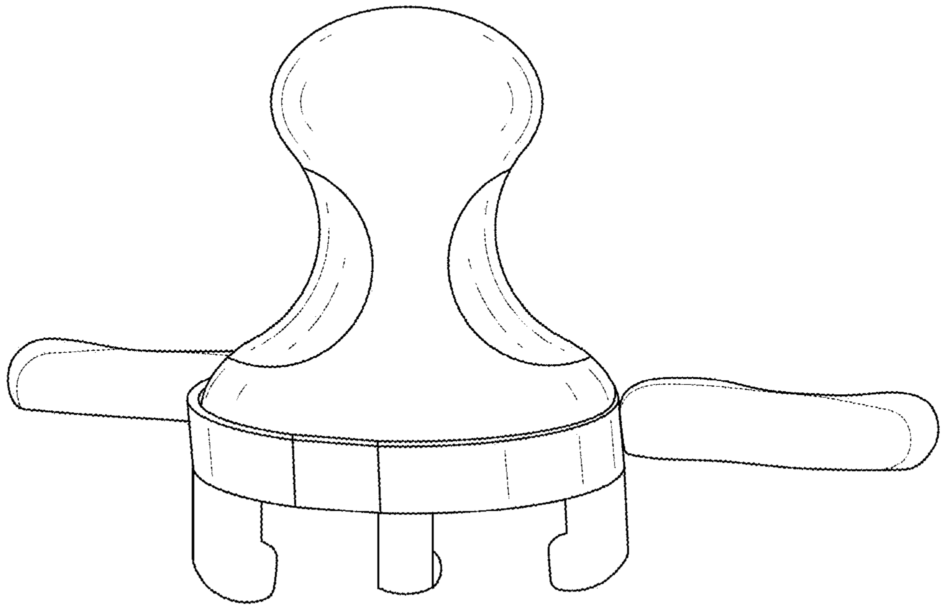
FIG. 33 is an illustration of a front isometric view of yet another fascia tissue treatment device.
Figure 34:
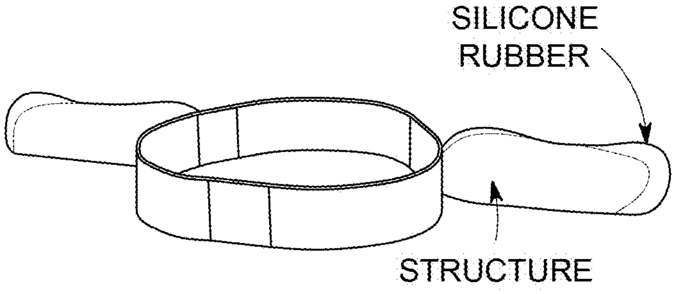
FIG. 34 is an illustration of a front isometric view of a handle for a fascia tissue treatment device.
Figure 35:
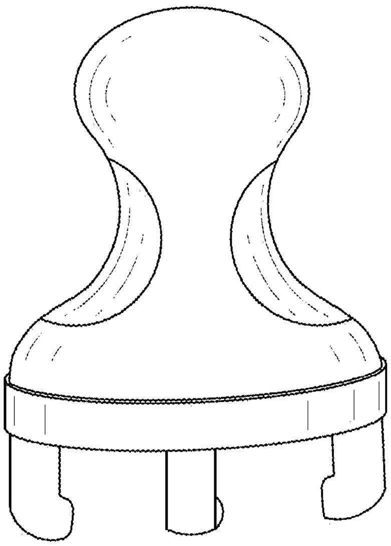
FIG. 35 is a front view of the fascia tissue treatment device of FIG. 33.
Figure 36:
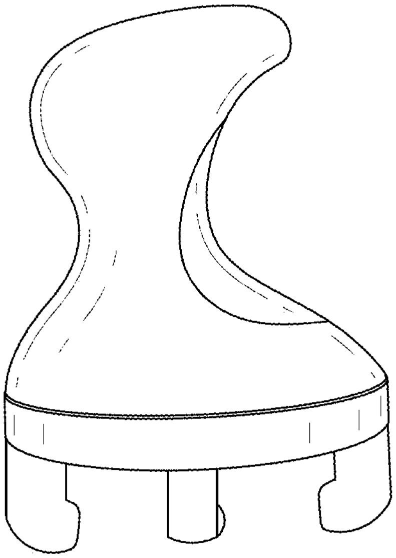
FIG. 36 is a side view of the fascia tissue treatment device of FIG. 33.

Referring to FIG. 33, another illustrative therapy device is shown that includes a removable handle. The removable handle may be removable from handles of a structural holster or strap, where the handles and/or structural holster may be formed of or include silicone rubber (or any other material). The handle may be used when using the therapy device to treat elongated body areas such as a patient's legs and back, while reducing stress to a user's hands in applying force to the therapy device. The handles and/or a strap may engage a lower portion of the housing of the therapy device, proximate to the effector. As shown in FIG. 34, the handles may be formed with the strap or holster that engages with the lower portion of the housing to couple the handle to the housing. In other embodiments (as shown in FIGS. 37-40), the handles may engage with another portion of the housing away from the effector (e.g., the middle portion of the housing, the upper portion of the housing, etc.). The strap may mount to the therapy device via a snap-fit connection, a fastener, and/or other detachably coupling. As shown in FIG. 34, the handle also includes two posts that are coupled to the strap and extend radially away from the strap. The post may be substantially cylindrical rods made from silicone rubber or another soft, yet suitably stiff material that a user can interact with to manipulate the position of the therapy device and force applied to the skin during treatment. As shown in FIG. 35 and FIG. 36, the handles may be separated from the therapy device depending on the desired treatment application, and/or to facilitate treatment of curved body areas such as the knee, neck, and others.

The handles and strap may be used during treatment and/or storage of the therapy device. In other words, the handles and strap may be held by an operator treating a patient or may simply be used for storage of the therapy device. If used during treatment, having two handles enables the operator to apply pressure equally, if desired, to both handles, thereby applying force by the effector to the patient in an equal manner. The strap may be configured to engage with the therapy device in a manner that still allows for a user interface (e.g., electronic display, LEDs, audio, etc.) disposed thereon to provide treatment and/or feedback information to the operator.

Figure 37:
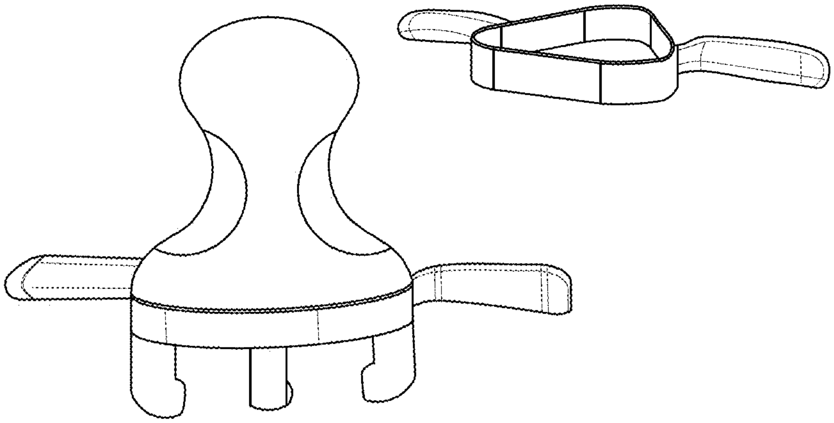
FIGS. 37-40 are illustrations of various illustrative handle designs for a fascia tissue treatment device.
Figure 38:
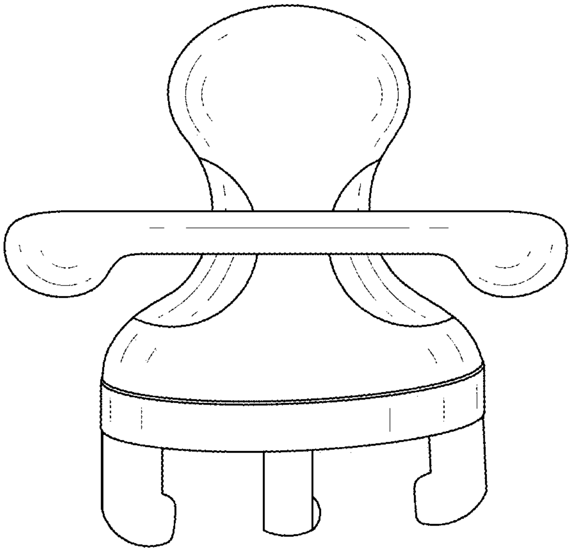
Figure 39:
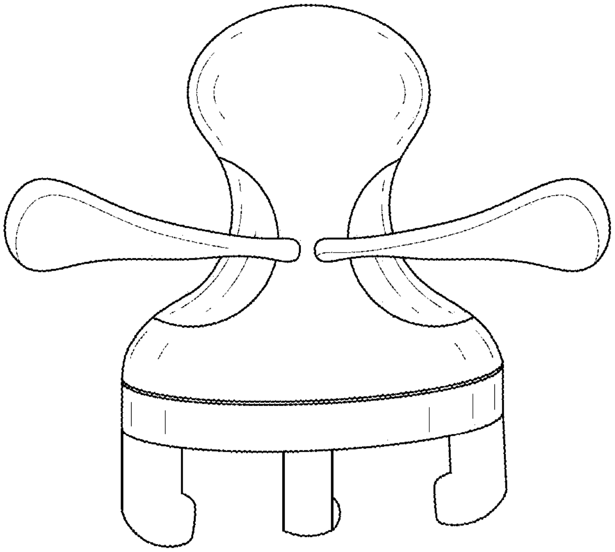
Figure 40:
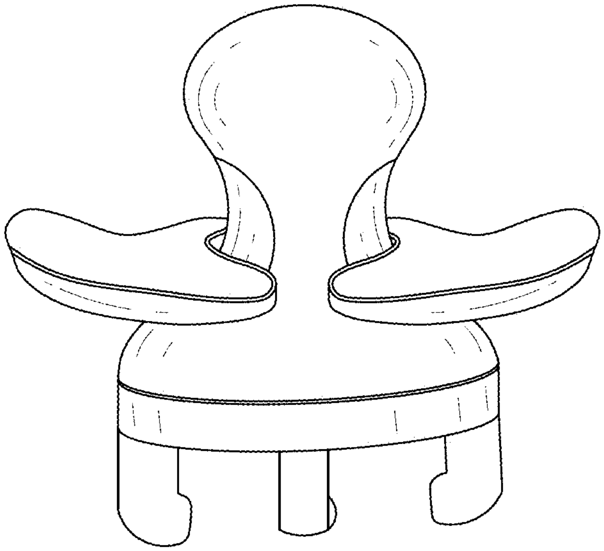

FIGS. 37-40 show various alternative illustrative handle designs for the therapy device of FIG. 35 and FIG. 36. As shown in FIGS. 37 and 38, the handle may include a strap that circumscribes the housing of the therapy device. In other embodiments (e.g., as shown in FIGS. 39 and 40), the handle wraps only partially around the therapy device and includes a slot to facilitate assembly of the handle to the therapy device (e.g., by using a flexible strap that allows increasing the size of the opening at the slot during assembly to clamp the flexible strap onto the housing). It should be understood that while the handles and/or strap may be flexible, alternative embodiments may have the handles and/or strap be rigid (i.e., not easily bent). Rather than the handles and strap being added, a housing of the therapy device may have handles formed therewith and the handles may be monolithic with the material of the housing of the therapy device.

Figure 42:
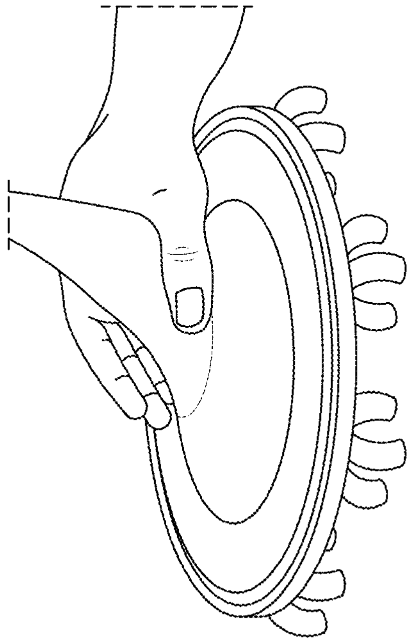
FIG. 42 is another isometric view of the illustrative fascia tissue treatment device of FIG. 41.
Figure 41:
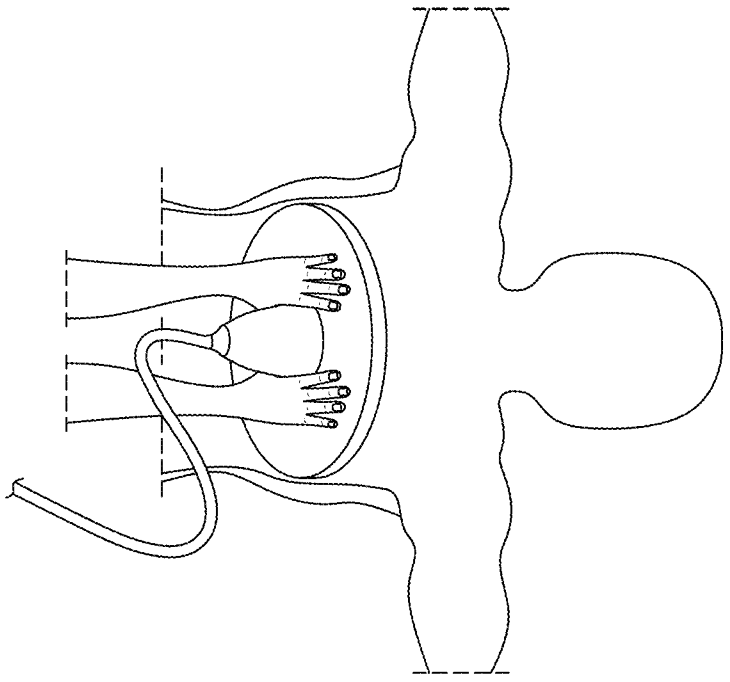
FIG. 41 is an illustration of a front isometric view of yet another illustrative fascia tissue treatment device.

The design of the housing for the therapy device may be different in various embodiments. For example, FIGS. 41 and 42 show an illustrative therapy device that includes a housing having a lower, disk-shaped portion and an upper, conically-shaped portion that extends axially away from an upper surface of the lower, disk-shaped portion. As shown in FIG. 41, a user may press against an upper surface of the disk-shaped portion to facilitate treatment of large body areas such as a patient's back or legs. As shown in FIG. 42, the user may engage with the conically-shaped portion for finer control and movement of the therapy device.

Figure 43:
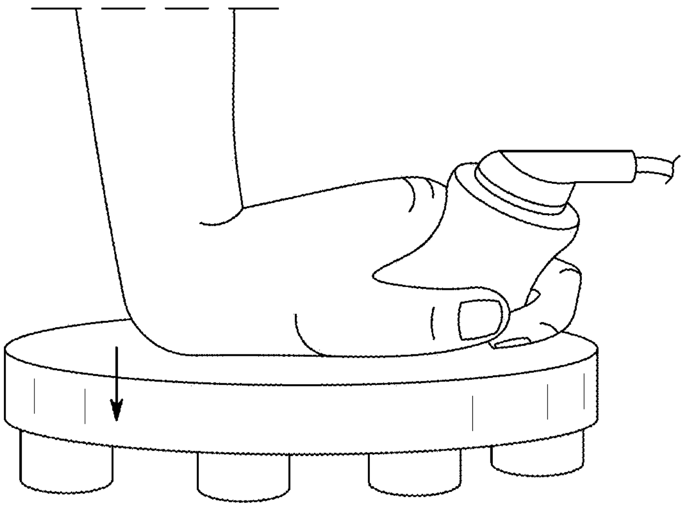
FIG. 43 is an illustration of a side isometric view of yet another illustrative fascia tissue treatment device.

FIG. 43 shows yet another illustrative therapy device. The therapy device includes a housing design that is similar to the housing of the therapy device of FIGS. 41 and 42, but that has a disk-shaped portion with a smaller cross-section to facilitate single-handed manipulation or use for treatment of body areas where increased maneuverability of the device is beneficial to the operator.

Figure 44A:
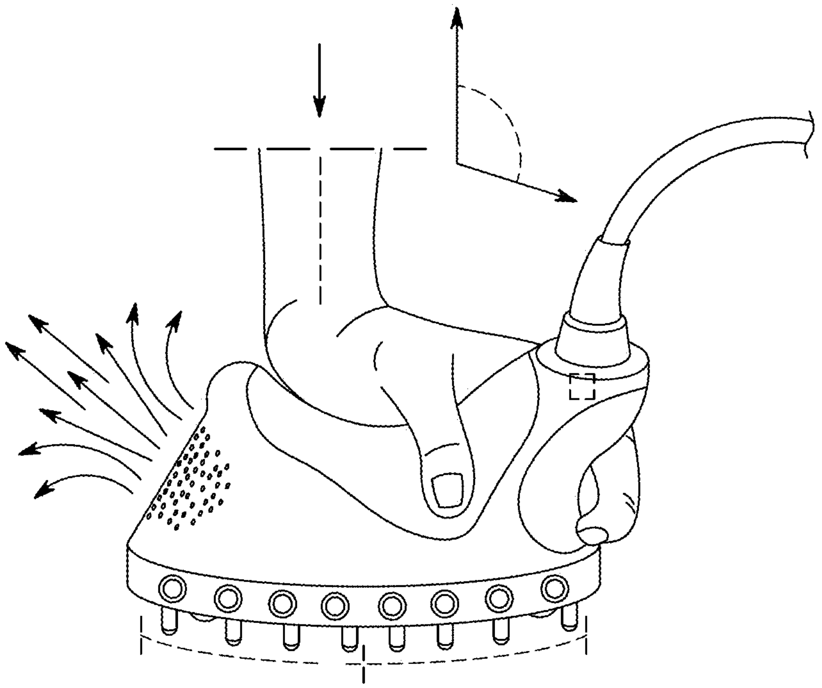
FIG. 44A is an illustration of a side isometric view of yet another illustrative fascia tissue treatment device.

FIG. 44A shows yet another illustrative therapy device. The therapy device includes a saddle-shaped housing that is designed to allow an operator to wrap his or her hand around the top of the device to both apply vertical and/or angular force and manipulate a position of the therapy device. The housing may be shaped such that a central axis of the housing is approximately aligned with a user's forearm when the operator's hand is wrapped around the saddle which, in one embodiment, centers any downward force applied to the housing during use. The saddle is also shaped to accommodate the natural angle of a user's wrist to reduce strain on the wrist during use.

As shown in FIG. 44A, the therapy device may include various add-ons to facilitate monitoring and diagnoses of damaged and/or abnormal fascia tissue, improve manipulation and restoration of fascia tissue, and to reduce the risk of damage to the device during operation. For example, the therapy device in FIG. 44A may include a cooling system that is structured to cool the actuator and/or other electronic components during treatment. The cooling system may include a fan and/or blower disposed within the housing that forces air across the actuator to exit through an exhaust port in the housing (shown as rear exhaust port in FIG. 44A). In other embodiments, the therapy device may include another form of cooling (e.g., liquid cooling) to cool internal components. Hydraulic or other cooling techniques may also be possible. As previously described, a direct drive motor may be utilized to reduce the amount of heat produced by the actuator/motor.

The therapy device may also include at least one sensor for monitoring device operations and a transceiver (e.g., WiFi, Bluetooth, etc.) for communicating sensor data with the controller and/or other networked systems. For example, the therapy device may include at least one pressure sensor structured to measure a force applied to portions of the effector, between the effector and a patient's skin. In at least one embodiment, the therapy device includes multiple pressure sensors located in different areas or quadrants of the effector panel (e.g., at different circumferential and/or axial positions along the effector panel, at equal intervals across the effector panel, at a location of each tissue treatment element along the effector panel, etc.).

The pressure sensors may be configured to provide feedback to the user via a user interface of the computing device and/or therapy device to indicate the measured pressure at the location of each pressure sensor (e.g., via a user interface of the therapy device, or via the user interface on the base station). For example, the therapy device in FIG. 44A may include multiple indicator lights disposed along an outer perimeter of the housing and facing radially away from or vertical from the housing. In other embodiments, the location of the indicator lights on the therapy device may be different. For example, the lights may be disposed on an upper wall of the therapy device, as shown in FIG. 42. The indicator lights may be configured to provide an indication of the actual force and/or pressure being applied to the effector (or a portion of the effector panel) relative to a target force and/or pressure for treatment. For example, the lights in a first circumferential quadrant of the therapy device may indicate whether the pressure and/or force applied in a nearest quadrant of the effector panel is less than a target pressure and/or force based on a color of the lights (e.g., red, yellow, green, blue, etc.), an amount of flashing, and/or other visual indication. In an embodiment, if a target range of forces (i.e., low force threshold and high force threshold) is established for a particular modality or treatment, then in the event that force (e.g., force in a quadrant of the effector) is sensed to be too low, then lights (e.g., LEDs) may be illuminated to be one color (e.g., blue) and if sensed to be too high, then lights may be illuminated to be in another color (e.g., red). If the pressure is sensed to be within range of the desired treatment levels, then another color (e.g., green) may be displayed by the lights. If sensors configured in quadrants are used, then the feedback (e.g., lights) may be displayed in relation to each pressure measured in the quadrants associated with the sensors in the respective quadrants. Other color schemes may be utilized, as well. Moreover, the pressure sensor feedback signals may be collected by the user interface and stored thereon, thereby enabling the user interface or another computing device to correlate pressure, therapy devices, operator, etc. with fascia tissue restructuring progress, for example.

The therapy device may also include a speaker to provide audible and/or tactile notification of the applied vs. desired level of pressure and/or force to a user. In some embodiments, the pressure sensors may also be used to determine an average pressure across the effector (e.g., by averaging measurements from each pressure sensor), a peak pressure across the effector, and/or to facilitate calibration of the therapy device (e.g., to facilitate adjustment of an angle of the effector relative to the housing of the therapy device after a new effector has been installed). If, for example, pressure is too low, a change of an audible signal (e.g., Geiger counter tones, frequency, pitch, and/or volume of an audible signal, etc.) or a notification signal (e.g., tone, beep, etc.) may be produced.

Figure 44B:
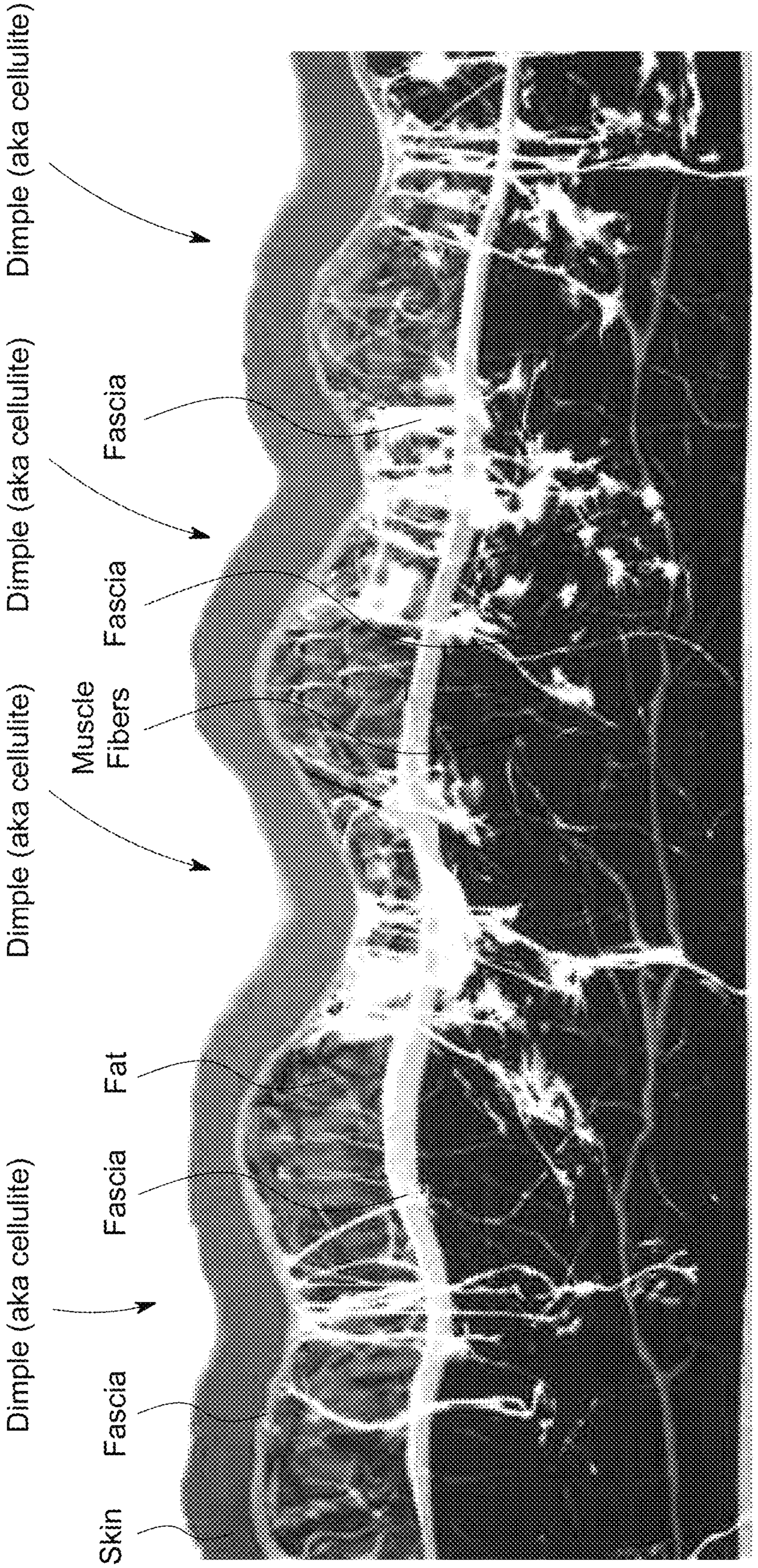
FIG. 44B is an illustration of a cross-sectional view of illustrative fascia tissue layers.

The therapy device may also include other types of sensors and/or transducers to facilitate assessment of fascia tissue abnormalities prior to, or during, treatment. Examples of fascia tissue layers and damage is shown in FIG. 44B. Outer and inner structural fascia tissue layers (thin layer beneath the top skin surface layer) are shown to separate skin (top surface layer), subcutaneous fat (beneath the top outer structural fascia tissue layer), and muscle (layer below the subcutaneous fat later) layers. Also shown are inter-structural fascia tissue fibers that extend between the structural tissue layers. Problem areas occur in regions of high fascia tissue density of the inter-structural fascia tissue fibers, which may also be described as adhesions of the fascia tissue. As shown, pockets/dimples (commonly referred to as cellulite) are formed on the skin surface as a result of the adhesions of the inter-structural fascia tissue fibers. While skin aesthetics may result from adhesions of the fascia tissue, more health-related problems may also result. Such health-related issue may include pinched nerves, reduced blood circulation, muscle pain due to the inter-structural fascia tissue fibers having reduced flexibility, tearing of the fascia tissue if the fascia tissue fibers are too intertwined, and so on.

In various embodiments, the therapy device may include an ultrasound system and/or sonography imaging device that uses high-frequency sound waves to produce images of the fascia tissue, including different layers of fascia tissue depending on the ultrasound sensor and imaging software. The ultrasound system may form part of the computing device for the therapy device and may be configured to transmit images to the controller for further analysis. The controller may be configured to utilize the images to identify problem areas along a patient's body. In an embodiment, a medical professional and/or operator may be create a treatment plan based on the imaging of the fascia tissue with the assistance of the user interface. In an alternative embodiment, the user interface may be configured to determine a treatment plan based on the images, and evaluate treatment progress over time based on repeated images of the same area, as further described hereinbelow.

Figure 44C:
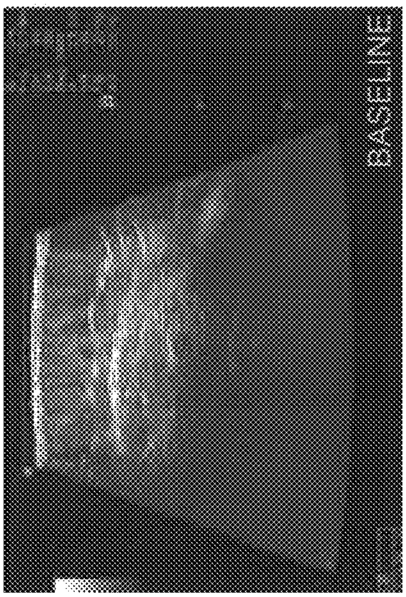
FIGS. 44C-44F are images from an ultrasound analysis of patient tissue taken at different intervals during treatment using a fascia tissue therapy device.
Figure 44D:
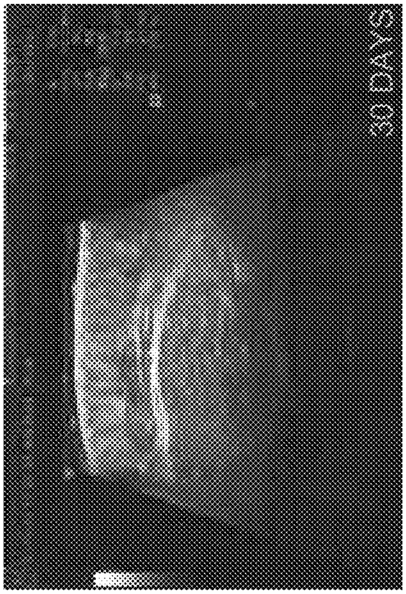
Figure 44E:
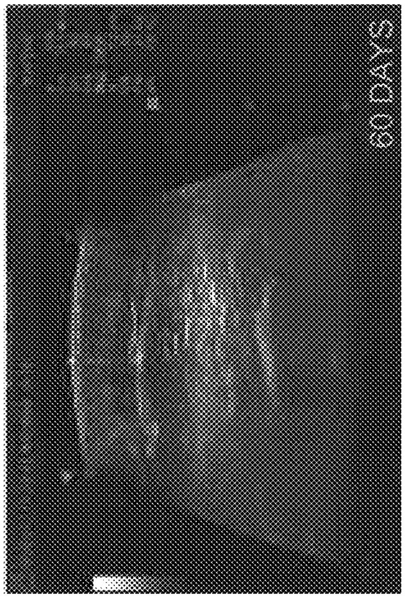
Figure 88:
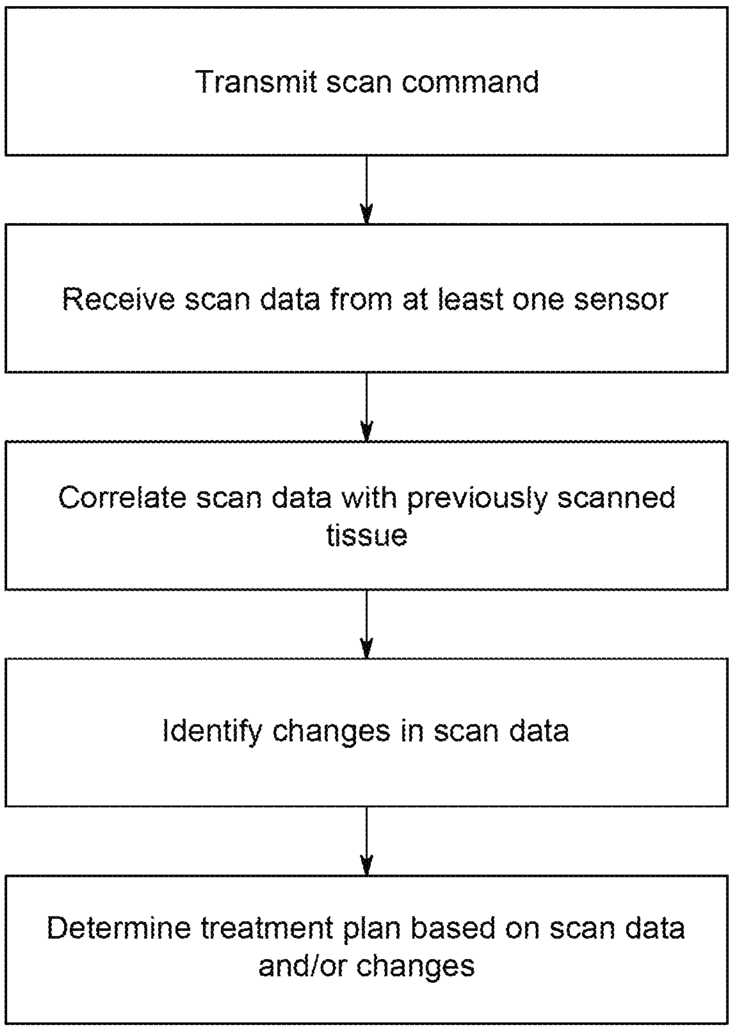
FIG. 88 is a flow diagram of an illustrative method for fascia tissue analysis.

For example, in a pre-treatment mode, the controller may be configured to guide a user to place the therapy device at different locations along a patient's body to map various areas of the body (see ultrasound image in FIG. 44C). The controller may be configured to operate the ultrasound system at each location to obtain images across a range of resolutions and/or tissue depths (e.g., three tissue depths at each location, etc.). The controller may then analyze the images to identify areas of high fascia tissue density, fragmentation, and/or other image characteristics that are indicative of fascia tissue abnormality. The controller may be configured to perform image analysis based on predetermined algorithms in memory, and/or by transmitting the images to a remote computing system (e.g., a cloud computing system) for further analysis. In at least one embodiment, the controller may be configured to use images from different patient screenings (in combination with user inputs identifying problem areas) as a training set for machine learning and/or artificial intelligence (AI) algorithm that can automatically identify fascia tissue damage and/or abnormalities. The machine learning algorithm may also be used—in combination with historical data from patient treatment protocols—to determine a treatment plan based on the detected fascia tissue abnormalities. The machine learning algorithm may utilize a k-nearest neighbor (KNN) algorithm and/or another classification algorithm to classify fascia tissue characteristics relative to common fascia tissue characteristics of other patients so that successful treatments that work for different types of fascia tissue characteristics can be applied to a patient. The AI identification of certain fascia tissue characteristics may be specific to specific body areas (e.g., lower back, calves, scalp, etc.) requiring treatment, the type of treatment that is required, and/or the required number of treatments. The controller may be configured to utilize the ultrasound images to determine or select particular effector characteristics (e.g., size, shape, finger orientation, etc.) and control parameters (e.g., operating speed, force, etc.) to use to improve treatment efficacy. Referring to FIG. 88, an illustrative method of fascia tissue analysis is shown. The method includes transmitting a scan command to a therapy device to perform a fascia tissue scan (e.g., via ultrasound, etc.), receiving scan data (e.g., images of the tissue at different depths, etc.), correlating scan data with previously scanned tissue, identifying changes in scan data (e.g., by comparing scan data with images from previous scans, etc.). In some embodiments, the method also includes determining a treatment plan based on scan data and/or identified changes in scan data. In other embodiments, the method may include additional, fewer, and/or different operations.

The therapy device may also include sensors that interface with the computing device to ensure the correct device and/or effector is being used for a prescribed treatment protocol and to monitor operation of the therapy device during treatment (e.g., the average applied force, torque, rotational speed, duration of use, etc.). For example, each therapy device may be coded with a type, size, etc., and each effector may also be coded with a type, size, finger or treatment element type, shape, etc. In coding the therapy devices and effectors, chips, such as RFID chips or processor chips or memory chips, may be coded with identifying information, thereby enabling the user interface to receive and record the identification information so that historical records may be maintained in an automatic manner. The controller may record this data at periodic intervals (as shown in FIGS. 44C-44F), which can be fed back into the machine learning algorithm to update and/or improve treatment prescription.

The therapy device may also include other forms of skin treatment devices. For example, the therapy device may include an infrared element to treat a patient's skin and/or underlying tissue, a radio frequency skin tightening system, and/or ultrasonic tissue treatment system. In some embodiments, the therapy device also includes a lubrication system (e.g., nozzles, a micropump, etc.) that is structured to dispense a lubricating agent to a patient's tissue to reduce friction between the effector and the patient's skin during rotation of the effector, thereby enabling the operator to continuously treat the patient without having to stop using the therapy device. In an embodiment, feedback from a torque sensor may be utilized to determine when additional lubricant should be applied to the skin, and the lubrication system may automatically dispense or be caused to dispense lubricant to the skin by the therapy device. These auxiliary treatment devices may be at least partially contained within the housing of the therapy device and/or may be attached to the treatment device in place of, or in addition to, the effector. In yet other embodiments, these auxiliary treatment devices may form their own therapy device that may be detachably coupled to the base station. The lubrication may be stored in a reservoir stored in the enclosure that may be refillable or cartridges of lubrication may be replaced in the lubrication system, as previously described.

The actuator of the therapy device is configured to power rotation of the effector. The actuator may include a direct drive motor that engages the effector without any intervening transmission or gear set. Among other benefits, using a direct drive motor reduces heat produced by the therapy device and wear on the internal components. The direct drive motor may also reduce the weight of the therapy device due to the increased torque to weight ratio of the motor. In other embodiments, the actuator includes another form of electromechanical device (e.g., brushless direct current motor, electromagnetic device, etc.). In other embodiments, the actuator includes a pneumatic motor that is configured to drive rotation of the effector using air pressure. For example, the pneumatic motor may consist of a turbine in the therapy device housing that is driven into rotation by compressed air provided through the tether to the base station. In other embodiments, the actuator may include a hydraulic motor and/or system.

Figure 44F:
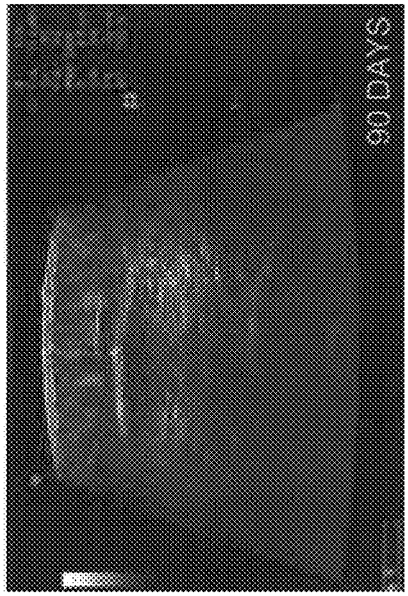
Figure 44G:
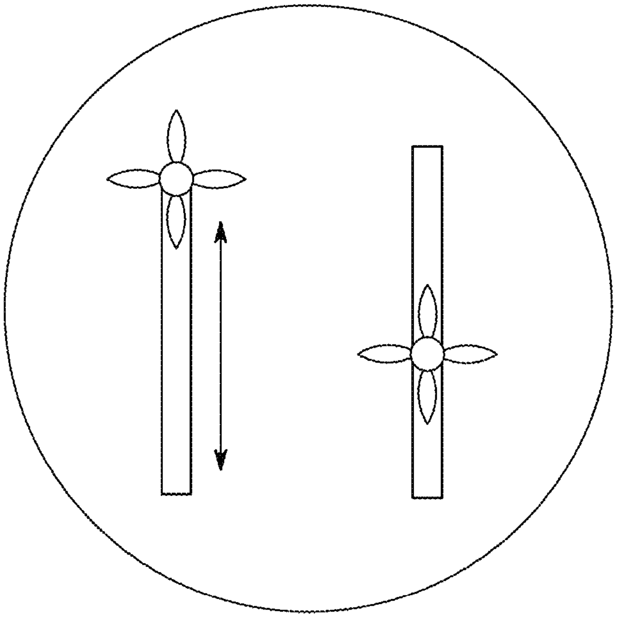
FIG. 44G is an illustration of a bottom view of yet another illustrative fascia tissue treatment device.
Figure 44H:
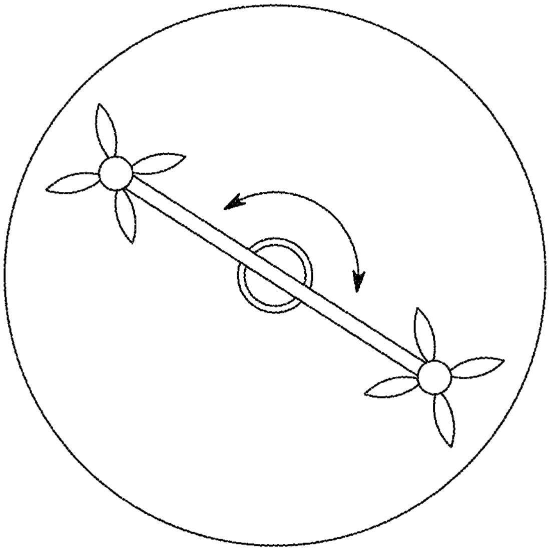
FIG. 44H is an illustration of a bottom view of yet another illustrative fascia tissue treatment device.

In some embodiments, the actuator may be configured to move the effector and/or individual treatment elements along a single direction (e.g., linearly back and forth, etc.). For example, FIG. 44G shows an illustrative fascia tissue therapy device in which the actuator is structured to move individual treatment elements back and forth along a single direction. The elements may be staggered at different positions along each actuator or aligned. FIG. 44F shows another illustrative fascia tissue therapy device in which the actuator includes a radial bar that connects multiple tissue treatment elements and alternates direction to move each element along a semi-circular path. In yet other embodiments, the therapy device may include a shaft with offset lobes (e.g., similar to an engine crankshaft) to move the treatment elements along guides (e.g., slots) in the housing (e.g., similar to the direction of movement shown in FIG. 44G). In yet other embodiments, the therapy device may include feet (e.g., made from silicone and/or coated with silicone or another suitable material) that may translate back and forth along the therapy device, as shown in FIGS. 76-82. It should be understood that the size of the feet and range of motion of the feet may be different in various embodiments.

Figure 45A:
FIG. 45A-45G are illustrations of various illustrative fascia tissue treatment devices for use with a therapy system.

In yet other embodiments, the actuator may be another form of rotational and/or vibrational device (e.g., an electromagnetic device, a rotating cable extending through the tether and driven by a motor in the base station, etc.). Vibration of the treatment device may be random or nonrandom. For example, the device may rotate and vibrate up-and-down. The device may alternatively rotate and randomly vibrate. For example, FIG. 45A is an isometric view of an illustrative therapy device that includes a linear actuator that is configured to vibrate or otherwise translate a treatment element back and forth along a linear direction. The treatment element may thereby thump, hammer, or pulsate against the patient's tissue during operation.

In some embodiments, the actuator may also be configured to vibrate the effector in combination of spinning or another form of movement.

Figure 45B:
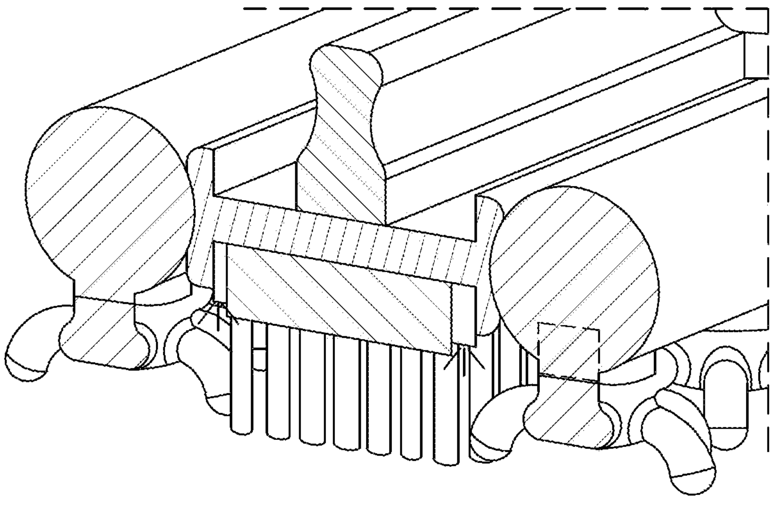

In some embodiments, the therapy device (e.g., actuator, etc.) may be configured to apply micro-currents or certain electrical currents through the effector and/or another treatment accessory to electrically stimulate the tissue in combination with spinning and/or vibration and/or to apply light in certain wavelengths to enhance fascia tissue treatment by the therapy device. As shown in FIG. 45B, the therapy device includes a treatment accessory that is detachably coupled to the therapy device that is configured to apply electrical currents and light in certain wavelengths to a patient's skin. The treatment accessory includes brushes arranged in rows along the treatment accessory, although various other arrangements may be used in other embodiments. The bristles of the brush may be made of any suitable material including nylon, polypropylene, horse hair, feather, or any other natural or synthetic filament material. The tips of the bristles may be flocked (split) or unflocked. The tips of the bristles may also be rounded, bulbous, flat, pointed, etc. The bristles may be soft and flexible for a comfortable and soothing treatment, or may be rigid and stiff for a more aggressive tissue treatment. In some embodiments, the bristles include both soft/flexible bristles and rigid/stiff bristles for a combined treatment. In other embodiments, a first brush of the treatment device may have a first type of bristles and a second brush having a different type of bristles.

The therapy device of FIG. 45B also includes a light therapy system including a plurality of light emitting diode (LED) lights directed toward the skin to provide additional therapy to the fascia tissue. The light therapy system may provide light in one or more of the following forms: Red light (625 nm), Blue light (415 nm), Red+Blue light (625 nm~415 nm), Infrared (760 nm). The computing device may be configured to power and control operation of the LEDs. User input controls, such as knobs, buttons, or otherwise, may be accessible to a user from the therapy device and/or base station to control operation of the LEDs and control circuitry.

The LEDs may be disposed at any location in which the light can be properly directed to a patient's skin (i.e., is not blocked by another element of the therapy device). For example, the LEDs may be at the tips of the treatment elements or along a periphery of the therapy device. The LEDs may be pointed at an angle outward from the device, toward the effector, or in any other location, arrangement, and/or orientation so as to direct light onto the skin surface. The LEDs may be aimed in front of, to the side, or between the treatment elements so that the lights may be incident skin of a user prior to and/or after the treatment elements pass a region of skin of a user. In an embodiment, a motion sensor may sense when the device is in use (e.g., moving back and forth) and cause the LEDs to automatically turn ON during motion, and cause the LEDs to automatically turn OFF when not in motion or not moving in a particular treatment motion (e.g., rotating, substantially linearly forward/backward or side-to-side, where substantially means that there may also be some rotational and/or vibrational movement during operation). One or more pressure sensors (e.g., between the treatment element(s) and bar) may also be utilized to determine when the device is in operation and cause the LEDs to turn ON and OFF. A timing circuit may be utilized to maintain the LEDs in the ON state for a minimum duration of time (e.g., 15 seconds). In an embodiment, circuitry may turn the LEDs ON and OFF in a particular pattern, such as lighting certain LEDs when moving in a first direction and other LEDs when moving in a second direction.

As shown in FIG. 45B, the therapy device may also include a soft tissue stimulation system configured to provide electrical current to the treatment area by placing a plurality of electrodes on the skin surface and providing electrical impulses via the electrodes to the skin and soft tissue (such as fascia tissue) below the skin's surface. In some embodiments, the stimulation system employs circuitry and hardware elements that can execute traditional TENS (transcutaneous electrical nerve stimulation) and/or LAMES (neuromuscular electrical stimulation) therapy. In such embodiments, at least one lead wire may be electrically coupled to the device, with a transcutaneous electrode at the distal end for delivering the electrical impulses to the patient. The transcutaneous electrode may adhere to the skin. The device may be configured to provide a pre-determined stimulation waveform having a pre-determined frequency (Hz), pulse width (μs), and amplitude (mA). Alternatively the device may be configured to allow a user to modify one or more parameters of the stimulation waveform.

In some embodiments, the electrodes may alternatively be positioned on the device housing (such as on the frame, the bar member, the treatment elements, or the treatment accessory, to be placed in direct contact with the skin for stimulation. In an embodiment, the treatment accessories, for example, may be configured with an accessible compartment that is configured to store batteries, control circuitry, electrode(s), wires, etc., thereby enabling the treatment to be self-contained within the treatment accessories. In other embodiments, the treatment accessories are electrically coupled to the therapy device and powered by the base station. User input controls, such as knobs, buttons, or otherwise, may be accessible to a user to control operation of the stimulation signals applied to a user from the electrodes controlled by the control circuitry. In operation, the user may remove the electrode(s) from the compartment and apply to him or herself. The electrodes, in an embodiment, may be attached to straps that may wrap around or be applied to a patient's body, such as an arm or leg, so as to apply the TENS or LAMES treatment before, during, or after fascia tissue treatment by the device with the treatment elements. As an example, the electrodes may be positioned to the sides of a pathway that the treatment elements are to be applied and electrical stimulation may occur before, during, or after treatment.

Figure 85:
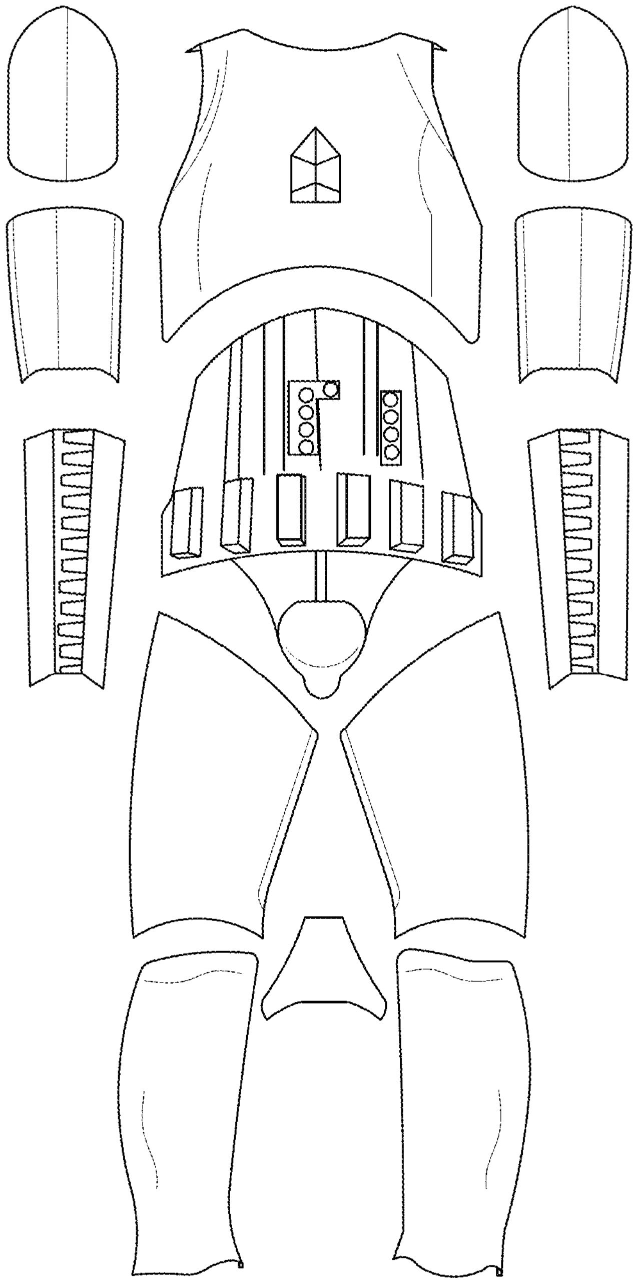
FIG. 85 is an illustration of a front exploded view of an illustrative preparation device.
Figure 86:
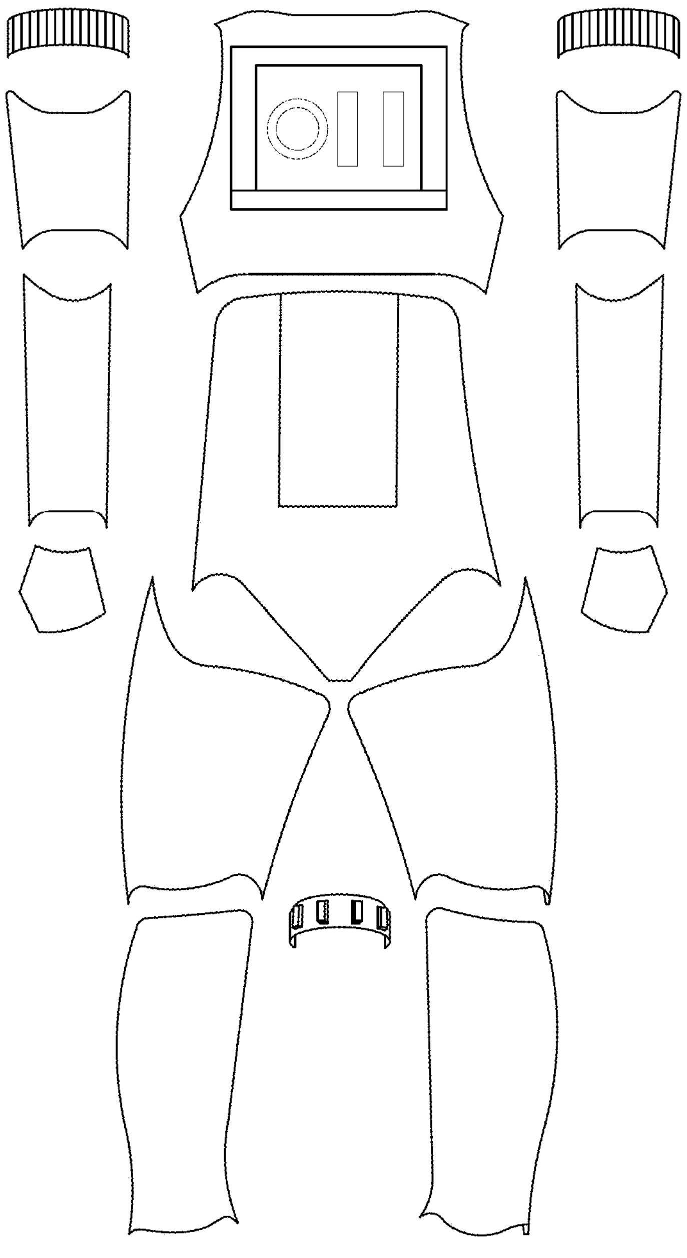
FIG. 86 is an illustration of a rear exploded view of an illustrative preparation device.
Figure 87:
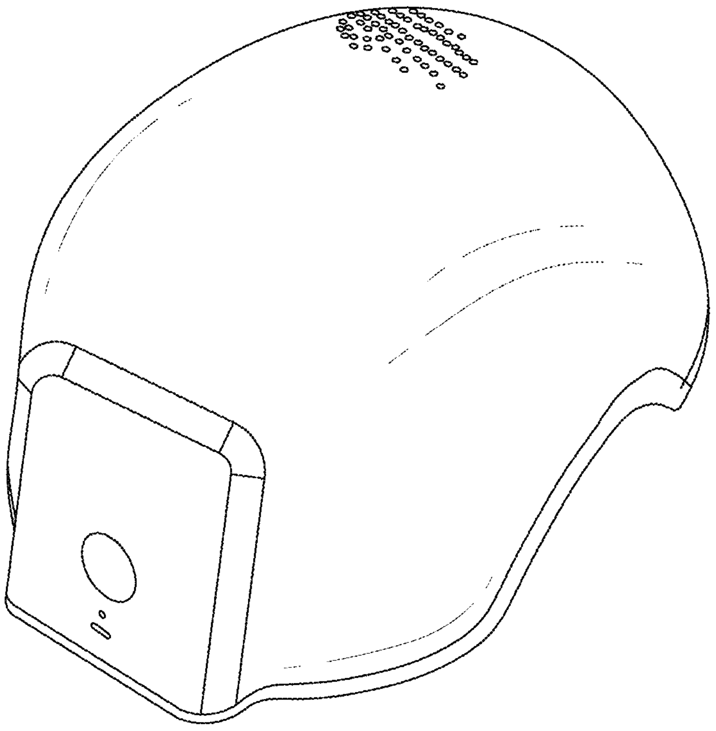
FIG. 87 is an illustration of an isometric view of a helmet for an illustrative preparation device.

As described above, the base station may be configured for use with multiple different types and/or styles of therapy devices. In some embodiments, the treatment plan may involve using different therapy devices and/or device attachments in a certain order. For example, the treatment plan may include application of a skin and/or soft tissue preparation device to the patient. The preparation device may include equipment that is structured to be worn by the patient. In one embodiment, the preparation device may include an outer shell (e.g., plastic, etc.) that is shaped to match the contour of a certain body area(s) (e.g., a patient's head, shoulder, thigh, etc.). An illustrative shell (e.g., armor, etc.) for a preparation device is shown in FIGS. 85-86. An illustrative helmet (e.g., head gear, etc.) for a preparation device is shown in FIG. 87. The preparation device may include soft padding that is coupled to an interior surface of the shell to improve patient comfort, and straps (e.g., a hook and loop fastener, cord, etc.) to help secure the preparation device to the patient during pre-treatment. The preparation device may be configured to pre-heat and/or soften the patient's tissue prior to the use of other treatment modalities. The preparation device may include lights (e.g., UV lights, infrared heating elements, etc.), gel-packs, ultrasonic transducer (e.g., vibrating elements), or another technology that is coupled to the shell and/or padding and positioned to engage with a patient's skin. In some embodiments, the preparation device may also include nozzles and/or another dispensing device or system to apply lubricating oils or other agents to facilitate heat absorption to the skin and to prepare the skin/tissue for further treatment).

Figure 45C:
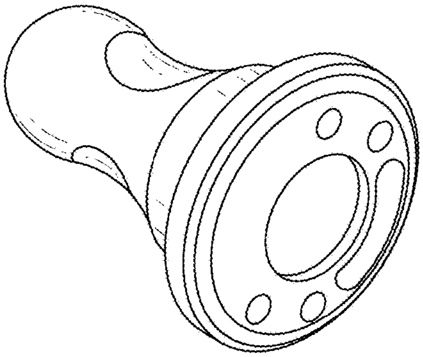
Figure 45D:
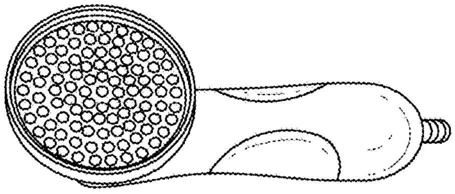

After pre-treatment, the treatment plan may involve using a radio frequency (RF) device (e.g., RF head) as an initial treatment operation. The RF device may be configured to use energy waves (e.g., thermal energy) to help stimulate the superficial skin layers and/or to heat the deep layer of a patient's skin (e.g., to within a range between approximately 122 and 167° F., or another suitable temperature). Illustrative RF treatment devices are shown in FIGS. 45C-45D. The treatment plan may include using the RF treatment device(s) to apply heat for a prescribed period to stimulate the tissue and promote creation of new collagen fibers.

Figure 45E:
Figure 45F:
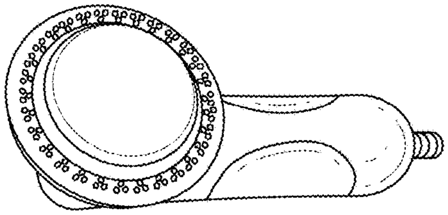
Figure 45G:
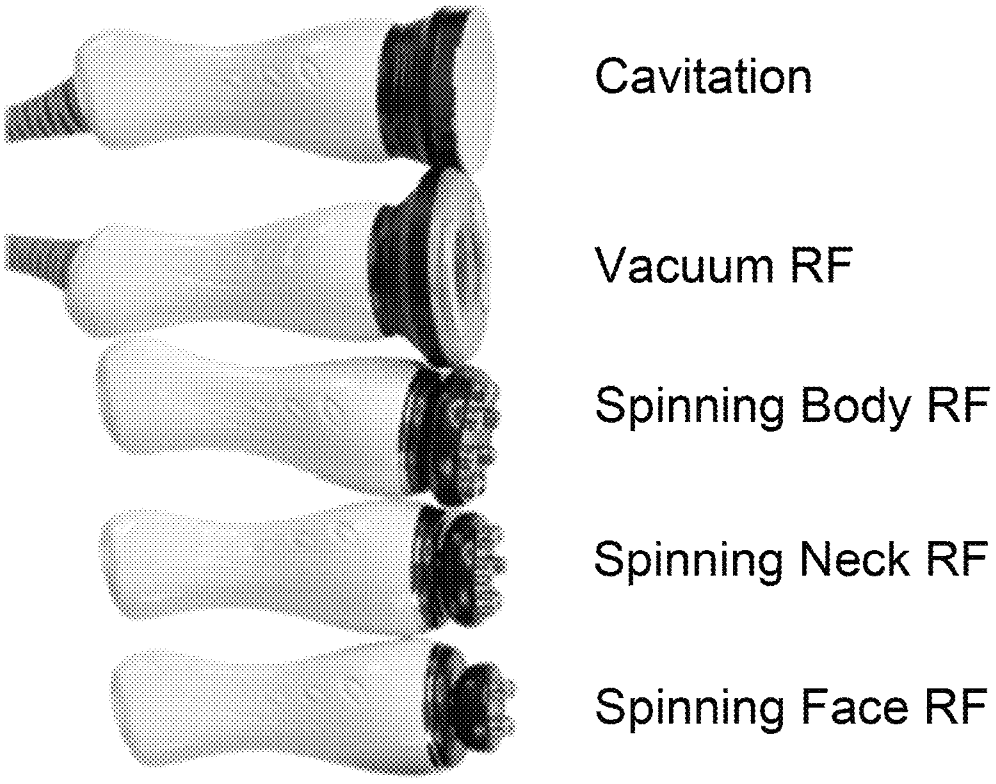

The treatment plan may also include using an ultrasound skin treatment to facilitate the removal of fat deposits under a patient's skin and/or heat the patient's tissue. For example, FIGS. 45E-45F show an illustrative ultrasonic cavitation device for a tissue treatment that may be coupled to the tether and base station. The cavitation device may be configured to apply ultrasonic radio waves to the tissue, causing a disruptive vibration. FIG. 45G shows additional therapy devices that may be powered by the therapy system. Examples include cavitation devices, vacuum devices that apply negative pressure to tissue during operation, and/or combination devices that utilize multiple treatment modalities (e.g., RF in combination with spinning or other movement). The treatment plan may also include application of infrared light (e.g., via an IR treatment device), pre-cancerous treatments (e.g., blue light therapy), acne treatment, and/or other tissue treatments. These treatment devices may be accessory heads that can be interchangeably coupled to a single therapy device or separate therapy devices that are coupled to the base station in place of the therapy device, as described above.

Figure 45H:
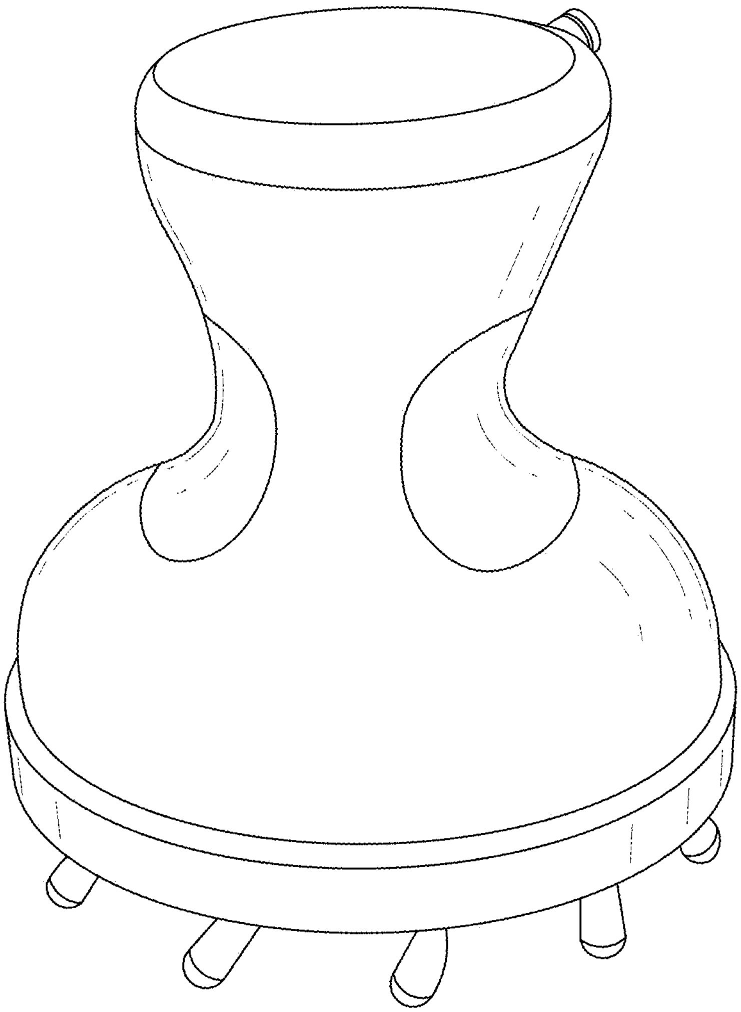
FIG. 45H is an illustration of a isometric view of yet another illustrative fascia tissue treatment device.
Figure 46A:
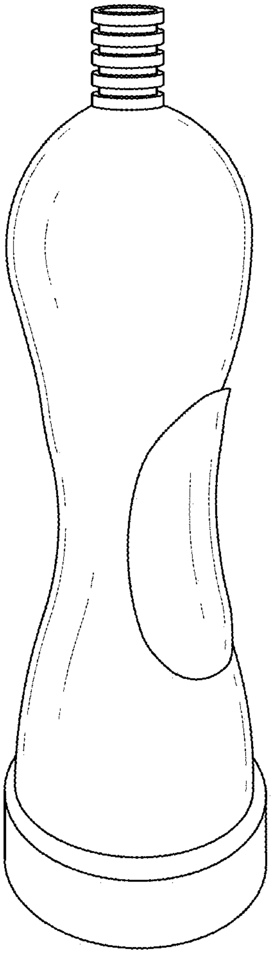
FIGS. 46-53 are illustrations of various illustrative fascia tissue treatment devices that may be used to treat smaller body areas.
Figure 46B:
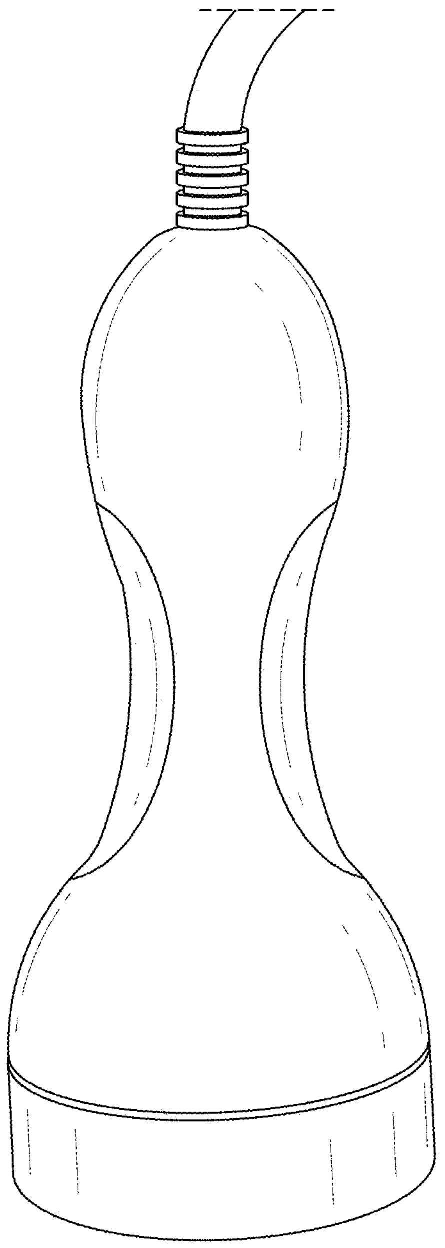
Figure 46C:
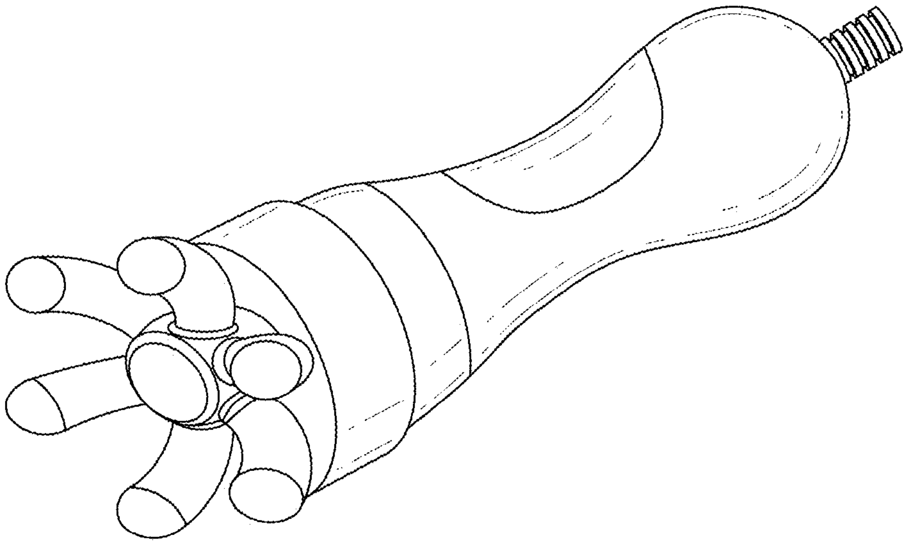
Figure 46E:
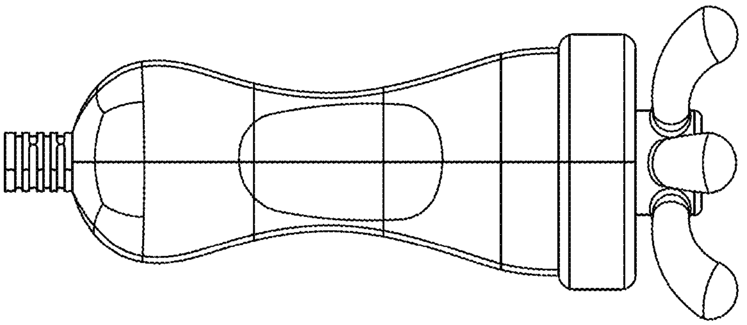
Figure 46D:
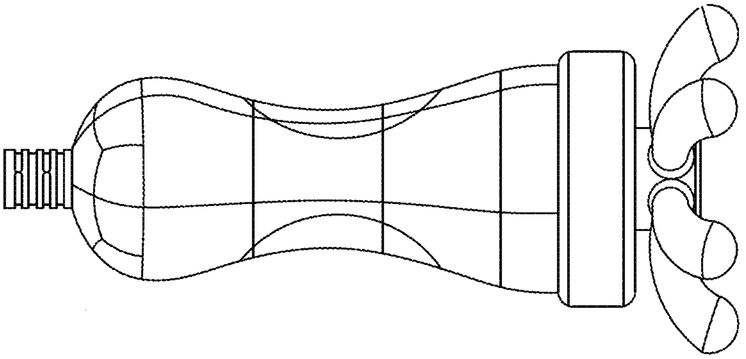
Figure 46G:
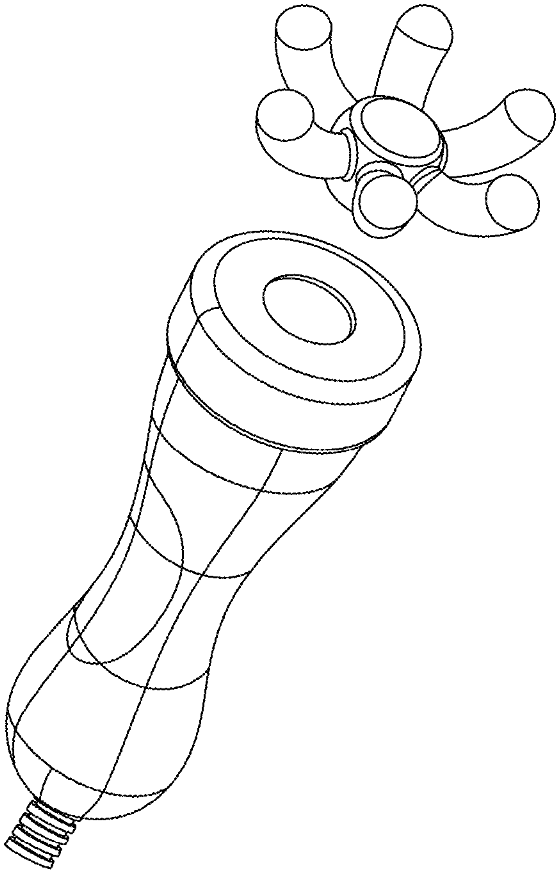
Figure 46F:
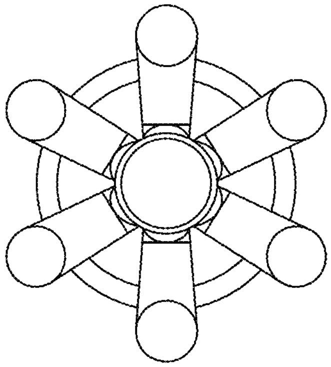
Figure 47:
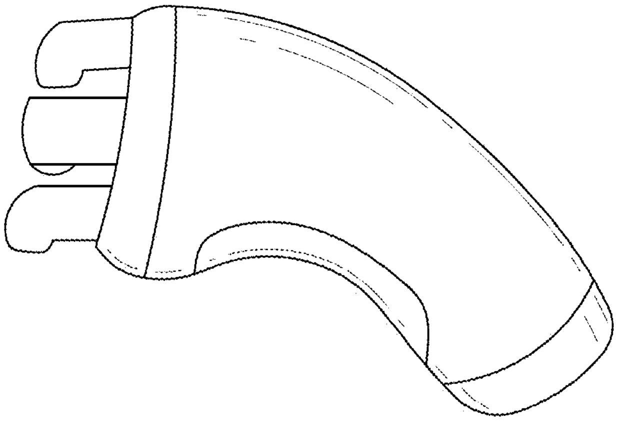
Figure 48:
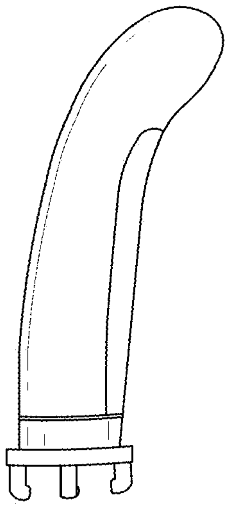
Figure 49:
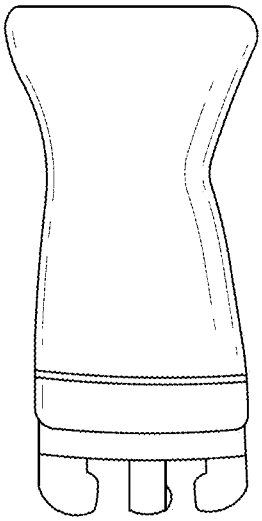
Figure 50:
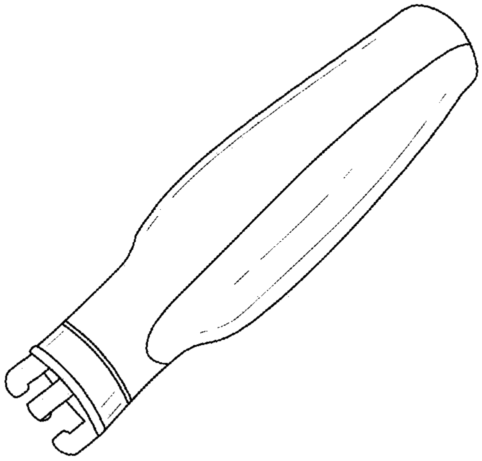
Figure 52:
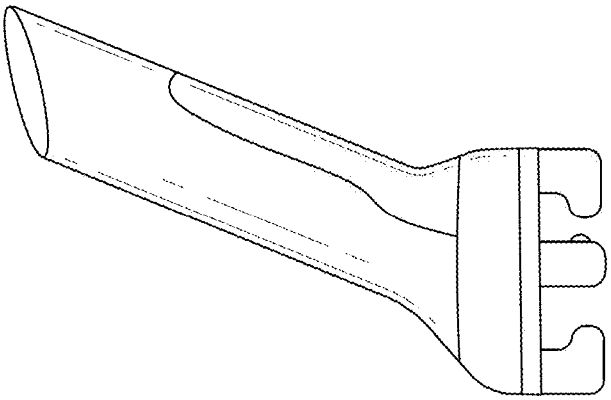
Figure 51:
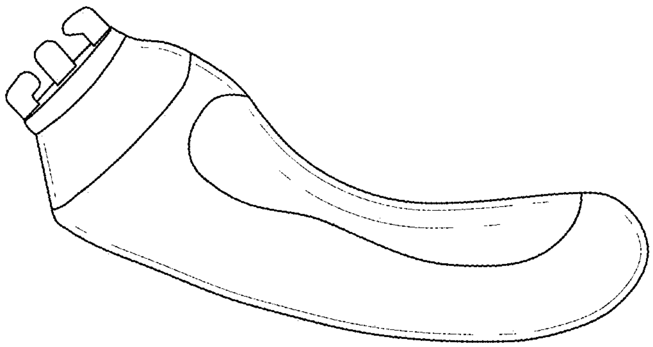
Figure 53:
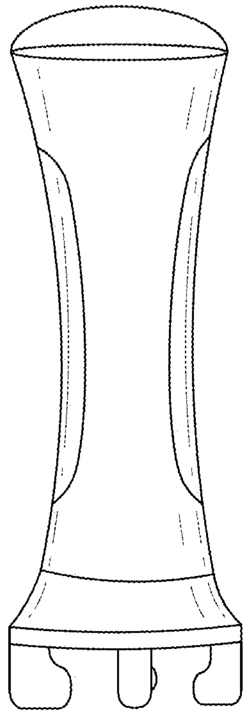
Figure 54:
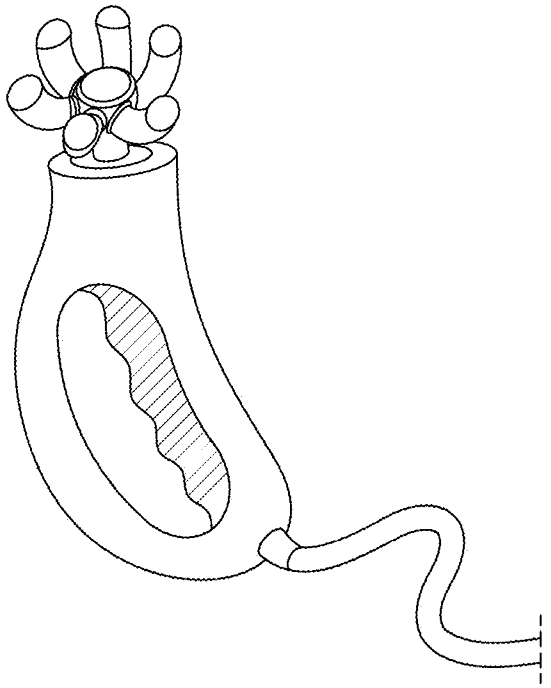
FIG. 54 is an illustration of a front isometric view of yet another illustrative fascia tissue treatment device.
Figure 55:
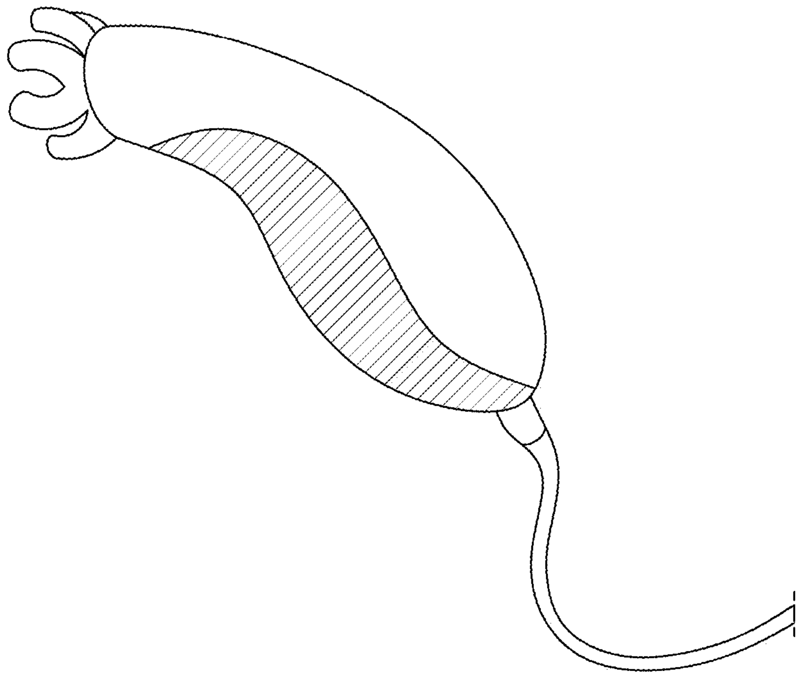
FIG. 55 is a rear isometric view of the illustrative fascia tissue treatment device of FIG. 54.

The size of the therapy device and effectors may also be different in various embodiments. For example, FIG. 45H shows another illustrative fascia tissue treatment device that is designed to treat larger body areas (e.g., the back, legs, stomach, etc.). FIGS. 46-55 show various illustrative fascia tissue therapy devices that are designed to manipulate fascia tissue in smaller body areas or to focus application of treatment. These devices may have a smaller overall footprint that the FIGS. 26-45. As shown in FIGS. 46C-46G, the effector for these smaller devices may include a single tissue treatment element without a separate panel to support the treatment element. As shown in FIGS. 54-55, the size of the handles and/or grip for the therapy device may also differ depending on the size of the therapy device and/or its intended use. In some embodiments, the therapy system (e.g., computing device) may be configured to receive data from remote systems, such as other tissue treatment systems, medical devices, and/or data repositories and may be configured to use the received data to determine and/or adjust a treatment plan for the patient.

Figure 84:
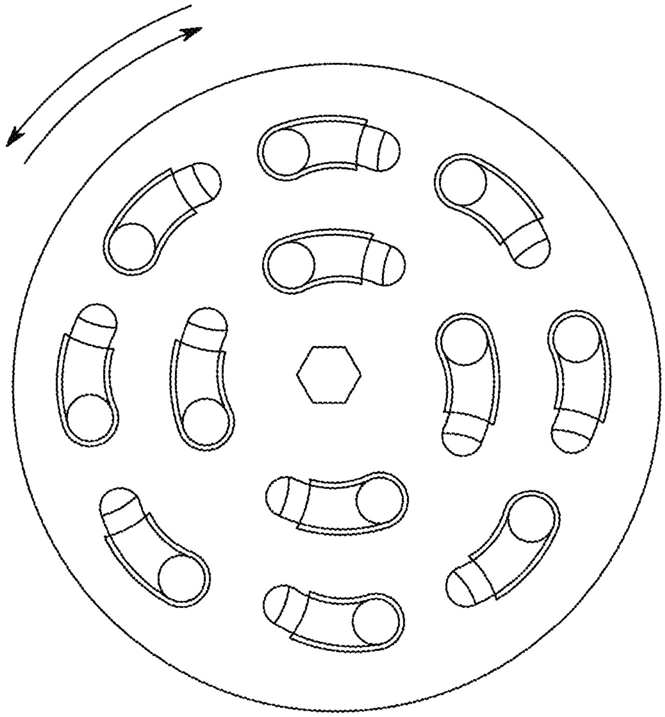
FIG. 84 is an illustration of a bottom view of yet another illustrative tissue treatment effector for a fascia tissue treatment device.
Figure 83:
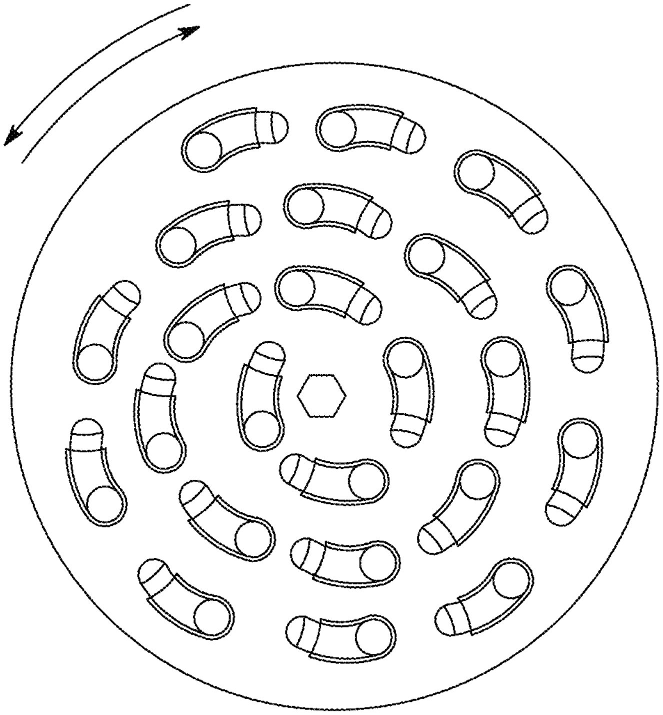
FIG. 83 is an illustration of a bottom view of yet another illustrative tissue treatment effector for a fascia tissue treatment device.

Referring to FIGS. 56-59, an illustrative effector for a fascia tissue therapy device is shown. The effector includes a panel (e.g., board, plate, etc.) that supports a plurality of fascia tissue treatment elements that extend at least partly axially away from the panel. In the embodiment of FIGS. 56-59, the panel is a disk-shaped plate that includes cut-outs for each of the treatment elements. The panel may have an outer diameter within a range between approximately 0.5 inches and 12 inches. In other embodiments, the shape and/or size of the panel may be different. The treatment elements are uniformly distributed across the panel at approximately equal intervals. As shown in FIGS. 56-59, the treatment elements are arranged in concentric rows that are centered about a rotational axis of the panel. In other embodiments, the treatment elements may be arranged in a spiral shape (e.g., as shown in FIG. 83) or another suitable shape. In some embodiments, adjacent rows of treatment elements are rotationally offset from one another (e.g., such that the treatment elements are not aligned along a radial direction, as shown in FIG. 84) to distribute stress more uniformly across the surface of the plate. However, it will be appreciated that the shape, size, and arrangement of treatment elements may be different in other embodiments.

Figure 56:
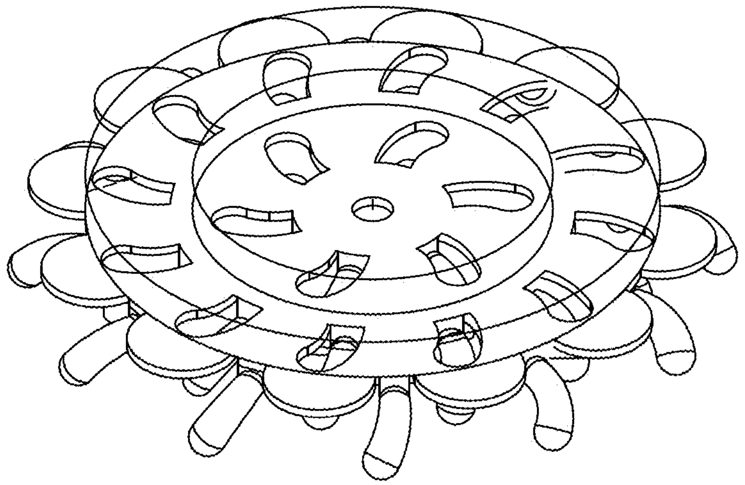
FIG. 56 is an illustration of a bottom isometric view of an illustrative tissue treatment effector.
Figure 60:
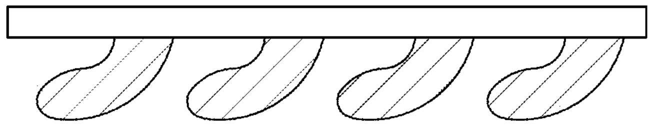
FIG. 60 is an illustration of a side view of yet another illustrative tissue treatment effector.

As shown in FIG. 56, the treatment elements include a plurality of rigid finger members (e.g., claws, etc.) that are fixedly coupled to the panel and extend away from the panel in at least partly axial direction. The plurality of finger members define a plurality of tip portions that are co-planar to one another and are disposed along a reference plane that is parallel to and spaced apart from the panel. In the embodiment of FIGS. 56-59, the finger members are at least partially curved along a direction of rotation of the effector. The finger members each include a first portion extending axially away from the panel, a second portion extending radially away from the first portion, and a third portion extending partly axially away from the second portion and curved along a circumferential direction (e.g., clockwise when viewed from above the plate) about a central axis of the panel. In other embodiments, the size, shape, and arrangement of the finger members along the panel may be different. For example, the finger members may be rotated approximately 90 degrees from the orientation shown in FIGS. 56-59 such that the second portion extends along an at least partly circumferential direction. FIG. 60 shows an illustration of a side cross-sectional view of another illustrative effector. As shown, the finger members each include a first portion engaged with the panel and extending axially away from the panel, and a second portion engaged with the first portion and curved along a circumferential direction, and along a rotational direction of the effector. In this arrangement, the individual finger members form small scooping elements having a smaller radii along an inner surface than an outer, skin facing surface. Beneficially, angling and/or curving the finger members along the circumferential direction improves manipulation of the fascia tissue layers and promotes release and treatment of abnormal/damaged fascia tissue.

Figure 61:
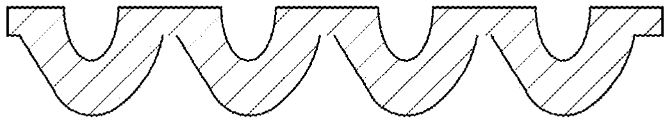
FIG. 61 is an illustration of a side view of yet another illustrative tissue treatment effector.

FIG. 61 shows a side cross-sectional view of yet another illustrative effector. As shown, the treatment elements of the effector includes a plurality of finger members that are curved back toward the panel such that each finger member engages the panel at opposing ends of the finger member. Each finger member may include a cutoff (e.g., straight section) along an outer surface of the finger member, proximate to one end of the finger member, such that the finger members "scoop" or otherwise act against the tissue along a rotational direction of the effector (e.g., along a single rotational direction). As such, reversing the rotational direction of the effector will reduce how aggressively the finger members engage with the patient's tissue. By aligning the orientation of the finger members with the rotation direction, rotational stress of each of the finger members may be reduced.

Figure 62:
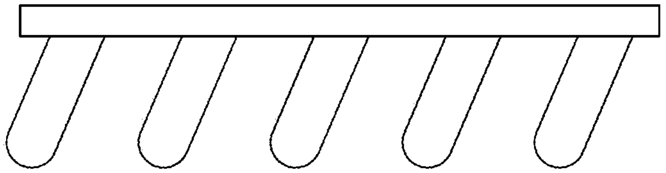
FIG. 62 is an illustration of a side view of yet another illustrative tissue treatment effector.

FIG. 62 shows a side cross-sectional view of yet another illustrative effector. The effector includes a plurality of finger members that extend away from the panel at an oblique angle. As shown in FIG. 62, the finger members are angled along a circumferential direction toward the direction of rotation of the effector.

Figure 57:
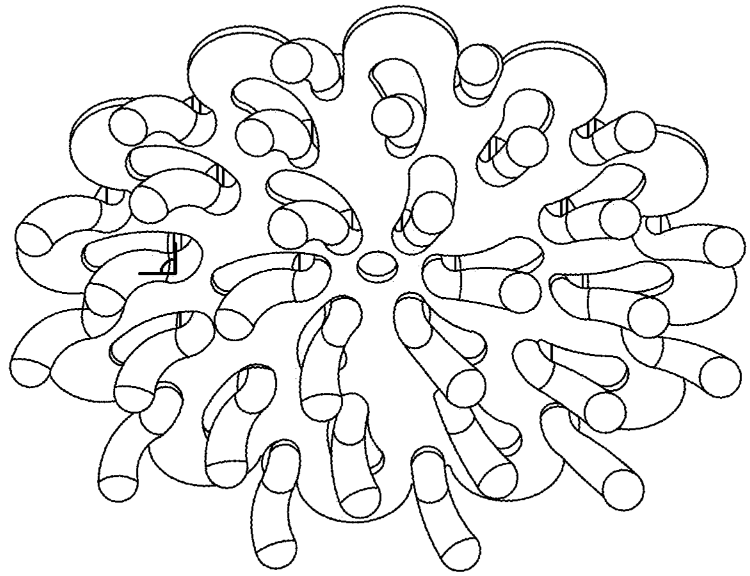
FIG. 57 is a top isometric view of the illustrative tissue treatment effector of FIG. 56.
Figure 58:
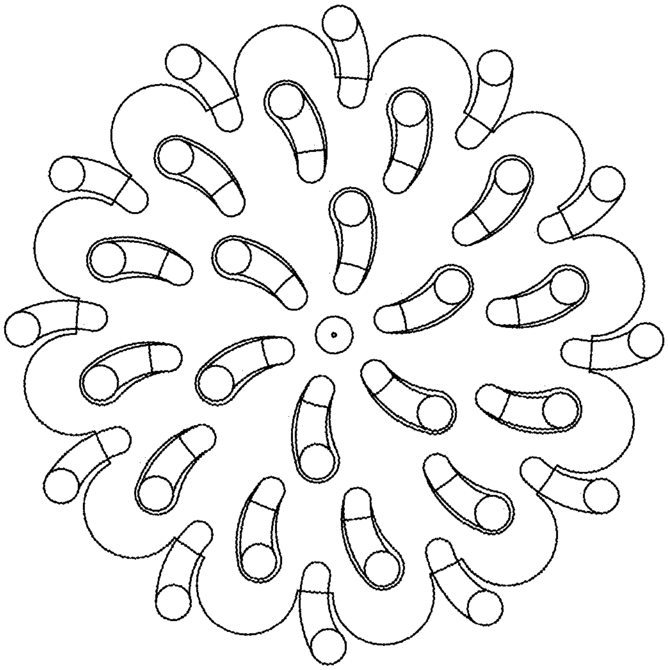
FIG. 58 is a bottom view of the illustrative tissue treatment effector of FIG. 56.
Figure 59:
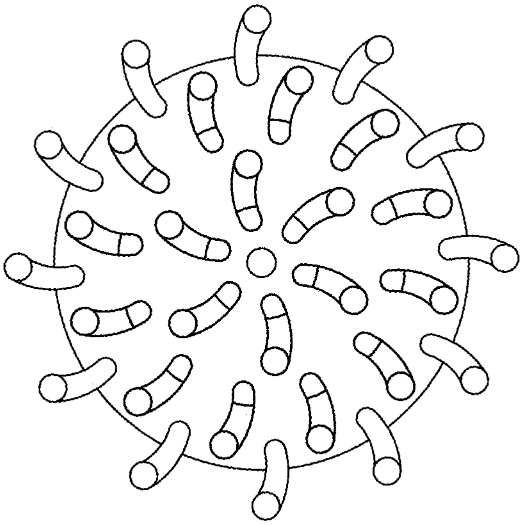
FIG. 59 is an illustration of another illustrative tissue treatment effector.

Returning to FIG. 57, the effector may include a support element to increase the stiffness of the effector and to reduce torque and stress on the actuator. For example, the effector may include a plurality of support ribs between adjacent rings of finger members. The support elements may be disposed on an upper surface of the panel, opposite from the finger members. In some embodiments, support members may also be includes on a skin facing side of the panel (on the same side of the panel as the finger members). As shown in FIG. 57, the support elements are cylindrical ribs that are concentric with a rotational axis of the effector and spaced radially apart from one another. The support elements may also include axial ribs (e.g., spoke ribs, planar ribs, etc.) that engage with and extend between adjacent cylindrical ribs. In some embodiments, the support elements together form a skeletal framework that is engageable with a connector on the therapy device to ensure that the load is more uniformly distributed across the surface of the panel. The ribs (e.g., the cylindrical ribs) may include quick-connect fittings to attach the effector to the therapy device at an intermediate radial position along the panel or at along an outer perimeter of the panel, as described in further detail above.

In some embodiments, the panel may be curved gradually along a radial direction such that a central region of the panel (e.g., proximate to a rotational axis of the effector) is raised above the outer perimeter of the panel. As the effector is pressed toward a patient's skin during treatment, the central region of the panel is pressed toward the skin and into alignment with the rest of the panel (e.g., such that the central region and outer perimeter of the panel are disposed along the same reference plane). The thickness of the panel may be sized such that a force required to align the central region with the outer perimeter of the panel is less than or equal to a target force applied to the skin during treatment (e.g., 1N or another suitable force).

Figure 64:
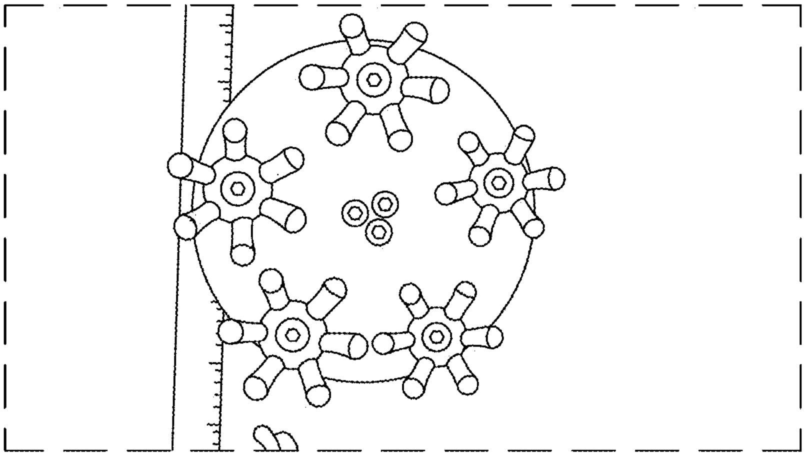
FIGS. 63-66 are illustrations of various illustrative tissue treatment effectors for a fascia tissue treatment device.
Figure 63:
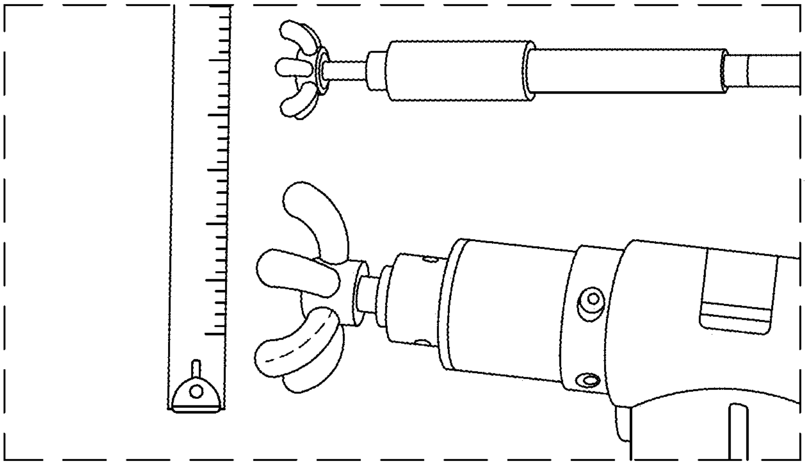
Figure 66:
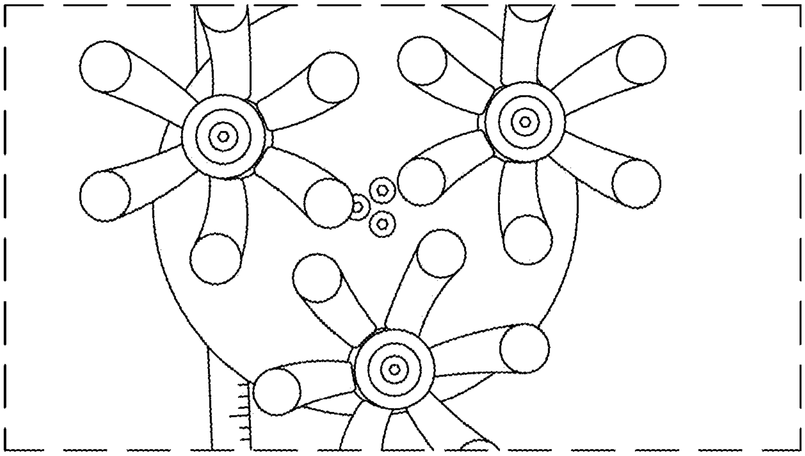
Figure 65:
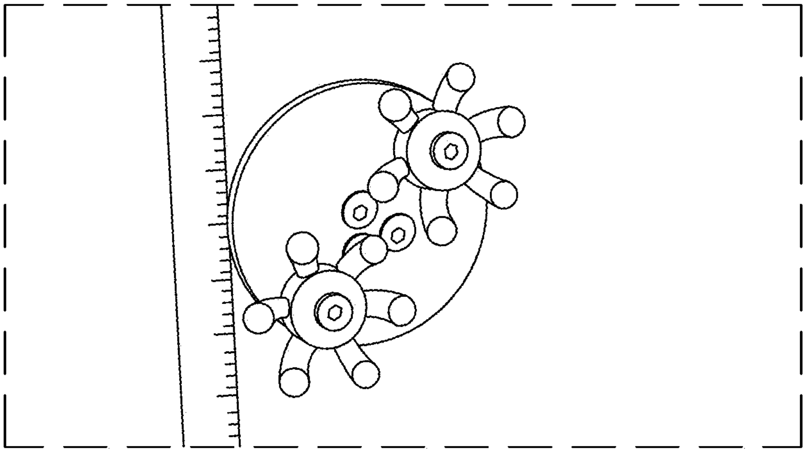

Referring to FIGS. 63-66, various additional illustrative effector designs are shown. In the embodiment of FIG. 63, the effector includes a single tissue treatment element (e.g., flower member, etc.) having a central body and a plurality of fingers extending axially and curving radially away from the central body. FIGS. 64-66 each show an illustrative effector that includes a panel and a plurality of tissue treatment elements coupled to the panel and extending axially away from one side of the panel. The tissue treatment elements may be arranged in at least one ring concentric with a rotational axis of the effector, arranged in rows along a radial direction, or any other suitable arrangement. In one embodiment, and as shown, the treatment elements are mounted to the panel using a fastener (e.g., screw, bolt, etc.) extending through the central body of each individual tissue treatment element. In other embodiments, the tissue treatment elements may be glued, welded to the panel, or otherwise coupled to the panel. In yet other embodiments, the tissue treatment elements may be integrally formed with the panel from a single piece of material. The treatment elements, including the finger members, may be formed of metal or another material that may be sanitized after use without damage. In other embodiments, the treatment elements may be formed from acrylic, PVC, hard rubber, or any other material that is stiff and does not cut or scrape skin of a patient on which the effector is being utilized to help treat or adjust fascia tissue. It will be appreciated that alternative numbers of treatment members may be utilized in accordance with the principles of the present disclosure. The treatment elements are also shown to be substantially identical. However, it will be appreciated that alternative configurations of the treatment elements may be utilized to provide for treating different size anatomical regions.

The treatment elements shown are about 1½ inches in diameter. However, the diameter of the treatment elements may have a fairly wide range (e.g., ½ inch to 6 inches in diameter, etc.). Illustrative treatment elements shown are about ¾ of an inch long and have heads or tips that are about ⅜ of an inch across. The dimensions and configurations (e.g., curves) of the treatment elements, finger members, and tips of the finger members may vary depending on the anatomical region on which the effector is to be used. The tips of the finger members may have one or more same or different dimensions as the finger members (e.g., the tips may have a larger diameter by being bulbous). The finger members are shown to be curved. Alternative configurations, such as finger members being straight may be utilized as well. The treatment elements are each shown to be a single member. However, in other embodiments, the treatment elements may be formed from multiple elements. Still yet, rather than the effector using treatment elements that have a flower or cactus-like appearance (i.e., central portion with extending finger members), treatment elements with non-flower-like appearance may be utilized, as well, that still provides a user with a number of closely spaced pressure-point elements that can be pressed and guided along a patient's skin to cause fascia tissue to be released or perform a non-therapeutic function. The finger members may be substantially the same length (e.g., less than 0.1 inch difference in length between finger length) such that the tips of the finger members are substantially co-planer and parallel to a support structure (in the case of a flat support structure) so that a pressure load applied to the skin and fascia tissue is substantially equally applied by each of the finger members.

Each of the treatment elements is shown to have six finger members. Alternative numbers of finger members may be utilized in accordance with the principles of the present disclosure. The finger members may be stiff or rigid (e.g., inflexible, etc.), thereby having minimum bend or deformation during usage of the device on fascia tissue of a patient.

The panel may have openings (not shown) defined by the panel through which a screw or other fastening mechanism may extend through treatment elements into the panel. After fastening the treatment elements to the panel, glue or other fastening material, such as epoxy, may be utilized to secure the treatment elements to the panel. A cover (not shown) above the fastening mechanisms may be utilized to limit the ability for someone to access or remove the fastening mechanisms of the treatment elements. Alternatively, the treatment elements may be configured to allow for a user to more easily replace the treatment elements to change size, replace broken flower members, or otherwise.

Figure 67:
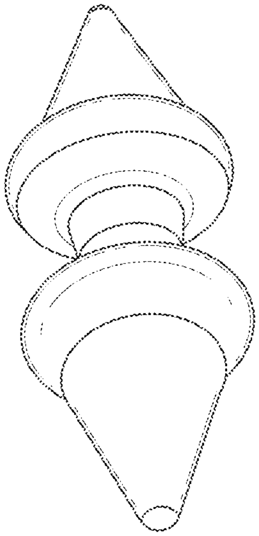
FIG. 67 is an illustration of an isometric view of a tissue treatment element for a fascia tissue treatment device.

Referring to FIG. 67, another illustrative treatment element structure is shown that may be used in place of one or more finger members of the effector, and/or as a standalone treatment element that may be used by the treatment device to manipulate fascia tissue. In the embodiment shown, the treatment element is a refining tool that is used to target small or stubborn areas of fascia tissue. The treatment element includes a base and a conically-shaped extension engaged with and extending away from the base. The treatment device (e.g., actuator) may be configured to press a tip of the conically-shaped element into a patient's tissue and then move the treatment element along a circular path to work the affected area. In other embodiments, the treatment device (e.g., actuator) may be configured to rotate the tip of the treatment element by pivoting the element from the base. It will be appreciated that various treatment element shapes and sizes may be used in other embodiments.

Figure 68:
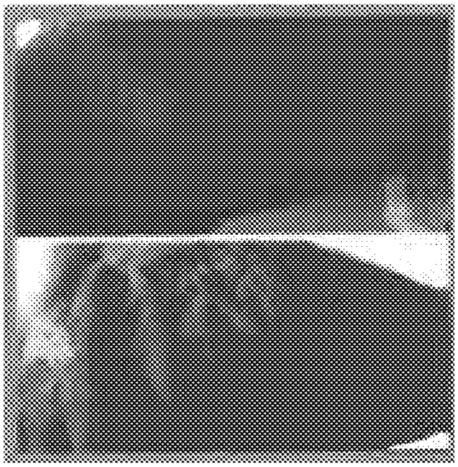
FIGS. 68-75 are various before and after photographs of patients after using a fascia tissue therapy system.
Figure 69:
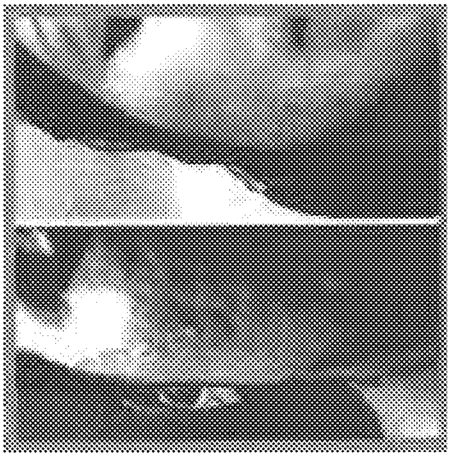
Figure 70:
Figure 71:
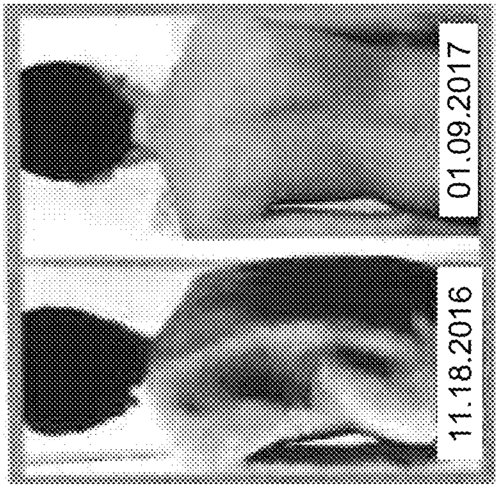
Figure 72:
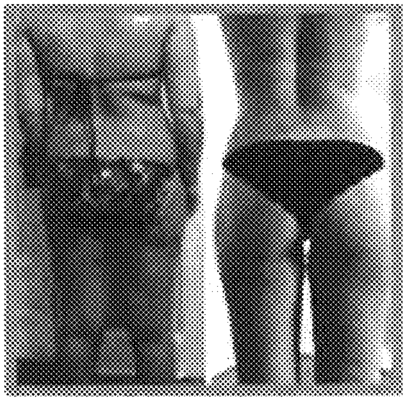
Figure 73:
Figure 74:
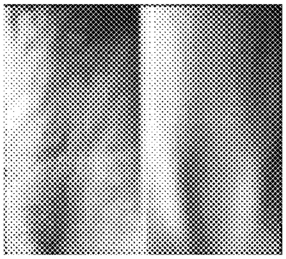
Figure 75:
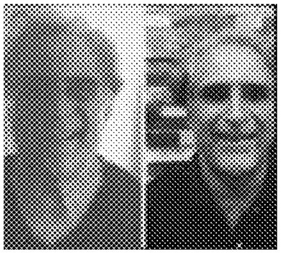
Figure 76:
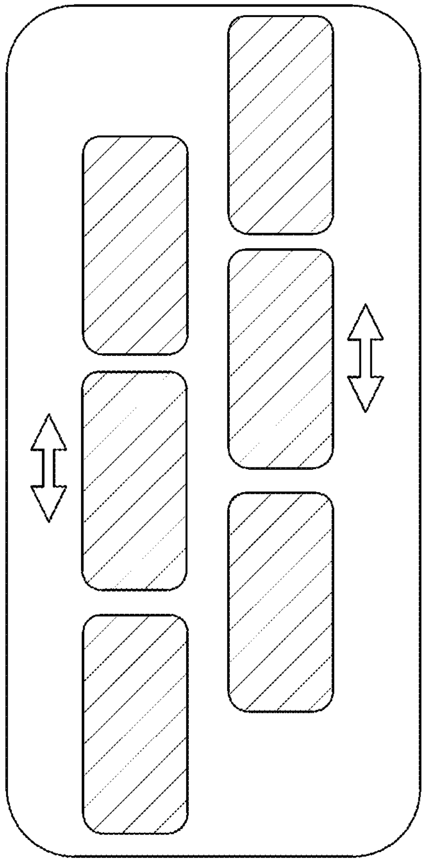
FIGS. 76-77 are illustrations of bottom views of yet another illustrative fascia tissue treatment device.
Figure 77:
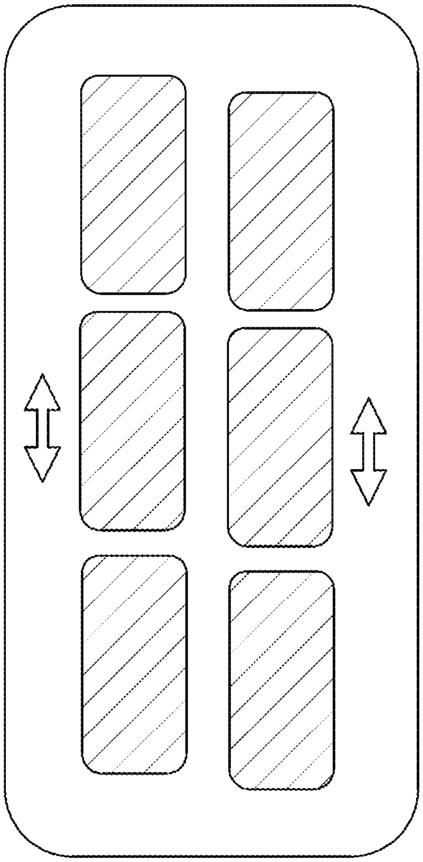
Figure 78:
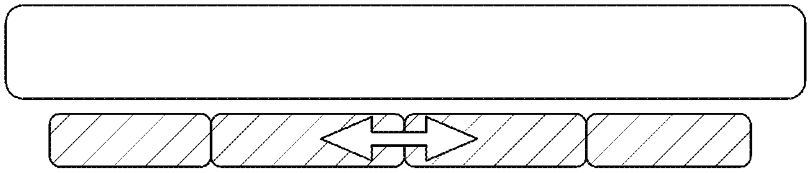
FIG. 78 is an illustration of a side view of the illustrative fascia tissue treatment device of FIG. 76.
Figure 79:
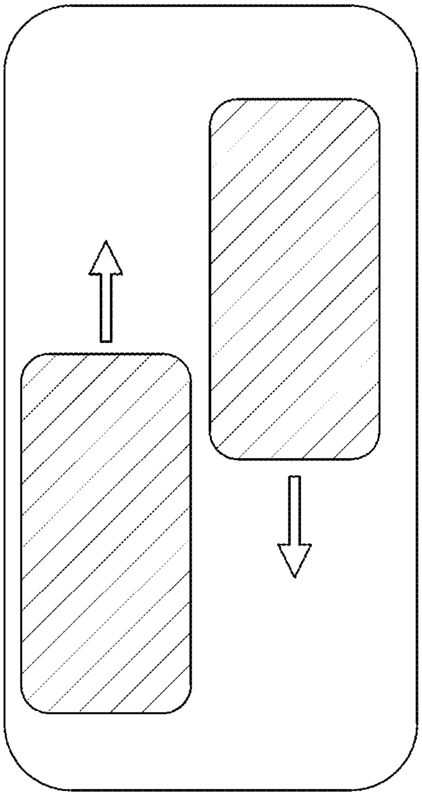
FIGS. 79-81 are illustrations of bottom views of yet another illustrative fascia tissue treatment device.
Figure 80:
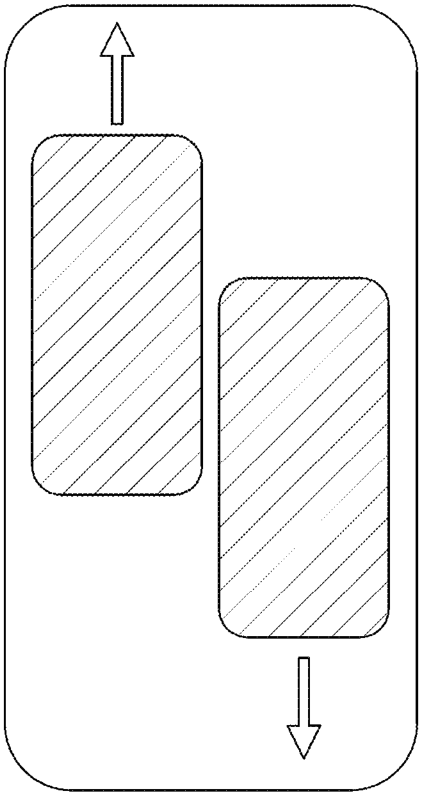
Figure 81:
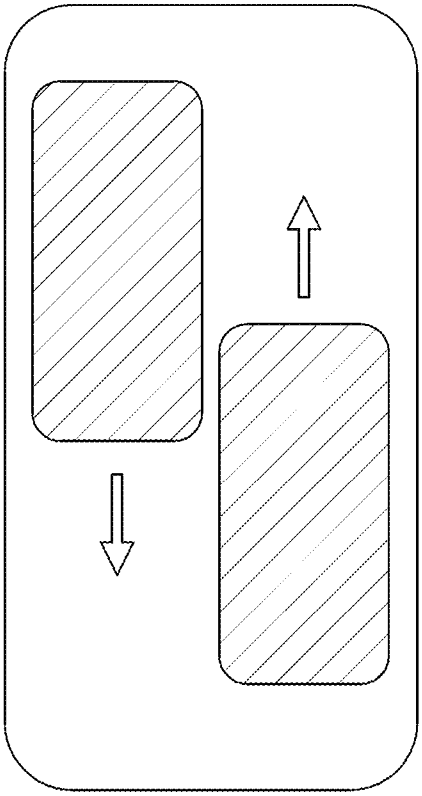
Figure 82:
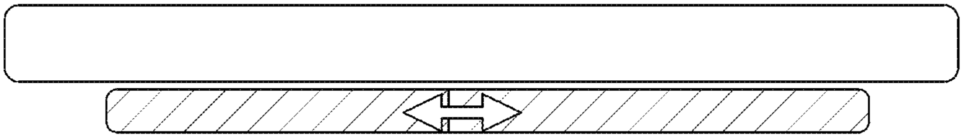
FIG. 82 is an illustration of a side view of the illustrative fascia tissue treatment device of FIG. 79.

While certain features of the therapy device are configured to be optimal usage on fascia tissue, the features also provide for ornamental appearance. It should be understood that the therapy device may be used for increasing overall myo-fascial fitness to loosen fascia tissue that is constrained, improve health and/or beauty purposes (e.g., provide a satisfactory feeling to a user and/or alter the appearance of cellulite and skin smoothness). Moreover, usage of the fascia tissue fitness device may open, loosen, restore, and/or revitalize fascia tissue of men and women, young and old. FIGS. 68-75 show photographs demonstrating some of the various benefits that can be provided by using the therapy system. For example, FIG. 68 shows a significant reduction in the amount of cellulite presenting through a patient's skin along a leg after treatment. The therapy system can also be used to treat acne (FIG. 69), scar tissue (FIG. 70), and/or other dermatological conditions. FIG. 71 shows improvements in patients that are suffering from scoliosis and/or other forms of postural misalignment. The therapy system can be used to redistribute fatty tissues (FIG. 73), promote and restore hair growth (FIG. 73) (e.g., improving blood circulation to hair follicles, reducing stress on tissue from realignment of the fascia layers, etc.), restructure and remodel fascia to improve skin tightening (FIG. 74) in different body areas, and to stimulate neurological connectivity and/or improve motor control for patient's suffering from paralysis (e.g., as a result of a stroke as shown in FIG. 75 or other injury).

While various embodiments of the therapy system have been described in the context of use in medical environments, it will be appreciated that the therapy system may be also used in other applications. For example, the therapy system could be installed in a workout and/or training facility and used as part of a person's workout regimen, to improve physical appearance, stimulate blood flow, and/or improve recovery times. A miniaturized version of the therapy system could also be used for home use or in various other applications. Data from the computing device could be transmitted wirelessly to a personal device (e.g., smart phone, tablet, etc.) for additional review and analysis through applications installed on the user device (e.g., software as a service, etc.). The application may be configured to ensure compliance with health information privacy policies (e.g., the health insurance portability and accountability act (HIPPA), etc.) and may limit user access to certain data.

The previous description is of a preferred embodiment for implementing the invention, and the scope of the invention should not necessarily be limited by this description. The scope of the present invention is instead defined by the following claims.

Features List

- Base Station
  - mechanical configuration for storing treatment devices
  - hanging heads
  - rotate internal/external feature(s)
  - electrical configuration for powering various devices
  - computer/software for supporting patient treatments (rotate/tip/tilt feature on top of base station)
  - modality processes
    - guide operator for starting pre-treatment,
    - capture images (e.g., ultrasound), compare images (e.g., current versus previous images(s)), auto-analysis and treatment determination
    - (automatically) define treatment(s) to be performed
    - pre-programmed to provide instructions to operator (e.g., identify heads to use, automatically determine and confirm head used, program heads with force ranges (max, min to provide notice to operator if outside range))
  - collect duration of treatment and forces with time-stamps
  - patient scheduling
  - operator sign-in
  - many other automated and non-automated features Improved ultrasound capabilities (e.g., resolution) to assist with creating treatment identification/classification, including KNN analysis (tissue identification patient grouping for treatment plans)

- We might care about different resolutions more than others (2, 3, or 4 different resolutions to get a sense for what is being changed)—repeat this at intervals over time
- AI for pattern recognition—groups of these patterns (Develop a treatment protocol here (k nearest neighbor scatterplot))
  - Also may be used to help figure out required number of treatments using AI to classify fascia problems for treatment analysis (fascia depth, alignment or fragmentation, improvement over time, etc.)

- Using AI for pattern matching at different depths (head sizes, speeds, etc.)

1*. Tissue treatment elements on a rotating disc or other shaped surface

- (direct drive actuators in the therapy devices. Low weight to torque ratio, cost. Reduced heat and no gear oil since this device is a direct drive device so no gearbox) (https://roboticsandautomationnews.com/2021/06/08/genesis-robotics-releases-long-awaited-livedrive-direct-drive-actuators/43737/)

2. Automatically move tissue treatment members using actuators in a programmatic manner (speeds, durations, notifications for changing modalities, protocols, heads, etc.)

3. "Dinosaur feet" action

- resistance of each foot (pedal) to skin

4*. Pressure sensors to sense force being applied to patient (could be more than a single pressure sensor)

5*. Spinning/vibrating disc configuration

6. Electrical current sensor to sense rotational torque of motor Attach motor to the outside of the disc to improve control and move the moment arm outwards so as to reduce pressure placed on a single center point of the disc Diameter of motor itself connected to disc

- Not a topical use—pressing in a lot here to message to get down to lower portions of fascia tissue
- Claim the configuration of the attachment points—not in the center—out at the sides to limit the moment arm
- pneumatics/hydraulics/electromagnetics 7. Visual, audio, tactile feedback on treatment head and/or base as a function of rotation speed, torque, and/or force for operator set limits of speed, force, torque 8*. Multiple size and/or configurations of treatment elements Multiple configuration of treatment elements, not just claws to avoid design-arounds (e.g., fingers connected directly to disk) Radial rows of fingers Offset rows Take language from existing cases to deal with geometry Fingers oriented in direction of rotation 9. Easy replaceable discs onto heads (mainly for consumer version)

surfaces ½ inch to 12 inches

Evenly distributed tissue treatment elements

All tips of fingers of tissue treatment elements co-planar

10*. Heads heat exhaust variety of structures for holding and applying force with one or two hands lighting around head with dynamic color (red, yellow, green) based on force (as a whole, on quads)

different functions (e.g., ultrasound, IR, spinning only, vibrating only, spinning and vibrating, micro-currents)

specific motor design, if novel

11. Pressure sensors (novelty search being performed with spinning disc of #1)

pressure sensors for each claw/finger in quadrants of disc feedback based on sensed pressure calibration, average pressure, peak pressure, etc.

12. Auto-shut off based on torque, temperature, force auto shut off button force sensor dead man switch 13. Setting selector (on head)

Stiffness, speed limiter, etc.

provide modality guidance on therapy device

14. Pre-treatment

IR "storm trooper" pieces (pre-treatment heating device with a shell)

communicate pre-treatment data (wirelessly) to station computer for auto-capture 15. Post-treatment Kryo-devices (packs, heads, etc.)

communicate post-treatment (wirelessly) to station computer for auto-capture

What is claimed is:

1. A powered treatment device for fascia tissue fitness, comprising:

a housing;

an actuator coupled to and disposed within the housing; and an interchangeable tissue treatment assembly, including:

a plate detachably and operably coupled to the actuator and configured to be powered by the actuator to rotate with respect to the housing; and a tissue treatment element fixedly coupled to the plate, the tissue treatment element comprising a plurality of elongated finger members that are rigid and extend away from the plate, the plurality of elongated finger members defining a plurality of respective tip portions, the tip portions being co-planar and disposed along a reference plane that is spaced apart from and substantially parallel to the plate, at least one finger member of the plurality of elongated finger members defining a central axis extending from a proximal end to a distal end of the at least one finger member, the central axis of the at least one finger member extending at least partly along a circumferential direction relative to a central axis of the plate, the at least one finger member including a shaft about the central axis of the at least one finger member, the shaft defining a convex surface extending between the proximal end and the distal end of the at least one finger member, the shaft further defining a concave surface opposite the convex surface, the concave surface oriented along a direction of rotation of the plate when rotated by the actuator, the concave surface being at least in part parallel to the convex surface and the central axis of the at least one finger member.

2. The powered treatment device of claim 1, wherein the actuator comprises a direct drive motor that is coupled to the interchangeable tissue treatment assembly without an intervening gear set.

3. The powered treatment device of claim 1, wherein the tissue treatment element further comprises a support member extending axially away from the plate, a distal end of the support member coupled to each one of the plurality of elongated finger members.

4. The powered treatment device of claim 1, wherein the tissue treatment element is one of a plurality of tissue treatment elements fixedly coupled to the plate and arranged in approximately equal intervals along a surface of the plate.

5. The powered treatment device of claim 1, wherein at least one of the plurality of elongated finger members extends radially beyond an outer perimeter of the plate.

6. A fascia tissue therapy system, comprising:

a base station, including:

an enclosure defining an interior cavity;

a power source disposed within the interior cavity;

a door coupled to the enclosure and moveable to selectively provide access to the interior cavity;

a tether electrically coupled to the power source and movably extendable away from the base station;

a powered treatment device detachably coupled to the tether, and including:

a housing;

an actuator coupled to and disposed within the housing; and an interchangeable tissue treatment assembly, including:

a plate detachably and operably coupled to the actuator and configured to be powered by the actuator to rotate with respect to the housing; and a tissue treatment element fixedly coupled to the plate, the tissue treatment element comprising a plurality of elongated finger members that are rigid and extend away from the plate, the plurality of elongated finger members defining a plurality of respective tip portions, the tip portions being co-planar and disposed along a reference plane that is spaced apart from and substantially parallel to the plate, at least one finger member of the plurality of elongated finger members defining a central axis extending from a proximal end to a distal end of the at least one finger member, the central axis of the at least one finger member extending at least partly along a circumferential direction relative to a central axis of the plate, the at least one finger member including a shaft about the central axis of the at least one finger member, the shaft defining a convex surface extending between the proximal end and the distal end of the at least one finger member, the shaft further defining a concave surface opposite the convex surface, the concave surface oriented along a direction of rotation of the plate when rotated by the actuator, the concave surface being at least in part parallel to the convex surface and the central axis of the at least one finger member; and a controller communicatively coupled to at least one of the power source or the powered treatment device and configured to control operation of the powered treatment device.

7. The fascia tissue therapy system of claim 6, further comprising:

a carousel disposed within the interior cavity and rotatably coupled to the enclosure, the carousel having a plurality of mounts arranged circumferentially about a rotational axis of the carousel to support a plurality of power treatment devices.

8. The fascia tissue therapy system of claim 6, wherein the actuator is configured to rotate in a circular manner.

* * * * *